United States Patent
Auer et al.

(10) Patent No.: US 9,714,292 B2
(45) Date of Patent: Jul. 25, 2017

(54) BISPECIFIC ANTIBODIES AGAINST HUMAN TWEAK AND HUMAN IL17 AND USES THEREOF

(71) Applicant: Hoffmann-La Roche Inc., Little Falls, NJ (US)

(72) Inventors: Johannes Auer, Schwaigen (DE); Martin Bader, Penzberg (DE); Jens Fischer, Weilheim in Oberbayern (DE); Hubert Kettenberger, Munich (DE); Maximiliane Koenig, Munich (DE); Stefan Lorenz, Penzberg (DE); Joerg Moelleken, Munich (DE)

(73) Assignee: Hoffmann-La Roche Inc., Little Falls, NJ (US)

( * ) Notice: Subject to any disclaimer, the term of this patent is extended or adjusted under 35 U.S.C. 154(b) by 0 days.

(21) Appl. No.: 14/506,408

(22) Filed: Oct. 3, 2014

(65) Prior Publication Data

US 2015/0132307 A1    May 14, 2015

Related U.S. Application Data

(63) Continuation of application No. PCT/EP2013/056970, filed on Apr. 3, 2013.

(30) Foreign Application Priority Data

Apr. 5, 2012  (EP) .................... 12163396

(51) Int. Cl.
| A61K 39/395 | (2006.01) |
| C07K 16/28 | (2006.01) |
| C07K 16/24 | (2006.01) |
| A61K 39/00 | (2006.01) |

(52) U.S. Cl.
CPC ........ *C07K 16/2875* (2013.01); *C07K 16/244* (2013.01); *A61K 2039/505* (2013.01); *C07K 2317/24* (2013.01); *C07K 2317/31* (2013.01); *C07K 2317/35* (2013.01); *C07K 2317/565* (2013.01); *C07K 2317/73* (2013.01); *C07K 2317/76* (2013.01); *C07K 2317/92* (2013.01); *C07K 2317/94* (2013.01)

(58) Field of Classification Search
None
See application file for complete search history.

(56) References Cited

U.S. PATENT DOCUMENTS

| 5,202,238 A | 4/1993 | Fell, Jr. et al. |
| 5,204,244 A | 4/1993 | Fell et al. |
| 5,716,623 A | 2/1998 | Yao et al. |
| 5,959,083 A | 9/1999 | Bosslet et al. |
| 6,063,372 A | 5/2000 | Banchereau et al. |
| 6,171,586 B1 | 1/2001 | Lam et al. |
| 6,267,958 B1 | 7/2001 | Andya et al. |
| 6,274,711 B1 | 8/2001 | Golstein et al. |
| 6,350,860 B1 | 2/2002 | Buyse et al. |
| 6,511,663 B1 | 1/2003 | King et al. |
| 6,897,044 B1 | 5/2005 | Braslawsky et al. |
| 7,129,330 B1 | 10/2006 | Little et al. |
| 2005/0079170 A1 | 4/2005 | Le Gall et al. |
| 2005/0100543 A1 | 5/2005 | Hansen et al. |
| 2005/0163782 A1 | 7/2005 | Glaser et al. |
| 2005/0260186 A1 | 11/2005 | Bookbinder et al. |
| 2006/0104968 A1 | 5/2006 | Bookbinder et al. |
| 2010/0015133 A1 | 1/2010 | Igawa et al. |
| 2010/0266531 A1* | 10/2010 | Hsieh .................. C07K 16/241 424/85.2 |
| 2015/0315296 A1 | 11/2015 | Schaefer et al. |

FOREIGN PATENT DOCUMENTS

| EP | 0 307 434 B1 | 9/1993 |
| EP | 1 870 459 A1 | 12/2007 |
| WO | 91/06305 A1 | 5/1991 |
| WO | 92/04053 A1 | 3/1992 |
| WO | 95/09917 A1 | 4/1995 |
| WO | 95/18826 A2 | 7/1995 |
| WO | 95/18826 A3 | 7/1995 |
| WO | 96/17939 A1 | 6/1996 |
| WO | 96/27011 A1 | 9/1996 |
| WO | 97/01580 A1 | 1/1997 |
| WO | 97/15320 A1 | 5/1997 |
| WO | 97/22596 A1 | 6/1997 |
| WO | 97/30035 A1 | 8/1997 |
| WO | 97/32856 A1 | 9/1997 |
| WO | 98/05783 A1 | 2/1998 |
| WO | 98/13354 A1 | 4/1998 |
| WO | 98/50431 A2 | 11/1998 |
| WO | 98/50431 A3 | 11/1998 |
| WO | 99/02166 | 1/1999 |
| WO | 99/35276 A1 | 7/1999 |
| WO | 00/40529 A1 | 7/2000 |
| WO | 00/41669 A2 | 7/2000 |
| WO | 00/41669 A3 | 7/2000 |

(Continued)

OTHER PUBLICATIONS

Alvaro-Gracia et al., "Mutual antagonism between interferon-gamma and tumor necrosis factor-alpha on fibroblast-like synoviocytes: paradoxical induction of IFN-gamma and TNf-alpha receptor expression" J Clin Immunol 13(3):212-218 ( 1993).

Atwell et al., "Stable heterodimers from remodeling the domain interface of a homodimer using a phage display library" J Mol Biol 270(1):26-35 ( 1997).

Barnes et al., "Advances in animal cell recombinant protein production: GS-NS0 expression system" Cytotechnology 32(2):109-23 (Feb. 2000).

(Continued)

*Primary Examiner* — Dong Jiang
(74) *Attorney, Agent, or Firm* — Morrison & Foerster LLP

(57) ABSTRACT

The present invention relates to Bispecific antibodies against human TWEAK and human IL17 (bispecific TWEAK-IL17 antibodies), methods for their production, pharmaceutical compositions containing said antibodies, and uses thereof.

14 Claims, 3 Drawing Sheets

(56) References Cited

FOREIGN PATENT DOCUMENTS

| | | | |
|---|---|---|---|
| WO | 00/42073 A1 | 7/2000 | |
| WO | 00/69436 A1 | 11/2000 | |
| WO | 01/77342 A1 | 10/2001 | |
| WO | 01/92224 A1 | 12/2001 | |
| WO | 02/04434 A1 | 1/2002 | |
| WO | 02/08213 A1 | 1/2002 | |
| WO | 03/086311 A2 | 10/2003 | |
| WO | 03/086311 A3 | 10/2003 | |
| WO | 2005/051422 A1 | 6/2005 | |
| WO | 2006/013107 A1 | 2/2006 | |
| WO | 2006/020258 A2 | 2/2006 | |
| WO | 2006/044908 A2 | 4/2006 | |
| WO | 2006/044908 A3 | 4/2006 | |
| WO | 2006/052926 A2 | 5/2006 | |
| WO | 2006/052926 A3 | 5/2006 | |
| WO | 2006/088890 A2 | 8/2006 | |
| WO | 2006/088890 A3 | 8/2006 | |
| WO | 2006/089095 A2 | 8/2006 | |
| WO | 2006/089095 A3 | 8/2006 | |
| WO | 2006/122187 A2 | 11/2006 | |
| WO | 2006/122187 A3 | 11/2006 | |
| WO | 2006/130374 A2 | 12/2006 | |
| WO | 2006/130374 A3 | 12/2006 | |
| WO | 2006/130429 A2 | 12/2006 | |
| WO | 2006/130429 A3 | 12/2006 | |
| WO | 2007/024715 A2 | 3/2007 | |
| WO | 2007/024715 A3 | 3/2007 | |
| WO | 2007/024715 A9 | 3/2007 | |
| WO | 2007/027761 A2 | 3/2007 | |
| WO | 2007/027761 A3 | 3/2007 | |
| WO | 2007/109254 A2 | 9/2007 | |
| WO | 2007/147901 A1 | 12/2007 | |
| WO | 2008/002115 A1 | 1/2008 | |
| WO | 2008/106131 A2 | 9/2008 | |
| WO | 2008/106131 A3 | 9/2008 | |
| WO | 2009/080253 A1 | 7/2009 | |
| WO | 2009/089004 A1 | 7/2009 | |
| WO | WO-2009/080251 A1 | 7/2009 | |
| WO | WO-2009/080252 A1 | 7/2009 | |
| WO | 2010/003108 A2 | 1/2010 | |
| WO | 2010/003108 A3 | 1/2010 | |
| WO | 2010/034443 A1 | 4/2010 | |
| WO | 2010/102251 A3 | 9/2010 | |
| WO | 2010/102551 A2 | 9/2010 | |
| WO | 2010/112193 A1 | 10/2010 | |
| WO | 2010/115555 A2 | 10/2010 | |
| WO | 2010/115555 A3 | 10/2010 | |
| WO | WO-2010/115589 A1 | 10/2010 | |
| WO | WO-2010/115589 A8 | 10/2010 | |
| WO | 2010/129304 A2 | 11/2010 | |
| WO | 2010/129304 A3 | 11/2010 | |
| WO | 2010/145792 A1 | 12/2010 | |
| WO | 2010/145793 A1 | 12/2010 | |
| WO | 2011/028952 A1 | 3/2011 | |
| WO | 2011/091078 A2 | 7/2011 | |
| WO | 2011/117330 A1 | 9/2011 | |
| WO | WO-2011/163478 A2 | 12/2011 | |
| WO | WO-2011/163478 A3 | 12/2011 | |
| WO | 2012/009544 A2 | 1/2012 | |
| WO | 2012/009544 A3 | 1/2012 | |
| WO | WO-2012/018790 A2 | 2/2012 | |
| WO | WO-2012/018790 A3 | 2/2012 | |
| WO | 2012/045671 A1 | 4/2012 | |

OTHER PUBLICATIONS

Barnes et al., "Characterization of the stability of recombinant protein production in the GS-NS0 expression system" Biotechnol Bioeng 73(4):261-70 (May 2001).
Boackle et al., "An IgG primary sequence exposure theory for complement activation using synthetic peptides" Nature 282:742-3 (Dec. 1979).
Brunhouse, R. et al., "Isotypes of IgG comparison of the primary structures of three pairs of isotypes which differ in their ability to activate complement" J Mol Immunol 16:907-917 (1979).
Burton et al., "The Clq Receptor Site on Immunoglobulin G." Nature 288(5789):338-344 (Nov. 27, 1980).
Carter et al., "Humanization of an anti-p185 HER2 antibody for human cancer therapy" P Natl Acad Sci USA 89:4285-4289 (May 1992).
Coloma and Morrison, "Design and production of novel tetravalent bispecific antibodies" Nat Biotechnol 15(2):159-163 (Feb. 1997).
Crispin et al., "Expanded double negative T cells in patients with systemic lupus erythematosus produce IL-17 and infiltrate the kidneys" J Immunol 181:8761-8766 (2008).
Durocher et al., "High-level and high-throughput recombinant protein production by transient transfection of suspension-growing human 293-EBNA1 cells" Nucleic Acids Res 30(2):E9 (2002).
European Search Report for European Patent Application No. 12163396.0-2406 dated Sep. 19, 2012.
Firestein et al., "Apoptosis in rheumatoid arthritis synovium" J. Clin Invest 96:1631-1638 (Sep. 1995).
Firestein et al., "Apoptosis in rheumatoid arthritis, p53 overexpression in rheumatoid arthritis synovium" Am J Pathol 149(6):2143-2151 (1996).
Firestein et al., "IL-1 receptor antagonist protein production and gene expression in rheumatoid arthritis and osteoarthritis synovium" J Immunol 149:1054-1062 (Aug. 1, 1992).
Firestein et al., Synovial interleukin-1 receptor antagonist and interleukin-1 balance in rheumatoid arthritis, Arthritis Heum 37(5): 644-652 (Abstract) (May 1994).
Fischer et al., "Bispecific Antibodies: Molecules that Enable Novel Therapeutic Strategies" Pathobiology 74:3-14 (2007).
Geisse et al., "Eukaryotic Expression Systems: A Comparison" Protein Expres Purif 8:271-282 (1996).
He et al., "Screening of monoclonal antibody formulations based on high-throughput thermostability and viscosity measurements: Design of experiment and statistical analysis" J Pharm Sci 100(4):1330-40 (Apr. 2011).
Hellings et al., "Interleukin-17 orchestrates the granulocyte influx into airways after allergen inhalation in a mouse model of allergic asthma" Am J Respir Cell Mol Biol 28:42-50 (2003).
Holliger et al., "Engineered Antibody Fragments and the Rise of Single Domains" Nature Biotechnol 23(9):1126-1136 (2005).
Idusogie et al., "Mapping of the C1q Binding Site on Rituxan, A Chimeric Antibody with a Human IgG1 Fc" J Immunol 164(8):4178-4184 (2000).
International Preliminary Report on Patentability for International Patent Application No. PCT/EP2013/056970 dated Oct. 7, 2014.
Johne et al., "Epitope mapping and binding kinetics of monoclonal antibodies studies by real time biospecific interaction analysis using suface plasmon resonance" J Immunol Methods 160:191-198 (1993).
Johnson et al., "Kabat Database and its applications: 30 years after the first variability plot" Nucleic Acids Res 28(1):214-218 (2000).
Kaufman, R., "Overview of vector design for mammalian gene expression" J Mol Biotechnol 16:151-161 (2000).
Komiyama et al., "IL-17 plays an important role in the development of experimental autoimmune encephalomyelitis" J Immunol 177:566-573 (2006).
Kotake et al., "IL-17 in synovial fluids from patients with rheumatoid arthritis is a potent stimulator of osteoclastogenesis" J Clin Invest 103(9):1345-1352 (1999).
Lukas et al., "Inhibition of C1-mediated immune hemolysis by monomeric and dimeric peptides from the second constant domain of human immunoglobulin G" J Immunol 127(6):2555-2560 (1981).
Lynch et al., "TWEAK induces angiogenesis and proliferation of endothelial cells" J Biol Chem 274(13):8455-8459 (Mar. 26, 1999).
Makrides, S.C., "Components of Vectors for Gene Transfer and Expression in Mammalian Cells" Protein Express Purif 17:183-202 (1999).
Marsters et al., "Identification of a Ligand for the Death-Domain-Containing Receptor Apo3" Curr Biol 8(9):525-528 (1998).

(56) References Cited

OTHER PUBLICATIONS

Matusevicius et al., "Interleukin-17 mRNA expression in blood and CSF mononuclear cells is augmented in multiple sclerosis" Multiple Sclerosis 5:101-104 ( 1999).
Merchant et al., "An efficient route to human bispecific IgG" Nat Biotechnol 16(7):677-681 ( 1998).
Moran et al., "Moran et al., IL-17A upregulates angiogenesis, cytoskeletal rearrangement and cell migration in a chemokine dependent manner, Presentation No. 1157" Abstract Dublin, Ireland, ( Oct. 19, 2009).
Morgan et al., "The N-terminal end of the $C_H2$ domain of chimeric human IgG1 anti-HLa-DR is necessary for C1q, FcγRI and FcγRIII binding" Immunol 86(2):319-324 ( 1995).
Morrison et al., "Chimeric human antibody molecules: Mouse antigen-binding domains with human constant region domains" P Natl Acad Sci USA 81:6851-6855 (Nov. 1984).
Morrison, S., "Two Heads are Better Than One—A new Design for Bispecific Antibodies Enables Effcient Production of Stable Molecules with Good Pharmacodynamic Properties." Nat Biotechnol 25(11):1233-1234 ( 2007).
Muda et al., "Therapeutic assessment of SEED: a new engineered antibody platform designed to generate mono- and bispecific antibodies" Protein Engineering, Design & Selection 24(5):447-454 ( 2011).
Norderhaug et al., "Versatile vectors for transient and stable expression of recombinant antibody molecules in mammalian cells" J Immunol Methods 204:77-87 ( 1997).
Orlandi et al., "Cloning immunoglobulin varible domains for expression by the polymerase chain reaction" P Natl Acad Sci USA 86:3833-3837 ( 1989).
Ridgway et al., "Knobs-into-holes' engineering of antibody CH3 domains for heavy chain heterodimerization" Protein Engineering 9(7):617-621 ( 1996).
Riechmann et al., "Reshaping human antibodies for therapy" Nature 332:323-327 (Mar. 1988).
Rinaldi et al., "Differential expression and functional behaviour of the αv and β3 integrin subunits in cytokine stimulated fibroblast-like cells derived from synovial tissue of rheumatoid arthritis and osteoarthritis in vitro" Ann Rheum Dis 56:729-736 ( 1997).
Sanz et al., "The cytokine TWEAK modulates renal tubulointerstitial inflammation" J Am Soc Nephrol 19:695-703 ( 2008).
Schlaeger et al., "Transient gene expression in mammalian cells grown in serum-free suspension culture" Cytotechnology 30:71-83 ( 1999).
Schlaeger, "The Protein Hydrolysate, Primatone RL, is a Cost-effective Multiple Growth Promoter of Mammalian Cell Culture in Serum-containing and Serum-free Media and Dusplays Anti-apoptosis Properties" J Immunol Methods 194:191-199 ( 1996).
Schwartz et al., "Urinary TWEAK and the activity of lupus nephritis" J Autoimmunity 27:242-250 ( 2006).
Shen et al., "Single variable domain antibody as a versatile buildin block for the construction of IgG-like bespicific antibodies" J Immunol Methods 318:65-74 ( 2007).
Thommesen et al., "Lysine 322 in the human IgG3 C(H)2 domain is crucial for antibody dependent complement activation" Mol Immunol 37(16):995-1004 (Nov. 2000).
van Kuijk et al., "TWEAK and its receptor Fn14 in the synovium of patients with rheumatoid arthritis compared to psoriatic arthritis and its response to tumor necrosis factor blockade" Ann Rheum Dis 69:301-304 ( 2010).
Werner et al., "Appropriate mammalian expression systems for biopharmaceuticals" Arznei-Forschung/Drug Res 48(8):870-880 ( 1998).
Wu et al., "Simultaneous targeting of multiple disease mediators by a dual-variable-domain Immunoglobulin" Nature Biotechnol 25(11):1290-1297 ( 2007).
Yamanishi et al., "Expression and regulation of aggrecanase in arthritis: the role of TGFβ$^1$" J Immunol 168:1405-1412 ( 2002).
Chicheportiche et al., "TWEAK, a new secreted ligand in the tumor necrosis factor family that weakly induces apoptosis" J Biol Chem 272(51):32401-32410 (Dec. 19, 1997).
Chung, A.C.K. et al., "Chemokines in Renal Injury" J Am Soc Nephrol 22:802-809 ( 2011).
Hezareh, M. et al., "Effector function activities of a panel of mutants of a broadly neutralizing antibody against human immunodeficiency virus type 1" J. of Virology 75(24):12161-12168 (2001).
Park, J.-S. et al., "TWEAK promotes the production of Interleukin-17 in rheumatoid arthritis" Cytokine 60:143-149 ( 2012).
Wang, J. et al., "Huperzine A ameliorates experimental autoimmune encephalomyelitis via the suppresion of T cell-mediated neuronal inflammation in mice" Experimental Neurology 236:79-87 ( 2012).
Ziolkowska et al. et al., "High Levels of IL-17 in Rheumatoid Arthritis Patients: IL-15 Triggers In Vitro IL-17 Production Via Cyclosporin A-Sensitive Mechanism" J Immunol 164(5):2832-2838 ( 2000).
He et al., "High-throughput dynamic light scattering method for measuring viscosity of concentrated protein solutions," *Analytical Biochemistry* 399(1):141-143, (2009).
Monkos et al. "Concerntration and temperature dependence of viscosity in lysozume aqueous solutions," *Biochimica et a Biophysica Acta* 1339:304-310 (1997).
Mooney et al., "The viscosity of a concentrated suspension of spherical particles" *J. of Colloid Science* 6(2):162-170 ( 1951).
Neuberger et al. "A hapten-specific chimaeric IgE antibody with human physiological effector function," *Nature* 314:268-270, (1985).
Pace et. al. "How to meaure and predict the moar absorption coefficient of a protein," *Protein Science* 4:2411-1423, (1995).
Schaefer W., et al. "Immunoglobulin domain crossover as a generic approach for the production of bispecific IgG antibodies," *Proc. Natl. Acad Sci. U.S.A.* 108:11187-92, (2011).
International Search Report mailed on Jun. 5, 2013, for PCT Application No. PCT/EP2013/056970, filed on Apr. 3, 2013, 6 pages.
Written Opinion mailed on Jun. 5, 2013, for PCT Application No. PCT/EP2013/056970, filed on Apr. 3, 2013, 6 pages.

\* cited by examiner

SEQUENCE LISTING

<160> NUMBER OF SEQ ID NOS: 100

<210> SEQ ID NO 1
<211> LENGTH: 7
<212> TYPE: PRT
<213> ORGANISM: Oryctolagus cuniculus

<400> SEQUENCE: 1

```
Phe Thr Phe Asn Ala Asn Tyr
  1               5

<210> SEQ ID NO 2
<211> LENGTH: 6
<212> TYPE: PRT
<213> ORGANISM: Oryctolagus cuniculus

<400> SEQUENCE: 2

Tyr Gly Gly Gly Asn Ser
  1               5

<210> SEQ ID NO 3
<211> LENGTH: 7
<212> TYPE: PRT
<213> ORGANISM: Oryctolagus cuniculus

<400> SEQUENCE: 3

Gly Pro Ile Ser Arg Asp Leu
  1               5

<210> SEQ ID NO 4
<211> LENGTH: 11
<212> TYPE: PRT
<213> ORGANISM: Oryctolagus cuniculus

<400> SEQUENCE: 4

Gln Ala Ser Gln Ser Ile Tyr Ser Ser Leu Ala
  1               5                  10

<210> SEQ ID NO 5
<211> LENGTH: 7
<212> TYPE: PRT
<213> ORGANISM: Oryctolagus cuniculus

<400> SEQUENCE: 5

Asp Ala Phe Asp Leu Ala Ser
  1               5

<210> SEQ ID NO 6
<211> LENGTH: 13
<212> TYPE: PRT
<213> ORGANISM: Oryctolagus cuniculus

<400> SEQUENCE: 6

Gln Ser Thr Asp Tyr Gly Asn Ser Trp Asp Gly Asn Pro
  1               5                  10

<210> SEQ ID NO 7
<211> LENGTH: 116
<212> TYPE: PRT
<213> ORGANISM: Oryctolagus cuniculus

<400> SEQUENCE: 7

Gln Ser Leu Glu Glu Ser Gly Gly Gly Leu Val Lys Pro Gly Ala Ser
  1               5                  10                  15

Leu Thr Leu Thr Cys Thr Ala Ser Gly Phe Thr Phe Asn Ala Asn Tyr
             20                  25                  30

Trp Ile Cys Trp Val Arg Gln Ala Pro Gly Lys Gly Leu Glu Trp Ile
         35                  40                  45

Ala Cys Ile Tyr Gly Gly Gly Asn Ser Gly Ala Tyr Tyr Ala Ser Trp
     50                  55                  60

Ala Thr Gly Arg Phe Thr Ile Ser Arg Thr Ser Ser Thr Thr Val Thr
```

```
                65                  70                  75                  80
Leu Gln Met Thr Ser Leu Thr Ala Ala Asp Thr Ala Thr Tyr Phe Cys
                    85                  90                  95

Ala Arg Gly Pro Ile Ser Arg Asp Leu Trp Gly Pro Gly Thr Leu Val
            100                 105                 110

Thr Val Ser Leu
        115

<210> SEQ ID NO 8
<211> LENGTH: 111
<212> TYPE: PRT
<213> ORGANISM: Oryctolagus cuniculus

<400> SEQUENCE: 8

Asp Val Val Met Thr Gln Thr Pro Ala Ser Val Ser Glu Pro Val Gly
1               5                   10                  15

Gly Thr Val Thr Ile Lys Cys Gln Ala Ser Gln Ser Ile Tyr Ser Ser
            20                  25                  30

Leu Ala Trp Tyr Gln Gln Lys Pro Gly Gln Pro Pro Lys Leu Leu Ile
        35                  40                  45

Tyr Asp Ala Phe Asp Leu Ala Ser Gly Val Ser Ser Arg Phe Thr Gly
    50                  55                  60

Ser Gly Ser Gly Thr Gln Phe Thr Leu Thr Ile Ser Asp Leu Glu Cys
65                  70                  75                  80

Ala Asp Ala Ala Thr Tyr Tyr Cys Gln Ser Thr Asp Tyr Gly Asn Ser
                85                  90                  95

Trp Asp Gly Asn Pro Phe Gly Gly Gly Thr Glu Val Val Val Thr
            100                 105                 110

<210> SEQ ID NO 9
<211> LENGTH: 7
<212> TYPE: PRT
<213> ORGANISM: Oryctolagus cuniculus

<400> SEQUENCE: 9

Phe Ser Phe Ser Ser Thr Tyr
1               5

<210> SEQ ID NO 10
<211> LENGTH: 6
<212> TYPE: PRT
<213> ORGANISM: Oryctolagus cuniculus

<400> SEQUENCE: 10

Tyr Val Gly Ser Ser Gly
1               5

<210> SEQ ID NO 11
<211> LENGTH: 7
<212> TYPE: PRT
<213> ORGANISM: Oryctolagus cuniculus

<400> SEQUENCE: 11

Ser Val His Phe Gly Asp Leu
1               5

<210> SEQ ID NO 12
<211> LENGTH: 11
<212> TYPE: PRT
<213> ORGANISM: Oryctolagus cuniculus
```

```
<400> SEQUENCE: 12

Gln Ala Ser Gln Ser Ile Gly Asn Asp Leu Ser
1               5                   10

<210> SEQ ID NO 13
<211> LENGTH: 7
<212> TYPE: PRT
<213> ORGANISM: Oryctolagus cuniculus

<400> SEQUENCE: 13

Ser Val Ser Thr Leu Ala Ser
1               5

<210> SEQ ID NO 14
<211> LENGTH: 13
<212> TYPE: PRT
<213> ORGANISM: Oryctolagus cuniculus

<400> SEQUENCE: 14

Gln Cys Ile Asp Tyr Gly Asn Asn Tyr Val Gly Asn Thr
1               5                   10

<210> SEQ ID NO 15
<211> LENGTH: 116
<212> TYPE: PRT
<213> ORGANISM: Oryctolagus cuniculus

<400> SEQUENCE: 15

Gln Ser Leu Glu Glu Ser Gly Gly Asp Leu Val Lys Pro Gly Ala Ser
1               5                   10                  15

Leu Thr Leu Thr Cys Lys Ala Ser Gly Phe Ser Phe Ser Ser Thr Tyr
            20                  25                  30

Tyr Met Cys Trp Val Arg Gln Ala Pro Gly Lys Gly Leu Glu Trp Ile
        35                  40                  45

Gly Cys Ile Tyr Val Gly Ser Ser Gly Ala Pro Tyr Tyr Ala Ser Trp
    50                  55                  60

Ala Lys Gly Arg Phe Thr Ile Ser Lys Thr Ser Ser Thr Thr Val Ala
65                  70                  75                  80

Leu Gln Met Thr Ser Leu Thr Pro Ala Asp Thr Ala Thr Tyr Val Cys
                85                  90                  95

Thr Arg Ser Val His Phe Gly Asp Leu Trp Gly Pro Gly Thr Leu Val
            100                 105                 110

Thr Val Ser Ser
        115

<210> SEQ ID NO 16
<211> LENGTH: 111
<212> TYPE: PRT
<213> ORGANISM: Oryctolagus cuniculus

<400> SEQUENCE: 16

Asp Val Val Met Thr Gln Thr Pro Ser Pro Val Ser Ala Ala Val Gly
1               5                   10                  15

Gly Thr Val Thr Ile Lys Cys Gln Ala Ser Gln Ser Ile Gly Asn Asp
            20                  25                  30

Leu Ser Trp Tyr Gln Gln Lys Pro Gly Gln Arg Pro Lys Leu Leu Ile
        35                  40                  45

Tyr Ser Val Ser Thr Leu Ala Ser Gly Val Pro Ser Arg Phe Lys Gly
    50                  55                  60
```

```
Ser Gly Ser Gly Thr Glu Tyr Ser Leu Thr Ile Ser Asp Val Gln Cys
 65                  70                  75                  80

Ala Asp Ala Ala Thr Tyr Tyr Cys Gln Cys Ile Asp Tyr Gly Asn Asn
                 85                  90                  95

Tyr Val Gly Asn Thr Phe Gly Gly Gly Thr Glu Val Val Val Lys
            100                 105                 110

<210> SEQ ID NO 17
<211> LENGTH: 7
<212> TYPE: PRT
<213> ORGANISM: Oryctolagus cuniculus

<400> SEQUENCE: 17

Gly Phe Asp Phe Ser Thr Tyr
1               5

<210> SEQ ID NO 18
<211> LENGTH: 6
<212> TYPE: PRT
<213> ORGANISM: Oryctolagus cuniculus

<400> SEQUENCE: 18

Tyr Val Arg Gln Gly Thr
1               5

<210> SEQ ID NO 19
<211> LENGTH: 11
<212> TYPE: PRT
<213> ORGANISM: Oryctolagus cuniculus

<400> SEQUENCE: 19

Gly Gly Tyr Asn Tyr Asp Asp Ala Phe Val Ile
1               5                   10

<210> SEQ ID NO 20
<211> LENGTH: 11
<212> TYPE: PRT
<213> ORGANISM: Oryctolagus cuniculus

<400> SEQUENCE: 20

Gln Ala Ser Gln Asn Ile Tyr Ser Asn Leu Ala
1               5                   10

<210> SEQ ID NO 21
<211> LENGTH: 7
<212> TYPE: PRT
<213> ORGANISM: Oryctolagus cuniculus

<400> SEQUENCE: 21

Thr Ala Ser Tyr Leu Ala Ser
1               5

<210> SEQ ID NO 22
<211> LENGTH: 13
<212> TYPE: PRT
<213> ORGANISM: Oryctolagus cuniculus

<400> SEQUENCE: 22

Gln Thr Ala Tyr Tyr Asn Ser Arg Pro Asp Thr Val Ala
1               5                   10

<210> SEQ ID NO 23
<211> LENGTH: 120
<212> TYPE: PRT
```

<213> ORGANISM: Oryctolagus cuniculus

<400> SEQUENCE: 23

Gln Glu Gln Leu Val Glu Ser Gly Gly Gly Leu Val Gln Pro Gly Gly
1               5                   10                  15

Ser Leu Thr Leu Ser Cys Lys Ala Ser Gly Phe Asp Phe Ser Thr Tyr
            20                  25                  30

Tyr Met Ser Trp Val Arg Gln Ala Pro Gly Lys Gly Leu Glu Trp Ile
        35                  40                  45

Gly Thr Val Tyr Val Arg Gln Gly Thr Thr Tyr Tyr Ala Ser Trp Leu
    50                  55                  60

Asn Gly Arg Phe Thr Ile Ser Ser Asp Asn Ala Gln Asn Thr Val Asp
65                  70                  75                  80

Leu Lys Met Asn Ser Leu Thr Ala Ala Asp Thr Ala Thr Tyr Phe Cys
                85                  90                  95

Ala Lys Gly Gly Tyr Asn Tyr Asp Asp Ala Phe Val Ile Trp Gly Pro
            100                 105                 110

Gly Thr Leu Val Thr Val Ser Phe
        115                 120

<210> SEQ ID NO 24
<211> LENGTH: 111
<212> TYPE: PRT
<213> ORGANISM: Oryctolagus cuniculus

<400> SEQUENCE: 24

Ala Ile Glu Met Thr Gln Thr Pro Phe Ser Val Ser Ala Ala Val Gly
1               5                   10                  15

Gly Thr Val Thr Ile Asn Cys Gln Ala Ser Gln Asn Ile Tyr Ser Asn
            20                  25                  30

Leu Ala Trp Tyr Gln Gln Lys Pro Gly Gln Pro Pro Lys Leu Leu Met
        35                  40                  45

Tyr Thr Ala Ser Tyr Leu Ala Ser Gly Val Pro Ser Arg Phe Lys Gly
    50                  55                  60

Ser Gly Ser Arg Thr Glu Tyr Thr Leu Thr Ile Ser Gly Val Gln Cys
65                  70                  75                  80

Ala Asp Ala Ala Thr Tyr Tyr Cys Gln Thr Ala Tyr Tyr Asn Ser Arg
                85                  90                  95

Pro Asp Thr Val Ala Phe Gly Gly Gly Thr Glu Val Val Val Lys
            100                 105                 110

<210> SEQ ID NO 25
<211> LENGTH: 120
<212> TYPE: PRT
<213> ORGANISM: Artificial
<220> FEATURE:
<223> OTHER INFORMATION: Humanized variant of VH, <TWEAK>305-HC1

<400> SEQUENCE: 25

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asp Phe Ser Thr Tyr
            20                  25                  30

Tyr Met Ser Trp Val Arg Gln Ala Pro Gly Lys Gly Leu Glu Trp Val
        35                  40                  45

Ser Thr Val Tyr Val Arg Gln Gly Thr Thr Tyr Tyr Ala Ser Trp Leu
    50                  55                  60

```
Asn Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Gly Gly Tyr Asn Tyr Asp Asp Ala Phe Val Ile Trp Gly Gln
            100                 105                 110

Gly Thr Leu Val Thr Val Ser Ser
            115                 120

<210> SEQ ID NO 26
<211> LENGTH: 120
<212> TYPE: PRT
<213> ORGANISM: Artificial
<220> FEATURE:
<223> OTHER INFORMATION: Humanized variant of VH, <TWEAK>305-HC2

<400> SEQUENCE: 26

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Asp Phe Ser Thr Tyr
                20                  25                  30

Tyr Met Ser Trp Val Arg Gln Ala Pro Gly Lys Gly Leu Glu Trp Val
            35                  40                  45

Ser Thr Val Tyr Val Arg Gln Gly Thr Thr Tyr Tyr Ala Ser Trp Leu
 50                  55                  60

Asn Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Gly Gly Tyr Asn Tyr Asp Asp Ala Phe Val Ile Trp Gly Gln
            100                 105                 110

Gly Thr Leu Val Thr Val Ser Ser
            115                 120

<210> SEQ ID NO 27
<211> LENGTH: 120
<212> TYPE: PRT
<213> ORGANISM: Artificial
<220> FEATURE:
<223> OTHER INFORMATION: Humanized variant of VH, <TWEAK>305-HC3

<400> SEQUENCE: 27

Gln Val Gln Leu Val Gln Ser Gly Ser Glu Leu Lys Lys Pro Gly Ala
1               5                   10                  15

Ser Val Lys Val Ser Cys Lys Ala Ser Gly Phe Asp Phe Ser Thr Tyr
                20                  25                  30

Tyr Met Ser Trp Val Arg Gln Ala Pro Gly Gln Gly Leu Glu Trp Met
            35                  40                  45

Gly Thr Val Tyr Val Arg Gln Gly Thr Thr Tyr Tyr Ala Ser Trp Leu
 50                  55                  60

Asn Gly Arg Phe Val Phe Ser Leu Asp Thr Ser Val Ser Thr Ala Tyr
 65                  70                  75                  80

Leu Gln Ile Cys Ser Leu Lys Ala Glu Asp Thr Ala Val Tyr Tyr Cys
                 85                  90                  95

Ala Arg Gly Gly Tyr Asn Tyr Asp Asp Ala Phe Val Ile Trp Gly Gln
            100                 105                 110

Gly Thr Leu Val Thr Val Ser Ser
            115                 120
```

<210> SEQ ID NO 28
<211> LENGTH: 120
<212> TYPE: PRT
<213> ORGANISM: Artificial
<220> FEATURE:
<223> OTHER INFORMATION: Humanized variant of VH, <TWEAK>305-HC4

<400> SEQUENCE: 28

Gln Val Gln Leu Val Gln Ser Gly Ala Glu Val Lys Lys Pro Gly Ser
1               5                   10                  15

Ser Val Lys Val Ser Cys Lys Ala Ser Gly Phe Asp Phe Ser Thr Tyr
            20                  25                  30

Tyr Met Ser Trp Val Arg Gln Ala Pro Gly Gln Gly Leu Glu Trp Met
        35                  40                  45

Gly Thr Val Tyr Val Arg Gln Gly Thr Thr Tyr Tyr Ala Ser Trp Leu
    50                  55                  60

Asn Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Tyr Asn Tyr Asp Asp Ala Phe Val Ile Trp Gly Gln
            100                 105                 110

Gly Thr Leu Val Thr Val Ser Ser
        115                 120

<210> SEQ ID NO 29
<211> LENGTH: 120
<212> TYPE: PRT
<213> ORGANISM: Artificial
<220> FEATURE:
<223> OTHER INFORMATION: Humanized variant of VH, <TWEAK>305-HC5

<400> SEQUENCE: 29

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asp Phe Ser Thr Tyr
            20                  25                  30

Tyr Met Ser Trp Val Arg Gln Ala Pro Gly Lys Gly Leu Glu Trp Val
        35                  40                  45

Ser Thr Val Tyr Val Arg Gln Gly Thr Thr Tyr Tyr Ala Ser Trp Leu
    50                  55                  60

Asn Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Tyr Asn Tyr Asp Asp Ala Phe Val Ile Trp Gly Gln
            100                 105                 110

Gly Thr Leu Val Thr Val Ser Ser
        115                 120

<210> SEQ ID NO 30
<211> LENGTH: 120
<212> TYPE: PRT
<213> ORGANISM: Artificial
<220> FEATURE:
<223> OTHER INFORMATION: Humanized variant of VH, <TWEAK> 305-HC6

<400> SEQUENCE: 30

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Asp Phe Ser Thr Tyr
            20                  25                  30

Tyr Met Ser Trp Val Arg Gln Ala Pro Gly Lys Gly Leu Glu Trp Val
        35                  40                  45

Ser Thr Val Tyr Val Arg Gln Gly Thr Thr Tyr Tyr Ala Ser Trp Leu
    50                  55                  60

Asn Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Lys Gly Gly Tyr Asn Tyr Asp Asp Ala Phe Val Ile Trp Gly Gln
            100                 105                 110

Gly Thr Leu Val Thr Val Ser Ser
            115                 120

<210> SEQ ID NO 31
<211> LENGTH: 120
<212> TYPE: PRT
<213> ORGANISM: Artificial
<220> FEATURE:
<223> OTHER INFORMATION: Humanized variant of VH, <TWEAK>305-HC7

<400> SEQUENCE: 31

Glu Val Gln Leu Leu Glu Ser Gly Gly Gly Leu Val Gln Pro Gly Gly
1               5                   10                  15

Ser Leu Thr Leu Ser Cys Ala Ala Ser Gly Phe Asp Phe Ser Thr Tyr
            20                  25                  30

Tyr Met Ser Trp Val Arg Gln Ala Pro Gly Lys Gly Leu Glu Trp Val
        35                  40                  45

Ser Thr Val Tyr Val Arg Gln Gly Thr Thr Tyr Tyr Ala Ser Trp Leu
    50                  55                  60

Asn Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Lys Gly Gly Tyr Asn Tyr Asp Asp Ala Phe Val Ile Trp Gly Gln
            100                 105                 110

Gly Thr Leu Val Thr Val Ser Ser
            115                 120

<210> SEQ ID NO 32
<211> LENGTH: 120
<212> TYPE: PRT
<213> ORGANISM: Artificial
<220> FEATURE:
<223> OTHER INFORMATION: Humanized variant of VH, <TWEAK>305-HC8

<400> SEQUENCE: 32

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Asp Phe Ser Thr Tyr
            20                  25                  30

Tyr Met Ser Trp Val Arg Gln Ala Pro Gly Lys Gly Leu Glu Trp Val
        35                  40                  45

Ser Thr Val Tyr Val Arg Gln Gly Thr Thr Tyr Tyr Ala Ser Trp Leu
    50                  55                  60

Asn Gly Arg Phe Thr Ile Ser Arg Asp Asn Ser Lys Asn Thr Leu Asp
65                  70                  75                  80

Leu Gln Met Asn Ser Leu Arg Ala Glu Asp Thr Ala Val Tyr Tyr Cys
                85                  90                  95

Ala Lys Gly Gly Tyr Asn Tyr Asp Asp Ala Phe Val Ile Trp Gly Gln
            100                 105                 110

Gly Thr Leu Val Thr Val Ser Ser
        115                 120

<210> SEQ ID NO 33
<211> LENGTH: 120
<212> TYPE: PRT
<213> ORGANISM: Artificial
<220> FEATURE:
<223> OTHER INFORMATION: Humanized variant of VH, <TWEAK> 305-HC9

<400> SEQUENCE: 33

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Asp Phe Ser Thr Tyr
            20                  25                  30

Tyr Met Ser Trp Val Arg Gln Ala Pro Gly Lys Gly Leu Glu Trp Val
        35                  40                  45

Ser Thr Val Tyr Val Arg Gln Gly Thr Thr Tyr Tyr Ala Ser Trp Leu
    50                  55                  60

Asn Gly Arg Phe Thr Ile Ser Arg Asp Asn Ser Lys Asn Thr Leu Tyr
65                  70                  75                  80

Leu Lys Met Asn Ser Leu Arg Ala Glu Asp Thr Ala Val Tyr Tyr Cys
                85                  90                  95

Ala Lys Gly Gly Tyr Asn Tyr Asp Asp Ala Phe Val Ile Trp Gly Gln
            100                 105                 110

Gly Thr Leu Val Thr Val Ser Ser
        115                 120

<210> SEQ ID NO 34
<211> LENGTH: 120
<212> TYPE: PRT
<213> ORGANISM: Artificial
<220> FEATURE:
<223> OTHER INFORMATION: Humanized variant of VH, <TWEAK>305-HC10

<400> SEQUENCE: 34

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Asp Phe Ser Thr Tyr
            20                  25                  30

Tyr Met Ser Trp Val Arg Gln Ala Pro Gly Lys Gly Leu Glu Trp Val
        35                  40                  45

Ser Thr Val Tyr Val Arg Gln Gly Thr Thr Tyr Tyr Ala Ser Trp Leu
    50                  55                  60

Asn Gly Arg Phe Thr Ile Ser Arg Asp Asn Ser Lys Asn Thr Leu Tyr
65                  70                  75                  80

Leu Gln Met Asn Ser Leu Thr Ala Glu Asp Thr Ala Val Tyr Tyr Cys
                85                  90                  95

Ala Lys Gly Gly Tyr Asn Tyr Asp Asp Ala Phe Val Ile Trp Gly Gln
            100                 105                 110

Gly Thr Leu Val Thr Val Ser Ser

<210> SEQ ID NO 35
<211> LENGTH: 120
<212> TYPE: PRT
<213> ORGANISM: Artificial
<220> FEATURE:
<223> OTHER INFORMATION: Humanized variant of VH, <TWEAK>305-HC11

<400> SEQUENCE: 35

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Asp Phe Ser Thr Tyr
            20                  25                  30

Tyr Met Ser Trp Val Arg Gln Ala Pro Gly Lys Gly Leu Glu Trp Val
        35                  40                  45

Ser Thr Val Tyr Val Arg Gln Gly Thr Thr Tyr Tyr Ala Ser Trp Leu
    50                  55                  60

Asn Gly Arg Phe Thr Ile Ser Arg Asp Asn Ser Lys Asn Thr Leu Tyr
65                  70                  75                  80

Leu Gln Met Asn Ser Leu Arg Ala Ala Asp Thr Ala Val Tyr Tyr Cys
                85                  90                  95

Ala Lys Gly Gly Tyr Asn Tyr Asp Asp Ala Phe Val Ile Trp Gly Gln
            100                 105                 110

Gly Thr Leu Val Thr Val Ser Ser
        115                 120
```

<210> SEQ ID NO 36
<211> LENGTH: 111
<212> TYPE: PRT
<213> ORGANISM: Artificial
<220> FEATURE:
<223> OTHER INFORMATION: Humanized variant of VL, <TWEAK> 305-LC1

<400> SEQUENCE: 36

```
Asp Ile Gln Met Thr Gln Ser Pro Ser Ser Val Ser Ala Ser Val Gly
1               5                   10                  15

Asp Arg Val Thr Ile Thr Cys Gln Ala Ser Gln Asn Ile Tyr Ser Asn
            20                  25                  30

Leu Ala Trp Tyr Gln Gln Lys Pro Gly Lys Ala Pro Lys Leu Leu Ile
        35                  40                  45

Tyr Thr Ala Ser Tyr Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Thr Ala Tyr Tyr Asn Ser Arg
                85                  90                  95

Pro Asp Thr Val Ala Phe Gly Gly Gly Thr Lys Val Glu Ile Lys
            100                 105                 110
```

<210> SEQ ID NO 37
<211> LENGTH: 111
<212> TYPE: PRT
<213> ORGANISM: Artificial
<220> FEATURE:
<223> OTHER INFORMATION: Humanized variant of VL, <TWEAK> 305-LC2

<400> SEQUENCE: 37

```
Asp Ile Gln Met Thr Gln Ser Pro Ser Ser Val Ser Ala Ser Val Gly
1               5                   10                  15
```

```
Asp Arg Val Thr Ile Thr Cys Gln Ala Ser Gln Asn Ile Tyr Ser Asn
            20                  25                  30

Leu Ala Trp Tyr Gln Gln Lys Pro Gly Lys Ala Pro Lys Leu Leu Ile
        35                  40                  45

Tyr Thr Ala Ser Tyr Leu Ala Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Thr Ala Tyr Tyr Asn Ser Arg
                85                  90                  95

Pro Asp Thr Val Ala Phe Gly Gly Gly Thr Lys Val Glu Ile Lys
            100                 105                 110

<210> SEQ ID NO 38
<211> LENGTH: 111
<212> TYPE: PRT
<213> ORGANISM: Artificial
<220> FEATURE:
<223> OTHER INFORMATION: Humanized variant of VL, <TWEAK> 305-LC3

<400> SEQUENCE: 38

Ala Ile Arg Met Thr Gln Ser Pro Ser Ser Phe Ser Ala Ser Thr Gly
1               5                   10                  15

Asp Arg Val Thr Ile Thr Cys Gln Ala Ser Gln Asn Ile Tyr Ser Asn
            20                  25                  30

Leu Ala Trp Tyr Gln Gln Lys Pro Gly Lys Ala Pro Lys Leu Leu Ile
        35                  40                  45

Tyr Thr Ala Ser Tyr Leu Ala Ser Gly Val Pro Ser Arg Phe Ser Gly
    50                  55                  60

Ser Gly Ser Gly Thr Asp Phe Thr Leu Thr Ile Ser Cys Leu Gln Ser
65                  70                  75                  80

Glu Asp Phe Ala Thr Tyr Tyr Cys Gln Thr Ala Tyr Tyr Asn Ser Arg
                85                  90                  95

Pro Asp Thr Val Ala Phe Gly Gly Gly Thr Lys Val Glu Ile Lys
            100                 105                 110

<210> SEQ ID NO 39
<211> LENGTH: 111
<212> TYPE: PRT
<213> ORGANISM: Artificial
<220> FEATURE:
<223> OTHER INFORMATION: Humanized variant of VL, <TWEAK> 305-LC4

<400> SEQUENCE: 39

Ala Ile Arg Met Thr Gln Ser Pro Ser Ser Phe Ser Ala Ser Thr Gly
1               5                   10                  15

Asp Arg Val Thr Ile Thr Cys Gln Ala Ser Gln Asn Ile Tyr Ser Asn
            20                  25                  30

Leu Ala Trp Tyr Gln Gln Lys Pro Gly Lys Ala Pro Lys Leu Leu Ile
        35                  40                  45

Tyr Thr Ala Ser Tyr Leu Ala Ser Gly Val Pro Ser Arg Phe Ser Gly
    50                  55                  60

Ser Gly Ser Gly Thr Asp Tyr Thr Leu Thr Ile Ser Cys Leu Gln Ser
65                  70                  75                  80

Glu Asp Phe Ala Thr Tyr Tyr Cys Gln Thr Ala Tyr Tyr Asn Ser Arg
                85                  90                  95

Pro Asp Thr Val Ala Phe Gly Gly Gly Thr Lys Val Glu Ile Lys
```

-continued

```
                100                 105                 110

<210> SEQ ID NO 40
<211> LENGTH: 111
<212> TYPE: PRT
<213> ORGANISM: Artificial
<220> FEATURE:
<223> OTHER INFORMATION: Humanized variant of VL, <TWEAK> 305-LC5

<400> SEQUENCE: 40

Asp Ile Gln Met Thr Gln Ser Pro Ser Thr Leu Ser Ala Ser Val Gly
1               5                   10                  15

Asp Arg Val Thr Ile Thr Cys Gln Ala Ser Gln Asn Ile Tyr Ser Asn
            20                  25                  30

Leu Ala Trp Tyr Gln Gln Lys Pro Gly Lys Ala Pro Lys Leu Leu Ile
        35                  40                  45

Tyr Thr Ala Ser Tyr Leu Ala Ser Gly Val Pro Ser Arg Phe Ser Gly
    50                  55                  60

Ser Gly Ser Gly Thr Glu Tyr Thr Leu Thr Ile Ser Ser Leu Gln Pro
65                  70                  75                  80

Asp Asp Phe Ala Thr Tyr Tyr Cys Gln Thr Ala Tyr Tyr Asn Ser Arg
                85                  90                  95

Pro Asp Thr Val Ala Phe Gly Gly Gly Thr Lys Val Glu Ile Lys
            100                 105                 110

<210> SEQ ID NO 41
<211> LENGTH: 111
<212> TYPE: PRT
<213> ORGANISM: Artificial
<220> FEATURE:
<223> OTHER INFORMATION: Humanized variant of VL, <TWEAK> 305-LC6

<400> SEQUENCE: 41

Asp Ile Gln Met Thr Gln Ser Pro Ser Thr Leu Ser Ala Ser Val Gly
1               5                   10                  15

Asp Arg Val Thr Ile Thr Cys Gln Ala Ser Gln Asn Ile Tyr Ser Asn
            20                  25                  30

Leu Ala Trp Tyr Gln Gln Lys Pro Gly Lys Ala Pro Lys Leu Leu Ile
        35                  40                  45

Tyr Thr Ala Ser Tyr Leu Ala Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Thr Ala Tyr Tyr Asn Ser Arg
                85                  90                  95

Pro Asp Thr Val Ala Phe Gly Gly Gly Thr Lys Val Glu Ile Lys
            100                 105                 110

<210> SEQ ID NO 42
<211> LENGTH: 111
<212> TYPE: PRT
<213> ORGANISM: Artificial
<220> FEATURE:
<223> OTHER INFORMATION: Humanized variant of VL, <TWEAK> 305-LC7

<400> SEQUENCE: 42

Asp Ile Gln Met Thr Gln Ser Pro Ser Val Ser Ala Ser Val Gly
1               5                   10                  15

Gly Thr Val Thr Ile Thr Cys Gln Ala Ser Gln Asn Ile Tyr Ser Asn
            20                  25                  30
```

-continued

```
Leu Ala Trp Tyr Gln Gln Lys Pro Gly Lys Ala Pro Lys Leu Leu Ile
            35                  40                  45

Tyr Thr Ala Ser Tyr Leu Ala Ser Gly Val Pro Ser Arg Phe Ser Gly
        50                  55                  60

Ser Gly Ser Gly Thr Asp Tyr Thr Leu Thr Ile Ser Ser Leu Gln Pro
 65                  70                  75                  80

Glu Asp Phe Ala Thr Tyr Tyr Cys Gln Thr Ala Tyr Tyr Asn Ser Arg
                85                  90                  95

Pro Asp Thr Val Ala Phe Gly Gly Gly Thr Lys Val Glu Ile Lys
                100                 105                 110

<210> SEQ ID NO 43
<211> LENGTH: 111
<212> TYPE: PRT
<213> ORGANISM: Artificial
<220> FEATURE:
<223> OTHER INFORMATION: Humanized variant of VL, <TWEAK> 305-LC8

<400> SEQUENCE: 43

Asp Ile Gln Met Thr Gln Ser Pro Ser Ser Val Ser Ala Ser Val Gly
 1               5                  10                  15

Asp Arg Val Thr Ile Asn Cys Gln Ala Ser Gln Asn Ile Tyr Ser Asn
            20                  25                  30

Leu Ala Trp Tyr Gln Gln Lys Pro Gly Lys Ala Pro Lys Leu Leu Ile
            35                  40                  45

Tyr Thr Ala Ser Tyr Leu Ala Ser Gly Val Pro Ser Arg Phe Ser Gly
        50                  55                  60

Ser Gly Ser Gly Thr Asp Tyr Thr Leu Thr Ile Ser Ser Leu Gln Pro
 65                  70                  75                  80

Glu Asp Phe Ala Thr Tyr Tyr Cys Gln Thr Ala Tyr Tyr Asn Ser Arg
                85                  90                  95

Pro Asp Thr Val Ala Phe Gly Gly Gly Thr Lys Val Glu Ile Lys
                100                 105                 110

<210> SEQ ID NO 44
<211> LENGTH: 111
<212> TYPE: PRT
<213> ORGANISM: Artificial
<220> FEATURE:
<223> OTHER INFORMATION: Humanized variant of VL, <TWEAK> 305-LC9

<400> SEQUENCE: 44

Asp Ile Gln Met Thr Gln Ser Pro Ser Ser Val Ser Ala Ser Val Gly
 1               5                  10                  15

Asp Arg Val Thr Ile Thr Cys Gln Ala Ser Gln Asn Ile Tyr Ser Asn
            20                  25                  30

Leu Ala Trp Tyr Gln Gln Lys Pro Gly Gln Pro Pro Lys Leu Leu Ile
            35                  40                  45

Tyr Thr Ala Ser Tyr Leu Ala Ser Gly Val Pro Ser Arg Phe Ser Gly
        50                  55                  60

Ser Gly Ser Gly Thr Asp Tyr Thr Leu Thr Ile Ser Ser Leu Gln Pro
 65                  70                  75                  80

Glu Asp Phe Ala Thr Tyr Tyr Cys Gln Thr Ala Tyr Tyr Asn Ser Arg
                85                  90                  95

Pro Asp Thr Val Ala Phe Gly Gly Gly Thr Lys Val Glu Ile Lys
                100                 105                 110
```

<210> SEQ ID NO 45
<211> LENGTH: 111
<212> TYPE: PRT
<213> ORGANISM: Artificial
<220> FEATURE:
<223> OTHER INFORMATION: Humanized variant of VL, <TWEAK> 05-LC10

<400> SEQUENCE: 45

Asp Ile Gln Met Thr Gln Ser Pro Ser Ser Val Ser Ala Ser Val Gly
1               5                   10                  15

Asp Arg Val Thr Ile Thr Cys Gln Ala Ser Gln Asn Ile Tyr Ser Asn
            20                  25                  30

Leu Ala Trp Tyr Gln Gln Lys Pro Gly Lys Ala Pro Lys Leu Leu Ile
        35                  40                  45

Tyr Thr Ala Ser Tyr Leu Ala Ser Gly Val Pro Ser Arg Phe Lys Gly
    50                  55                  60

Ser Gly Ser Arg Thr Asp Tyr Thr Leu Thr Ile Ser Ser Leu Gln Pro
65                  70                  75                  80

Glu Asp Phe Ala Thr Tyr Tyr Cys Gln Thr Ala Tyr Tyr Asn Ser Arg
                85                  90                  95

Pro Asp Thr Val Ala Phe Gly Gly Gly Thr Lys Val Glu Ile Lys
            100                 105                 110

<210> SEQ ID NO 46
<211> LENGTH: 111
<212> TYPE: PRT
<213> ORGANISM: Artificial
<220> FEATURE:
<223> OTHER INFORMATION: Humanized variant of VL, <TWEAK> 305-LC11

<400> SEQUENCE: 46

Asp Ile Gln Met Thr Gln Ser Pro Ser Ser Val Ser Ala Ser Val Gly
1               5                   10                  15

Asp Arg Val Thr Ile Thr Cys Gln Ala Ser Gln Asn Ile Tyr Ser Asn
            20                  25                  30

Leu Ala Trp Tyr Gln Gln Lys Pro Gly Lys Ala Pro Lys Leu Leu Ile
        35                  40                  45

Tyr Thr Ala Ser Tyr Leu Ala Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Ala Asp Ala Ala Thr Tyr Tyr Cys Gln Thr Ala Tyr Tyr Asn Ser Arg
                85                  90                  95

Pro Asp Thr Val Ala Phe Gly Gly Gly Thr Lys Val Glu Ile Lys
            100                 105                 110

<210> SEQ ID NO 47
<211> LENGTH: 5
<212> TYPE: PRT
<213> ORGANISM: mus musculus

<400> SEQUENCE: 47

Ser Tyr Gly Val His
1               5

<210> SEQ ID NO 48
<211> LENGTH: 16
<212> TYPE: PRT
<213> ORGANISM: mus musculus

<400> SEQUENCE: 48

```
Val Ile Trp Ser Asp Gly Thr Thr Thr Tyr Asn Ser Ala Leu Lys Ser
1               5                   10                  15
```

<210> SEQ ID NO 49
<211> LENGTH: 13
<212> TYPE: PRT
<213> ORGANISM: mus musculus

<400> SEQUENCE: 49

```
Asp Thr His Tyr Arg Leu Tyr Tyr Tyr Ala Met Asp Tyr
1               5                   10
```

<210> SEQ ID NO 50
<211> LENGTH: 16
<212> TYPE: PRT
<213> ORGANISM: mus musculus

<400> SEQUENCE: 50

```
Arg Ser Ser Gln Ser Leu Val His Ser Asn Gly Asp Thr Tyr Phe His
1               5                   10                  15
```

<210> SEQ ID NO 51
<211> LENGTH: 7
<212> TYPE: PRT
<213> ORGANISM: mus musculus

<400> SEQUENCE: 51

```
Lys Val Ser Asn Arg Phe Ser
1               5
```

<210> SEQ ID NO 52
<211> LENGTH: 9
<212> TYPE: PRT
<213> ORGANISM: mus musculus

<400> SEQUENCE: 52

```
Ser Gln Thr Thr His Ala Pro Phe Thr
1               5
```

<210> SEQ ID NO 53
<211> LENGTH: 121
<212> TYPE: PRT
<213> ORGANISM: mus musculus

<400> SEQUENCE: 53

```
Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Asp Ser Tyr
            20                  25                  30

Gly Val His Trp Val Arg Gln Pro Pro Gly Lys Gly Leu Glu Trp Leu
        35                  40                  45

Val Val Ile Trp Ser Asp Gly Thr Thr Tyr Asn Ser Ala Leu Lys
    50                  55                  60

Ser Arg Leu Ser Ile Thr Lys Asp Asn Ser Lys Ser Gln Val Phe Leu
65                  70                  75                  80

Lys Met Asn Ser Leu Gln Thr Asp Asp Thr Ala Ile Tyr Tyr Cys Ala
                85                  90                  95

Arg Asp Thr His Tyr Arg Leu Tyr Tyr Tyr Ala Met Asp Tyr Trp Gly
            100                 105                 110

Gln Gly Thr Ser Val Thr Val Ser Ser
        115                 120
```

<210> SEQ ID NO 54
<211> LENGTH: 112
<212> TYPE: PRT
<213> ORGANISM: mus musculus

<400> SEQUENCE: 54

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asp Thr Tyr Phe His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Asn Arg Val Glu Ala Glu Asp Leu Gly Val Tyr Phe Cys Ser Gln Thr
                85                  90                  95

Thr His Ala Pro Phe Thr Phe Gly Ser Gly Thr Lys Leu Glu Ile Lys
            100                 105                 110

<210> SEQ ID NO 55
<211> LENGTH: 121
<212> TYPE: PRT
<213> ORGANISM: Artificial
<220> FEATURE:
<223> OTHER INFORMATION: Humanized variant of VH, <IL17> 9C6-2B6-HC134

<400> SEQUENCE: 55

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Asp Ser Tyr
            20                  25                  30

Gly Val His Trp Val Arg Gln Ala Pro Gly Lys Gly Leu Glu Trp Val
        35                  40                  45

Ser Val Ile Trp Ser Asp Gly Thr Thr Thr Tyr Asn Ser Ala Leu Lys
    50                  55                  60

Ser Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Asp Thr His Tyr Arg Leu Tyr Tyr Tyr Ala Met Asp Tyr Trp Gly
            100                 105                 110

Gln Gly Thr Thr Val Thr Val Ser Ser
        115                 120

<210> SEQ ID NO 56
<211> LENGTH: 121
<212> TYPE: PRT
<213> ORGANISM: Artificial
<220> FEATURE:
<223> OTHER INFORMATION: Humanized variant of VH, <IL17> 9C6-2B6-HC136

<400> SEQUENCE: 56

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Asp Ser Tyr
            20                  25                  30

```
Gly Val His Trp Val Arg Gln Ala Thr Gly Lys Gly Leu Glu Trp Val
            35                  40                  45

Ser Val Ile Trp Ser Asp Gly Thr Thr Thr Tyr Asn Ser Ala Leu Lys
 50                  55                  60

Ser Arg Phe Thr Ile Ser Arg Glu Asn Ala Lys Asn Ser Leu Tyr Leu
 65                  70                  75                  80

Gln Met Asn Ser Leu Arg Ala Gly Asp Thr Ala Val Tyr Tyr Cys Ala
                 85                  90                  95

Arg Asp Thr His Tyr Arg Leu Tyr Tyr Tyr Ala Met Asp Tyr Trp Gly
                100                 105                 110

Gln Gly Thr Thr Val Thr Val Ser Ser
            115                 120

<210> SEQ ID NO 57
<211> LENGTH: 112
<212> TYPE: PRT
<213> ORGANISM: Artificial
<220> FEATURE:
<223> OTHER INFORMATION: Humanized variant of VL, <IL17> 9C6-2B6-LC134

<400> SEQUENCE: 57

Asp Ile Val Met Thr Gln Ser Pro Leu Ser Leu Pro Val Thr Pro Gly
 1               5                  10                  15

Glu Pro Ala Ser Ile Ser Cys Arg Ser Ser Gln Ser Leu Val His Ser
                 20                  25                  30

Asn Gly Asp Thr Tyr Phe His Trp Tyr Leu Gln Lys Pro Gly Gln Ser
            35                  40                  45

Pro Gln Leu Leu Ile Tyr Lys Val Ser Asn Arg Phe Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Ser Gln Thr
                 85                  90                  95

Thr His Ala Pro Phe Thr Phe Gly Gln Gly Thr Lys Leu Glu Ile Lys
                100                 105                 110

<210> SEQ ID NO 58
<211> LENGTH: 112
<212> TYPE: PRT
<213> ORGANISM: Artificial
<220> FEATURE:
<223> OTHER INFORMATION: Humanized variant of VL, <IL17> 9C6-2B6-LC136

<400> SEQUENCE: 58

Asp Ile Val Met Thr Gln Ser Pro Leu Ser Leu Pro Val Thr Pro Gly
 1               5                  10                  15

Glu Pro Ala Ser Ile Ser Cys Arg Ser Ser Gln Ser Leu Val His Ser
                 20                  25                  30

Asn Gly Asp Thr Tyr Phe His Trp Tyr Leu Gln Lys Pro Gly Gln Ser
            35                  40                  45

Pro Gln Leu Leu Ile Tyr Lys Val Ser Asn Arg Phe Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Ser Gln Thr
                 85                  90                  95

Thr His Ala Pro Phe Thr Phe Gly Gln Gly Thr Lys Leu Glu Ile Lys
```

-continued

```
                100                 105                 110
```

<210> SEQ ID NO 59
<211> LENGTH: 107
<212> TYPE: PRT
<213> ORGANISM: homo sapiens

<400> SEQUENCE: 59

```
Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105
```

<210> SEQ ID NO 60
<211> LENGTH: 105
<212> TYPE: PRT
<213> ORGANISM: homo sapiens

<400> SEQUENCE: 60

```
Gln Pro Lys Ala Ala Pro Ser Val Thr Leu Phe Pro Pro Ser Ser Glu
1               5                   10                  15

Glu Leu Gln Ala Asn Lys Ala Thr Leu Val Cys Leu Ile Ser Asp Phe
            20                  25                  30

Tyr Pro Gly Ala Val Thr Val Ala Trp Lys Ala Asp Ser Ser Pro Val
        35                  40                  45

Lys Ala Gly Val Glu Thr Thr Thr Pro Ser Lys Gln Ser Asn Asn Lys
    50                  55                  60

Tyr Ala Ala Ser Ser Tyr Leu Ser Leu Thr Pro Glu Gln Trp Lys Ser
65                  70                  75                  80

His Arg Ser Tyr Ser Cys Gln Val Thr His Glu Gly Ser Thr Val Glu
                85                  90                  95

Lys Thr Val Ala Pro Thr Glu Cys Ser
            100                 105
```

<210> SEQ ID NO 61
<211> LENGTH: 330
<212> TYPE: PRT
<213> ORGANISM: homo sapiens

<400> SEQUENCE: 61

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60
```

```
Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 62
<211> LENGTH: 330
<212> TYPE: PRT
<213> ORGANISM: homo sapiens

<400> SEQUENCE: 62

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
```

```
            100                 105                 110
Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
            210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 63
<211> LENGTH: 330
<212> TYPE: PRT
<213> ORGANISM: homo sapiens

<400> SEQUENCE: 63

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Ala Ala Gly Gly Pro Ser Val Phe Leu Phe Pro Pro
            115                 120                 125

Lys Pro Lys Asp Thr Leu Met Ile Ser Arg Thr Pro Glu Val Thr Cys
            130                 135                 140
```

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
            165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
            210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
            245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 64
<211> LENGTH: 330
<212> TYPE: PRT
<213> ORGANISM: homo sapiens

<400> SEQUENCE: 64

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
            85                  90                  95

Lys Val Glu Pro Lys Ser Cys Asp Lys Thr His Thr Cys Pro Pro Cys
            100                 105                 110

Pro Ala Pro Glu Ala Ala Gly Gly Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
            165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
                195                 200                 205

Lys Ala Leu Gly Ala Pro Ile Glu Lys Thr Ile Ser Lys Ala Lys Gly
            210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
                275                 280                 285

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 65
<211> LENGTH: 327
<212> TYPE: PRT
<213> ORGANISM: homo sapiens

<400> SEQUENCE: 65

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
                100                 105                 110

Glu Phe Leu Gly Gly Pro Ser Val Phe Leu Phe Pro Pro Lys Pro Lys
            115                 120                 125

Asp Thr Leu Met Ile Ser Arg Thr Pro Glu Val Thr Cys Val Val Val
130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys

```
                225                 230                 235                 240
Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
            275                 280                 285

Arg Leu Thr Val Asp Lys Ser Arg Trp Gln Glu Gly Asn Val Phe Ser
            290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 66
<211> LENGTH: 327
<212> TYPE: PRT
<213> ORGANISM: homo sapiens

<400> SEQUENCE: 66

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Glu Gly Gly Pro Ser Val Phe Leu Phe Pro Pro Lys Pro Lys
            115                 120                 125

Asp Thr Leu Met Ile Ser Arg Thr Pro Glu Val Thr Cys Val Val Val
        130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
            195                 200                 205

Pro Ser Ser Ile Glu Lys Thr Ile Ser Lys Ala Lys Gly Gln Pro Arg
        210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270
```

```
Thr Thr Pro Pro Val Leu Asp Ser Asp Gly Ser Phe Phe Leu Tyr Ser
            275                 280                 285

Arg Leu Thr Val Asp Lys Ser Arg Trp Gln Glu Gly Asn Val Phe Ser
290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 67
<211> LENGTH: 327
<212> TYPE: PRT
<213> ORGANISM: homo sapiens

<400> SEQUENCE: 67

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Glu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
290                 295                 300

Cys Ser Val Met His Glu Ala Leu His Asn His Tyr Thr Gln Lys Ser
305                 310                 315                 320
```

```
Leu Ser Leu Ser Leu Gly Lys
            325

<210> SEQ ID NO 68
<211> LENGTH: 249
<212> TYPE: PRT
<213> ORGANISM: Homo sapiens

<400> SEQUENCE: 68

Met Ala Ala Arg Arg Ser Gln Arg Arg Gly Arg Gly Glu Pro
1               5                   10                  15

Gly Thr Ala Leu Leu Val Pro Leu Ala Leu Gly Leu Gly Leu Ala Leu
            20                  25                  30

Ala Cys Leu Gly Leu Leu Leu Ala Val Val Ser Leu Gly Ser Arg Ala
            35                  40                  45

Ser Leu Ser Ala Gln Glu Pro Ala Gln Glu Glu Leu Val Ala Glu Glu
        50                  55                  60

Asp Gln Asp Pro Ser Glu Leu Asn Pro Gln Thr Glu Glu Ser Gln Asp
65                  70                  75                  80

Pro Ala Pro Phe Leu Asn Arg Leu Val Arg Pro Arg Arg Ser Ala Pro
                85                  90                  95

Lys Gly Arg Lys Thr Arg Ala Arg Arg Ala Ile Ala Ala His Tyr Glu
            100                 105                 110

Val His Pro Arg Pro Gly Gln Asp Gly Ala Gln Ala Gly Val Asp Gly
            115                 120                 125

Thr Val Ser Gly Trp Glu Glu Ala Arg Ile Asn Ser Ser Ser Pro Leu
        130                 135                 140

Arg Tyr Asn Arg Gln Ile Gly Glu Phe Ile Val Thr Arg Ala Gly Leu
145                 150                 155                 160

Tyr Tyr Leu Tyr Cys Gln Val His Phe Asp Glu Gly Lys Ala Val Tyr
                165                 170                 175

Leu Lys Leu Asp Leu Leu Val Asp Gly Val Leu Ala Leu Arg Cys Leu
            180                 185                 190

Glu Glu Phe Ser Ala Thr Ala Ala Ser Ser Leu Gly Pro Gln Leu Arg
            195                 200                 205

Leu Cys Gln Val Ser Gly Leu Leu Ala Leu Arg Pro Gly Ser Ser Leu
        210                 215                 220

Arg Ile Arg Thr Leu Pro Trp Ala His Leu Lys Ala Ala Pro Phe Leu
225                 230                 235                 240

Thr Tyr Phe Gly Leu Phe Gln Val His
                245

<210> SEQ ID NO 69
<211> LENGTH: 249
<212> TYPE: PRT
<213> ORGANISM: Mus musculus

<400> SEQUENCE: 69

Met Ala Ala Arg Arg Ser Gln Arg Arg Gly Arg Gly Glu Pro
1               5                   10                  15

Gly Thr Ala Leu Leu Ala Pro Leu Val Leu Ser Leu Gly Leu Ala Leu
            20                  25                  30

Ala Cys Leu Gly Leu Leu Leu Val Val Val Ser Leu Gly Ser Trp Ala
            35                  40                  45

Thr Leu Ser Ala Gln Glu Pro Ser Gln Glu Glu Leu Thr Ala Glu Asp
        50                  55                  60
```

```
Arg Arg Glu Pro Pro Glu Leu Asn Pro Gln Thr Glu Glu Ser Gln Asp
 65                  70                  75                  80

Val Val Pro Phe Leu Glu Gln Leu Val Arg Pro Arg Ser Ala Pro
             85                  90                  95

Lys Gly Arg Lys Ala Arg Pro Arg Arg Ala Ile Ala Ala His Tyr Glu
            100                 105                 110

Val His Pro Arg Pro Gly Gln Asp Gly Ala Gln Ala Gly Val Asp Gly
            115                 120                 125

Thr Val Ser Gly Trp Glu Glu Thr Lys Ile Asn Ser Ser Ser Pro Leu
130                 135                 140

Arg Tyr Asp Arg Gln Ile Gly Glu Phe Thr Val Ile Arg Ala Gly Leu
145                 150                 155                 160

Tyr Tyr Leu Tyr Cys Gln Val His Phe Asp Glu Gly Lys Ala Val Tyr
                165                 170                 175

Leu Lys Leu Asp Leu Leu Val Asn Gly Val Leu Ala Leu Arg Cys Leu
            180                 185                 190

Glu Glu Phe Ser Ala Thr Ala Ala Ser Ser Pro Gly Pro Gln Leu Arg
            195                 200                 205

Leu Cys Gln Val Ser Gly Leu Leu Pro Leu Arg Pro Gly Ser Ser Leu
210                 215                 220

Arg Ile Arg Thr Leu Pro Trp Ala His Leu Lys Ala Ala Pro Phe Leu
225                 230                 235                 240

Thr Tyr Phe Gly Leu Phe Gln Val His
                245

<210> SEQ ID NO 70
<211> LENGTH: 155
<212> TYPE: PRT
<213> ORGANISM: Homo sapiens

<400> SEQUENCE: 70

Met Thr Pro Gly Lys Thr Ser Leu Val Ser Leu Leu Leu Leu Leu Ser
1               5                   10                  15

Leu Glu Ala Ile Val Lys Ala Gly Ile Thr Ile Pro Arg Asn Pro Gly
            20                  25                  30

Cys Pro Asn Ser Glu Asp Lys Asn Phe Pro Arg Thr Val Met Val Asn
            35                  40                  45

Leu Asn Ile His Asn Arg Asn Thr Asn Thr Asn Pro Lys Arg Ser Ser
        50                  55                  60

Asp Tyr Tyr Asn Arg Ser Thr Ser Pro Trp Asn Leu His Arg Asn Glu
65                  70                  75                  80

Asp Pro Glu Arg Tyr Pro Ser Val Ile Trp Glu Ala Lys Cys Arg His
            85                  90                  95

Leu Gly Cys Ile Asn Ala Asp Gly Asn Val Asp Tyr His Met Asn Ser
            100                 105                 110

Val Pro Ile Gln Gln Glu Ile Leu Val Leu Arg Arg Glu Pro Pro His
            115                 120                 125

Cys Pro Asn Ser Phe Arg Leu Glu Lys Ile Leu Val Ser Val Gly Cys
            130                 135                 140

Thr Cys Val Thr Pro Ile Val His His Val Ala
145                 150                 155

<210> SEQ ID NO 71
<211> LENGTH: 180
<212> TYPE: PRT
```

-continued

<213> ORGANISM: Homo Sapiens

<400> SEQUENCE: 71

Met Asp Trp Pro His Asn Leu Leu Phe Leu Leu Thr Ile Ser Ile Phe
1               5                   10                  15

Leu Gly Leu Gly Gln Pro Arg Ser Pro Lys Ser Lys Arg Lys Gly Gln
            20                  25                  30

Gly Arg Pro Gly Pro Leu Ala Pro Gly Pro His Gln Val Pro Leu Asp
        35                  40                  45

Leu Val Ser Arg Met Lys Pro Tyr Ala Arg Met Glu Glu Tyr Glu Arg
    50                  55                  60

Asn Ile Glu Glu Met Val Ala Gln Leu Arg Asn Ser Ser Glu Leu Ala
65                  70                  75                  80

Gln Arg Lys Cys Glu Val Asn Leu Gln Leu Trp Met Ser Asn Lys Arg
                85                  90                  95

Ser Leu Ser Pro Trp Gly Tyr Ser Ile Asn His Asp Pro Ser Arg Ile
            100                 105                 110

Pro Val Asp Leu Pro Glu Ala Arg Cys Leu Cys Leu Gly Cys Val Asn
        115                 120                 125

Pro Phe Thr Met Gln Glu Asp Arg Ser Met Val Ser Val Pro Val Phe
    130                 135                 140

Ser Gln Val Pro Val Arg Arg Arg Leu Cys Pro Pro Pro Pro Arg Thr
145                 150                 155                 160

Gly Pro Cys Arg Gln Arg Ala Val Met Glu Thr Ile Ala Val Gly Cys
                165                 170                 175

Thr Cys Ile Phe
            180

<210> SEQ ID NO 72
<211> LENGTH: 197
<212> TYPE: PRT
<213> ORGANISM: Homo Sapiens

<400> SEQUENCE: 72

Met Thr Leu Leu Pro Gly Leu Leu Phe Leu Thr Trp Leu His Thr Cys
1               5                   10                  15

Leu Ala His His Asp Pro Ser Leu Arg Gly His Pro His Ser His Gly
            20                  25                  30

Thr Pro His Cys Tyr Ser Ala Glu Glu Leu Pro Leu Gly Gln Ala Pro
        35                  40                  45

Pro His Leu Leu Ala Arg Gly Ala Lys Trp Gly Gln Ala Leu Pro Val
    50                  55                  60

Ala Leu Val Ser Ser Leu Glu Ala Ala Ser His Arg Gly Arg His Glu
65                  70                  75                  80

Arg Pro Ser Ala Thr Thr Gln Cys Pro Val Leu Arg Pro Glu Glu Val
                85                  90                  95

Leu Glu Ala Asp Thr His Gln Arg Ser Ile Ser Pro Trp Arg Tyr Arg
            100                 105                 110

Val Asp Thr Asp Glu Asp Arg Tyr Pro Gln Lys Leu Ala Phe Ala Glu
        115                 120                 125

Cys Leu Cys Arg Gly Cys Ile Asp Ala Arg Thr Gly Arg Glu Thr Ala
    130                 135                 140

Ala Leu Asn Ser Val Arg Leu Leu Gln Ser Leu Leu Val Leu Arg Arg
145                 150                 155                 160

Arg Pro Cys Ser Arg Asp Gly Ser Gly Leu Pro Thr Pro Gly Ala Phe

-continued

```
                        165                 170                 175
Ala Phe His Thr Glu Phe Ile His Val Pro Val Gly Cys Thr Cys Val
                180                 185                 190

Leu Pro Arg Ser Val
        195

<210> SEQ ID NO 73
<211> LENGTH: 202
<212> TYPE: PRT
<213> ORGANISM: Homo Sapiens

<400> SEQUENCE: 73

Met Leu Val Ala Gly Phe Leu Ala Leu Pro Pro Ser Trp Ala Ala
1               5                   10                  15

Gly Ala Pro Arg Ala Gly Arg Arg Pro Ala Arg Pro Arg Gly Cys Ala
                20                  25                  30

Asp Arg Pro Glu Glu Leu Leu Glu Gln Leu Tyr Gly Arg Leu Ala Ala
            35                  40                  45

Gly Val Leu Ser Ala Phe His His Thr Leu Gln Leu Gly Pro Arg Glu
    50                  55                  60

Gln Ala Arg Asn Ala Ser Cys Pro Ala Gly Gly Arg Pro Ala Asp Arg
65                  70                  75                  80

Arg Phe Arg Pro Pro Thr Asn Leu Arg Ser Val Ser Pro Trp Ala Tyr
                85                  90                  95

Arg Ile Ser Tyr Asp Pro Ala Arg Tyr Pro Arg Tyr Leu Pro Glu Ala
            100                 105                 110

Tyr Cys Leu Cys Arg Gly Cys Leu Thr Gly Leu Phe Gly Glu Glu Asp
        115                 120                 125

Val Arg Phe Arg Ser Ala Pro Val Tyr Met Pro Thr Val Val Leu Arg
    130                 135                 140

Arg Thr Pro Ala Cys Ala Gly Gly Arg Ser Val Tyr Thr Glu Ala Tyr
145                 150                 155                 160

Val Thr Ile Pro Val Gly Cys Thr Cys Val Pro Glu Pro Glu Lys Asp
                165                 170                 175

Ala Asp Ser Ile Asn Ser Ser Ile Asp Lys Gln Gly Ala Lys Leu Leu
            180                 185                 190

Leu Gly Pro Asn Asp Ala Pro Ala Gly Pro
        195                 200

<210> SEQ ID NO 74
<211> LENGTH: 177
<212> TYPE: PRT
<213> ORGANISM: Homo Sapiens

<400> SEQUENCE: 74

Met Arg Glu Arg Pro Arg Leu Gly Glu Asp Ser Ser Leu Ile Ser Leu
1               5                   10                  15

Phe Leu Gln Val Val Ala Phe Leu Ala Met Val Met Gly Thr His Thr
                20                  25                  30

Tyr Ser His Trp Pro Ser Cys Cys Pro Ser Lys Gly Gln Asp Thr Ser
            35                  40                  45

Glu Glu Leu Leu Arg Trp Ser Thr Val Pro Val Pro Pro Leu Glu Pro
    50                  55                  60

Ala Arg Pro Asn Arg His Pro Glu Ser Cys Arg Ala Ser Glu Asp Gly
65                  70                  75                  80

Pro Leu Asn Ser Arg Ala Ile Ser Pro Trp Arg Tyr Glu Leu Asp Arg
```

```
                         85                  90                  95

Asp Leu Asn Arg Leu Pro Gln Asp Leu Tyr His Ala Arg Cys Leu Cys
                100                 105                 110

Pro His Cys Val Ser Leu Gln Thr Gly Ser His Met Asp Pro Arg Gly
            115                 120                 125

Asn Ser Glu Leu Leu Tyr His Asn Gln Thr Val Phe Tyr Arg Arg Pro
        130                 135                 140

Cys His Gly Glu Lys Gly Thr His Lys Gly Tyr Cys Leu Glu Arg Arg
145                 150                 155                 160

Leu Tyr Arg Val Ser Leu Ala Cys Val Cys Val Arg Pro Arg Val Met
                165                 170                 175

Gly

<210> SEQ ID NO 75
<211> LENGTH: 163
<212> TYPE: PRT
<213> ORGANISM: Homo Sapiens

<400> SEQUENCE: 75

Met Thr Val Lys Thr Leu His Gly Pro Ala Met Val Lys Tyr Leu Leu
1               5                   10                  15

Leu Ser Ile Leu Gly Leu Ala Phe Leu Ser Glu Ala Ala Ala Arg Lys
            20                  25                  30

Ile Pro Lys Val Gly His Thr Phe Phe Gln Lys Pro Glu Ser Cys Pro
        35                  40                  45

Pro Val Pro Gly Gly Ser Met Lys Leu Asp Ile Gly Ile Ile Asn Glu
    50                  55                  60

Asn Gln Arg Val Ser Met Ser Arg Asn Ile Glu Ser Arg Ser Thr Ser
65                  70                  75                  80

Pro Trp Asn Tyr Thr Val Thr Trp Asp Pro Asn Arg Tyr Pro Ser Glu
                85                  90                  95

Val Val Gln Ala Gln Cys Arg Asn Leu Gly Cys Ile Asn Ala Gln Gly
                100                 105                 110

Lys Glu Asp Ile Ser Met Asn Ser Val Pro Ile Gln Gln Glu Thr Leu
            115                 120                 125

Val Val Arg Arg Lys His Gln Gly Cys Ser Val Ser Phe Gln Leu Glu
        130                 135                 140

Lys Val Leu Val Thr Val Gly Cys Thr Cys Val Thr Pro Val Ile His
145                 150                 155                 160

His Val Gln

<210> SEQ ID NO 76
<211> LENGTH: 451
<212> TYPE: PRT
<213> ORGANISM: Artificial
<220> FEATURE:
<223> OTHER INFORMATION: Bispecific <Tweak-IL-17> #2 antibody- heavy
      chain construct 1

<400> SEQUENCE: 76

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Asp Ser Tyr
            20                  25                  30

Gly Val His Trp Val Arg Gln Ala Thr Gly Lys Gly Leu Glu Trp Val
        35                  40                  45
```

```
Ser Val Ile Trp Ser Asp Gly Thr Thr Thr Tyr Asn Ser Ala Leu Lys
 50                  55                  60
Ser Arg Phe Thr Ile Ser Arg Glu Asn Ala Lys Asn Ser Leu Tyr Leu
 65                  70                  75                  80
Gln Met Asn Ser Leu Arg Ala Gly Asp Thr Ala Val Tyr Tyr Cys Ala
                 85                  90                  95
Arg Asp Thr His Tyr Arg Leu Tyr Tyr Tyr Ala Met Asp Tyr Trp Gly
            100                 105                 110
Gln Gly Thr Thr Val Thr Val Ser Ala Ser Thr Lys Gly Pro Ser
            115                 120                 125
Val Phe Pro Leu Ala Pro Ser Ser Lys Ser Thr Ser Gly Gly Thr Ala
130                 135                 140
Ala Leu Gly Cys Leu Val Lys Asp Tyr Phe Pro Glu Pro Val Thr Val
145                 150                 155                 160
Ser Trp Asn Ser Gly Ala Leu Thr Ser Gly Val His Thr Phe Pro Ala
                165                 170                 175
Val Leu Gln Ser Ser Gly Leu Tyr Ser Leu Ser Ser Val Val Thr Val
                180                 185                 190
Pro Ser Ser Ser Leu Gly Thr Gln Thr Tyr Ile Cys Asn Val Asn His
                195                 200                 205
Lys Pro Ser Asn Thr Lys Val Asp Lys Lys Val Glu Pro Lys Ser Cys
210                 215                 220
Asp Lys Thr His Thr Cys Pro Pro Cys Pro Ala Pro Glu Leu Leu Gly
225                 230                 235                 240
Gly Pro Ser Val Phe Leu Phe Pro Pro Lys Pro Lys Asp Thr Leu Met
                245                 250                 255
Ile Ser Arg Thr Pro Glu Val Thr Cys Val Val Val Asp Val Ser His
                260                 265                 270
Glu Asp Pro Glu Val Lys Phe Asn Trp Tyr Val Asp Gly Val Glu Val
            275                 280                 285
His Asn Ala Lys Thr Lys Pro Arg Glu Glu Gln Tyr Asn Ser Thr Tyr
            290                 295                 300
Arg Val Val Ser Val Leu Thr Val Leu His Gln Asp Trp Leu Asn Gly
305                 310                 315                 320
Lys Glu Tyr Lys Cys Lys Val Ser Asn Lys Ala Leu Pro Ala Pro Ile
                325                 330                 335
Glu Lys Thr Ile Ser Lys Ala Lys Gly Gln Pro Arg Glu Pro Gln Val
                340                 345                 350
Cys Thr Leu Pro Pro Ser Arg Asp Glu Leu Thr Lys Asn Gln Val Ser
                355                 360                 365
Leu Ser Cys Ala Val Lys Gly Phe Tyr Pro Ser Asp Ile Ala Val Glu
370                 375                 380
Trp Glu Ser Asn Gly Gln Pro Glu Asn Asn Tyr Lys Thr Thr Pro Pro
385                 390                 395                 400
Val Leu Asp Ser Asp Gly Ser Phe Phe Leu Val Ser Lys Leu Thr Val
                405                 410                 415
Asp Lys Ser Arg Trp Gln Gln Gly Asn Val Phe Ser Cys Ser Val Met
                420                 425                 430
His Glu Ala Leu His Asn His Tyr Thr Gln Lys Ser Leu Ser Leu Ser
            435                 440                 445
Pro Gly Lys
450
```

```
<210> SEQ ID NO 77
<211> LENGTH: 454
<212> TYPE: PRT
<213> ORGANISM: Artificial
<220> FEATURE:
<223> OTHER INFORMATION: Bispecific <Tweak-IL-17> #2 antibody- heavy
      chain construct 2

<400> SEQUENCE: 77

Gln Val Gln Leu Val Gln Ser Gly Ala Glu Val Lys Lys Pro Gly Ser
1               5                   10                  15

Ser Val Lys Val Ser Cys Lys Ala Ser Gly Phe Asp Phe Ser Thr Tyr
            20                  25                  30

Tyr Met Ser Trp Val Arg Gln Ala Pro Gly Gln Gly Leu Glu Trp Met
        35                  40                  45

Gly Thr Val Tyr Val Arg Gln Gly Thr Thr Tyr Tyr Ala Ser Trp Leu
    50                  55                  60

Asn Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Tyr Asn Tyr Asp Asp Ala Phe Val Ile Trp Gly Gln
            100                 105                 110

Gly Thr Leu Val Thr Val Ser Ser Ala Ser Val Ala Ala Pro Ser Val
        115                 120                 125

Phe Ile Phe Pro Pro Ser Asp Glu Gln Leu Lys Ser Gly Thr Ala Ser
    130                 135                 140

Val Val Cys Leu Leu Asn Asn Phe Tyr Pro Arg Glu Ala Lys Val Gln
145                 150                 155                 160

Trp Lys Val Asp Asn Ala Leu Gln Ser Gly Asn Ser Gln Glu Ser Val
                165                 170                 175

Thr Glu Gln Asp Ser Lys Asp Ser Thr Tyr Ser Leu Ser Ser Thr Leu
            180                 185                 190

Thr Leu Ser Lys Ala Asp Tyr Glu Lys His Lys Val Tyr Ala Cys Glu
        195                 200                 205

Val Thr His Gln Gly Leu Ser Ser Pro Val Thr Lys Ser Phe Asn Arg
    210                 215                 220

Gly Glu Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
        275                 280                 285

Val Glu Val His Asn Ala Lys Thr Lys Pro Arg Glu Glu Gln Tyr Asn
    290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
            340                 345                 350

Pro Gln Val Tyr Thr Leu Pro Pro Cys Arg Asp Glu Leu Thr Lys Asn
        355                 360                 365
```

```
Gln Val Ser Leu Trp Cys Leu Val Lys Gly Phe Tyr Pro Ser Asp Ile
    370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
                420                 425                 430

Ser Val Met His Glu Ala Leu His Asn His Tyr Thr Gln Lys Ser Leu
            435                 440                 445

Ser Leu Ser Pro Gly Lys
            450

<210> SEQ ID NO 78
<211> LENGTH: 219
<212> TYPE: PRT
<213> ORGANISM: Artificial
<220> FEATURE:
<223> OTHER INFORMATION: Bispecific <Tweak-IL-17> #2 antibody- light
      chain construct 1

<400> SEQUENCE: 78

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val His Ser
                20                  25                  30

Asn Gly Asp Thr Tyr Phe His Trp Tyr Leu Gln Lys Pro Gly Gln Ser
            35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Thr
                85                  90                  95

Thr His Ala Pro Phe Thr Phe Gly Gln Gly Thr Lys Leu Glu Ile Lys
                100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
                180                 185                 190

Lys His Lys Val Tyr Ala Cys Glu Val Thr His Gln Gly Leu Ser Ser
            195                 200                 205

Pro Val Thr Lys Ser Phe Asn Arg Gly Glu Cys
    210                 215

<210> SEQ ID NO 79
<211> LENGTH: 216
<212> TYPE: PRT
<213> ORGANISM: Artificial
<220> FEATURE:
<223> OTHER INFORMATION: Bispecific <Tweak-IL-17> #2 antibody- light
      chain construct 2
```

<400> SEQUENCE: 79

| Asp | Ile | Gln | Met | Thr | Gln | Ser | Pro | Ser | Ser | Val | Ser | Ala | Ser | Val | Gly |
| 1 | | | | 5 | | | | | 10 | | | | | 15 | |

| Asp | Arg | Val | Thr | Ile | Thr | Cys | Gln | Ala | Ser | Gln | Asn | Ile | Tyr | Ser | Asn |
| | | | 20 | | | | | 25 | | | | | 30 | | |

| Leu | Ala | Trp | Tyr | Gln | Gln | Lys | Pro | Gly | Lys | Ala | Pro | Lys | Leu | Leu | Ile |
| | | | 35 | | | | | 40 | | | | | 45 | | |

| Tyr | Thr | Ala | Ser | Tyr | Leu | Ala | Ser | Gly | Val | Pro | Ser | Arg | Phe | Ser | Gly |
| | 50 | | | | | 55 | | | | | 60 | | | | |

| Ser | Gly | Ser | Gly | Thr | Asp | Tyr | Thr | Leu | Thr | Ile | Ser | Ser | Leu | Gln | Pro |
| 65 | | | | | 70 | | | | | 75 | | | | | 80 |

| Glu | Asp | Phe | Ala | Thr | Tyr | Tyr | Cys | Gln | Thr | Ala | Tyr | Tyr | Asn | Ser | Arg |
| | | | | 85 | | | | | 90 | | | | | 95 | |

| Pro | Asp | Thr | Val | Ala | Phe | Gly | Gly | Thr | Lys | Val | Glu | Ile | Lys | Ser |
| | | | | 100 | | | | | 105 | | | | | 110 | Ser |

| Ser | Ala | Ser | Thr | Lys | Gly | Pro | Ser | Val | Phe | Pro | Leu | Ala | Pro | Ser | Ser |
| | | | | 115 | | | | | 120 | | | | | 125 | |

| Lys | Ser | Thr | Ser | Gly | Gly | Thr | Ala | Ala | Leu | Gly | Cys | Leu | Val | Lys | Asp |
| | 130 | | | | | 135 | | | | | 140 | | | | |

| Tyr | Phe | Pro | Glu | Pro | Val | Thr | Val | Ser | Trp | Asn | Ser | Gly | Ala | Leu | Thr |
| 145 | | | | | 150 | | | | | 155 | | | | | 160 |

| Ser | Gly | Val | His | Thr | Phe | Pro | Ala | Val | Leu | Gln | Ser | Ser | Gly | Leu | Tyr |
| | | | | 165 | | | | | 170 | | | | | 175 | |

| Ser | Leu | Ser | Ser | Val | Val | Thr | Val | Pro | Ser | Ser | Ser | Leu | Gly | Thr | Gln |
| | | | | 180 | | | | | 185 | | | | | 190 | |

| Thr | Tyr | Ile | Cys | Asn | Val | Asn | His | Lys | Pro | Ser | Asn | Thr | Lys | Val | Asp |
| | | | | 195 | | | | | 200 | | | | | 205 | |

| Lys | Lys | Val | Glu | Pro | Lys | Ser | Cys |
| | 210 | | | | | 215 | |

<210> SEQ ID NO 80
<211> LENGTH: 451
<212> TYPE: PRT
<213> ORGANISM: Artificial
<220> FEATURE:
<223> OTHER INFORMATION: Bispecific <Tweak-IL-17> #4 antibody- heavy chain construct 1

<400> SEQUENCE: 80

| Glu | Val | Gln | Leu | Val | Glu | Ser | Gly | Gly | Gly | Leu | Val | Gln | Pro | Gly | Gly |
| 1 | | | | 5 | | | | | 10 | | | | | 15 | |

| Ser | Leu | Arg | Leu | Ser | Cys | Ala | Ala | Ser | Gly | Phe | Ser | Leu | Asp | Ser | Tyr |
| | | | 20 | | | | | 25 | | | | | 30 | | |

| Gly | Val | His | Trp | Val | Arg | Gln | Ala | Thr | Gly | Lys | Gly | Leu | Glu | Trp | Val |
| | | | 35 | | | | | 40 | | | | | 45 | | |

| Ser | Val | Ile | Trp | Ser | Asp | Gly | Thr | Thr | Thr | Tyr | Asn | Ser | Ala | Leu | Lys |
| | 50 | | | | | 55 | | | | | 60 | | | | |

| Ser | Arg | Phe | Thr | Ile | Ser | Arg | Glu | Asn | Ala | Lys | Asn | Ser | Leu | Tyr | Leu |
| 65 | | | | | 70 | | | | | 75 | | | | | 80 |

| Gln | Met | Asn | Ser | Leu | Arg | Ala | Gly | Asp | Thr | Ala | Val | Tyr | Tyr | Cys | Ala |
| | | | | 85 | | | | | 90 | | | | | 95 | |

| Arg | Asp | Thr | His | Tyr | Arg | Leu | Tyr | Tyr | Tyr | Ala | Met | Asp | Tyr | Trp | Gly |
| | | | | 100 | | | | | 105 | | | | | 110 | |

| Gln | Gly | Thr | Thr | Val | Thr | Val | Ser | Ser | Ala | Ser | Thr | Lys | Gly | Pro | Ser |
| | | | | 115 | | | | | 120 | | | | | 125 | |

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Val Glu Pro Lys Ser Cys
210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Cys Thr Leu Pro Pro Ser Arg Asp Glu Leu Thr Lys Asn Gln Val Ser
        355                 360                 365

Leu Ser Cys Ala Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Val Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 81
<211> LENGTH: 700
<212> TYPE: PRT
<213> ORGANISM: Artificial
<220> FEATURE:
<223> OTHER INFORMATION: Bispecific <Tweak-IL-17> #4 antibody- heavy
      chain construct 2

<400> SEQUENCE: 81

Asp Ile Gln Met Thr Gln Ser Pro Ser Ser Val Ser Ala Ser Val Gly
1               5                   10                  15

Asp Arg Val Thr Ile Thr Cys Gln Ala Ser Gln Asn Ile Tyr Ser Asn

-continued

```
                 20                  25                  30
Leu Ala Trp Tyr Gln Gln Lys Pro Gly Lys Ala Pro Lys Leu Leu Ile
             35                  40                  45
Tyr Thr Ala Ser Tyr Leu Ala Ser Gly Val Pro Ser Arg Phe Ser Gly
 50                  55                  60
Ser Gly Ser Gly Thr Asp Tyr Thr Leu Thr Ile Ser Ser Leu Gln Pro
 65                  70                  75                  80
Glu Asp Phe Ala Thr Tyr Tyr Cys Gln Thr Ala Tyr Tyr Asn Ser Arg
                 85                  90                  95
Pro Asp Thr Val Ala Phe Gly Gly Thr Lys Val Glu Ile Lys Arg
            100                 105                 110
Thr Val Ala Ala Pro Ser Val Phe Ile Phe Pro Pro Ser Asp Glu Gln
            115                 120                 125
Leu Lys Ser Gly Thr Ala Ser Val Val Cys Leu Leu Asn Asn Phe Tyr
            130                 135                 140
Pro Arg Glu Ala Lys Val Gln Trp Lys Val Asp Asn Ala Leu Gln Ser
145                 150                 155                 160
Gly Asn Ser Gln Glu Ser Val Thr Glu Gln Asp Ser Lys Asp Ser Thr
                165                 170                 175
Tyr Ser Leu Ser Ser Thr Leu Thr Leu Ser Lys Ala Asp Tyr Glu Lys
            180                 185                 190
His Lys Val Tyr Ala Cys Glu Val Thr His Gln Gly Leu Ser Ser Pro
            195                 200                 205
Val Thr Lys Ser Phe Asn Arg Gly Glu Cys Gly Gly Gly Ser Gly
            210                 215                 220
Gly Gly Gly Ser Gly Gly Gly Gly Ser Gly Gly Gly Gly Ser Gly Gly
225                 230                 235                 240
Gly Gly Ser Gly Gly Gly Gly Ser Gly Gly Gln Val Gln Leu Val Gln
                245                 250                 255
Ser Gly Ala Glu Val Lys Lys Pro Gly Ser Ser Val Lys Val Ser Cys
            260                 265                 270
Lys Ala Ser Gly Phe Asp Phe Ser Thr Tyr Tyr Met Ser Trp Val Arg
            275                 280                 285
Gln Ala Pro Gly Gln Gly Leu Glu Trp Met Gly Thr Val Tyr Val Arg
            290                 295                 300
Gly Thr Thr Tyr Tyr Ala Ser Trp Leu Asn Gly Arg Val Thr Ile
305                 310                 315                 320
Thr Ala Asp Glu Ser Thr Ser Thr Ala Tyr Met Glu Leu Ser Ser Leu
                325                 330                 335
Arg Ser Glu Asp Thr Ala Val Tyr Tyr Cys Ala Arg Gly Gly Tyr Asn
            340                 345                 350
Tyr Asp Asp Ala Phe Val Ile Trp Gly Gln Gly Thr Leu Val Thr Val
            355                 360                 365
Ser Ser Ala Ser Thr Lys Gly Pro Ser Val Phe Pro Leu Ala Pro Ser
            370                 375                 380
Ser Lys Ser Thr Ser Gly Gly Thr Ala Ala Leu Gly Cys Leu Val Lys
385                 390                 395                 400
Asp Tyr Phe Pro Glu Pro Val Thr Val Ser Trp Asn Ser Gly Ala Leu
                405                 410                 415
Thr Ser Gly Val His Thr Phe Pro Ala Val Leu Gln Ser Ser Gly Leu
            420                 425                 430
Tyr Ser Leu Ser Ser Val Val Thr Val Pro Ser Ser Ser Leu Gly Thr
            435                 440                 445
```

```
Gln Thr Tyr Ile Cys Asn Val Asn His Lys Pro Ser Asn Thr Lys Val
    450                 455                 460

Asp Lys Lys Val Glu Pro Lys Ser Cys Asp Lys Thr His Thr Cys Pro
465                 470                 475                 480

Pro Cys Pro Ala Pro Glu Leu Leu Gly Gly Pro Ser Val Phe Leu Phe
                485                 490                 495

Pro Pro Lys Pro Lys Asp Thr Leu Met Ile Ser Arg Thr Pro Glu Val
            500                 505                 510

Thr Cys Val Val Val Asp Val Ser His Glu Asp Pro Glu Val Lys Phe
        515                 520                 525

Asn Trp Tyr Val Asp Gly Val Glu Val His Asn Ala Lys Thr Lys Pro
    530                 535                 540

Arg Glu Glu Gln Tyr Asn Ser Thr Tyr Arg Val Val Ser Val Leu Thr
545                 550                 555                 560

Val Leu His Gln Asp Trp Leu Asn Gly Lys Glu Tyr Lys Cys Lys Val
                565                 570                 575

Ser Asn Lys Ala Leu Pro Ala Pro Ile Glu Lys Thr Ile Ser Lys Ala
            580                 585                 590

Lys Gly Gln Pro Arg Glu Pro Gln Val Tyr Thr Leu Pro Pro Cys Arg
        595                 600                 605

Asp Glu Leu Thr Lys Asn Gln Val Ser Leu Trp Cys Leu Val Lys Gly
    610                 615                 620

Phe Tyr Pro Ser Asp Ile Ala Val Glu Trp Glu Ser Asn Gly Gln Pro
625                 630                 635                 640

Glu Asn Asn Tyr Lys Thr Thr Pro Pro Val Leu Asp Ser Asp Gly Ser
                645                 650                 655

Phe Phe Leu Tyr Ser Lys Leu Thr Val Asp Lys Ser Arg Trp Gln Gln
            660                 665                 670

Gly Asn Val Phe Ser Cys Ser Val Met His Glu Ala Leu His Asn His
        675                 680                 685

Tyr Thr Gln Lys Ser Leu Ser Leu Ser Pro Gly Lys
    690                 695                 700

<210> SEQ ID NO 82
<211> LENGTH: 219
<212> TYPE: PRT
<213> ORGANISM: Artificial
<220> FEATURE:
<223> OTHER INFORMATION: Bispecific <Tweak-IL-17> #4 antibody- light
      chain construct 1

<400> SEQUENCE: 82

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val His Ser
            20                  25                  30

Asn Gly Asp Thr Tyr Phe His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Thr
                85                  90                  95

Thr His Ala Pro Phe Thr Phe Gly Gln Gly Thr Lys Leu Glu Ile Lys
```

```
                  100                 105                 110
Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
        130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 83
<211> LENGTH: 937
<212> TYPE: PRT
<213> ORGANISM: Artificial
<220> FEATURE:
<223> OTHER INFORMATION: Bispecific <Tweak-IL-17> #5 antibody-heavy
      chain construct

<400> SEQUENCE: 83

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val His Ser
            20                  25                  30

Asn Gly Asp Thr Tyr Phe His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Thr
                85                  90                  95

Thr His Ala Pro Phe Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys Gly Gly Gly Gly Ser
    210                 215                 220

Gly Gly Gly Gly Ser Gly Gly Gly Ser Gly Gly Gly Gly Ser Gly
225                 230                 235                 240
```

Gly Gly Gly Ser Gly Gly Gly Ser Gly Gly Glu Val Gln Leu Val
                245                 250                 255

Glu Ser Gly Gly Gly Leu Val Gln Pro Gly Gly Ser Leu Arg Leu Ser
            260                 265                 270

Cys Ala Ala Ser Gly Phe Ser Leu Asp Ser Tyr Gly Val His Trp Val
        275                 280                 285

Arg Gln Ala Thr Gly Lys Gly Leu Glu Trp Val Ser Val Ile Trp Ser
    290                 295                 300

Asp Gly Thr Thr Thr Tyr Asn Ser Ala Leu Lys Ser Arg Phe Thr Ile
305                 310                 315                 320

Ser Arg Glu Asn Ala Lys Asn Ser Leu Tyr Leu Gln Met Asn Ser Leu
                325                 330                 335

Arg Ala Gly Asp Thr Ala Val Tyr Tyr Cys Ala Arg Asp Thr His Tyr
            340                 345                 350

Arg Leu Tyr Tyr Tyr Ala Met Asp Tyr Trp Gly Gln Gly Thr Thr Val
        355                 360                 365

Thr Val Ser Ser Ala Ser Thr Lys Gly Pro Ser Val Phe Pro Leu Ala
    370                 375                 380

Pro Ser Ser Lys Ser Thr Ser Gly Gly Thr Ala Ala Leu Gly Cys Leu
385                 390                 395                 400

Val Lys Asp Tyr Phe Pro Glu Pro Val Thr Val Ser Trp Asn Ser Gly
                405                 410                 415

Ala Leu Thr Ser Gly Val His Thr Phe Pro Ala Val Leu Gln Ser Ser
            420                 425                 430

Gly Leu Tyr Ser Leu Ser Ser Val Val Thr Val Pro Ser Ser Ser Leu
        435                 440                 445

Gly Thr Gln Thr Tyr Ile Cys Asn Val Asn His Lys Pro Ser Asn Thr
    450                 455                 460

Lys Val Asp Lys Lys Val Glu Pro Lys Ser Cys Gly Gly Gly Ser Gly
465                 470                 475                 480

Gly Gly Ser Gly Gly Gly Ser Gln Val Gln Leu Val Gln Ser Gly Ala
                485                 490                 495

Glu Val Lys Lys Pro Gly Ser Ser Val Lys Val Ser Cys Lys Ala Ser
            500                 505                 510

Gly Phe Asp Phe Ser Thr Tyr Tyr Met Ser Trp Val Arg Gln Ala Pro
        515                 520                 525

Gly Gln Gly Leu Glu Trp Met Gly Thr Val Tyr Val Arg Gln Gly Thr
    530                 535                 540

Thr Tyr Tyr Ala Ser Trp Leu Asn Gly Arg Val Thr Ile Thr Ala Asp
545                 550                 555                 560

Glu Ser Thr Ser Thr Ala Tyr Met Glu Leu Ser Ser Leu Arg Ser Glu
                565                 570                 575

Asp Thr Ala Val Tyr Tyr Cys Ala Arg Gly Gly Tyr Asn Tyr Asp Asp
            580                 585                 590

Ala Phe Val Ile Trp Gly Gln Gly Thr Leu Val Thr Val Ser Ser Ala
        595                 600                 605

Ser Thr Lys Gly Pro Ser Val Phe Pro Leu Ala Pro Ser Ser Lys Ser
    610                 615                 620

Thr Ser Gly Gly Thr Ala Ala Leu Gly Cys Leu Val Lys Asp Tyr Phe
625                 630                 635                 640

Pro Glu Pro Val Thr Val Ser Trp Asn Ser Gly Ala Leu Thr Ser Gly
                645                 650                 655

Val His Thr Phe Pro Ala Val Leu Gln Ser Ser Gly Leu Tyr Ser Leu

```
                660                 665                 670
Ser Ser Val Val Thr Val Pro Ser Ser Leu Gly Thr Gln Thr Tyr
            675                 680                 685

Ile Cys Asn Val Asn His Lys Pro Ser Asn Thr Lys Val Asp Lys Lys
            690                 695                 700

Val Glu Pro Lys Ser Cys Asp Lys Thr His Thr Cys Pro Pro Cys Pro
705                 710                 715                 720

Ala Pro Glu Leu Leu Gly Gly Pro Ser Val Phe Leu Phe Pro Pro Lys
                725                 730                 735

Pro Lys Asp Thr Leu Met Ile Ser Arg Thr Pro Glu Val Thr Cys Val
            740                 745                 750

Val Val Asp Val Ser His Glu Asp Pro Glu Val Lys Phe Asn Trp Tyr
            755                 760                 765

Val Asp Gly Val Glu Val His Asn Ala Lys Thr Lys Pro Arg Glu Glu
        770                 775                 780

Gln Tyr Asn Ser Thr Tyr Arg Val Val Ser Val Leu Thr Val Leu His
785                 790                 795                 800

Gln Asp Trp Leu Asn Gly Lys Glu Tyr Lys Cys Lys Val Ser Asn Lys
                805                 810                 815

Ala Leu Pro Ala Pro Ile Glu Lys Thr Ile Ser Lys Ala Lys Gly Gln
            820                 825                 830

Pro Arg Glu Pro Gln Val Tyr Thr Leu Pro Pro Ser Arg Asp Glu Leu
        835                 840                 845

Thr Lys Asn Gln Val Ser Leu Thr Cys Leu Val Lys Gly Phe Tyr Pro
    850                 855                 860

Ser Asp Ile Ala Val Glu Trp Glu Ser Asn Gly Gln Pro Glu Asn Asn
865                 870                 875                 880

Tyr Lys Thr Thr Pro Pro Val Leu Asp Ser Asp Gly Ser Phe Phe Leu
                885                 890                 895

Tyr Ser Lys Leu Thr Val Asp Lys Ser Arg Trp Gln Gln Gly Asn Val
            900                 905                 910

Phe Ser Cys Ser Val Met His Glu Ala Leu His Asn His Tyr Thr Gln
        915                 920                 925

Lys Ser Leu Ser Leu Ser Pro Gly Lys
    930                 935

<210> SEQ ID NO 84
<211> LENGTH: 218
<212> TYPE: PRT
<213> ORGANISM: Artificial
<220> FEATURE:
<223> OTHER INFORMATION: Bispecific <Tweak-IL-17> #5 antibody- light
      chain construct

<400> SEQUENCE: 84

Asp Ile Gln Met Thr Gln Ser Pro Ser Ser Val Ser Ala Ser Val Gly
1               5                   10                  15

Asp Arg Val Thr Ile Thr Cys Gln Ala Ser Gln Asn Ile Tyr Ser Asn
            20                  25                  30

Leu Ala Trp Tyr Gln Gln Lys Pro Gly Lys Ala Pro Lys Leu Leu Ile
        35                  40                  45

Tyr Thr Ala Ser Tyr Leu Ala Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80
```

```
Glu Asp Phe Ala Thr Tyr Tyr Cys Gln Thr Ala Tyr Tyr Asn Ser Arg
                85                  90                  95

Pro Asp Thr Val Ala Phe Gly Gly Gly Thr Lys Val Glu Ile Lys Arg
            100                 105                 110

Thr Val Ala Ala Pro Ser Val Phe Ile Phe Pro Pro Ser Asp Glu Gln
            115                 120                 125

Leu Lys Ser Gly Thr Ala Ser Val Val Cys Leu Leu Asn Asn Phe Tyr
        130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 85
<211> LENGTH: 448
<212> TYPE: PRT
<213> ORGANISM: Artificial
<220> FEATURE:
<223> OTHER INFORMATION: Bispecific <Tweak-IL-17> #20 antibody- heavy
      chain construct 1

<400> SEQUENCE: 85

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Asp Ser Tyr
            20                  25                  30

Gly Val His Trp Val Arg Gln Ala Thr Gly Lys Gly Leu Glu Trp Val
        35                  40                  45

Ser Val Ile Trp Ser Asp Gly Thr Thr Thr Tyr Asn Ser Ala Leu Lys
    50                  55                  60

Ser Arg Phe Thr Ile Ser Arg Glu Asn Ala Lys Asn Ser Leu Tyr Leu
65                  70                  75                  80

Gln Met Asn Ser Leu Arg Ala Gly Asp Thr Ala Val Tyr Tyr Cys Ala
                85                  90                  95

Arg Asp Thr His Tyr Arg Leu Tyr Tyr Tyr Ala Met Asp Tyr Trp Gly
            100                 105                 110

Gln Gly Thr Thr Val Thr Val Ser Ser Ala Ser Thr Lys Gly Pro Ser
        115                 120                 125

Val Phe Pro Leu Ala Pro Cys Ser Arg Ser Thr Ser Glu Ser Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Lys Thr Tyr Thr Cys Asn Val Asp His
        195                 200                 205

Lys Pro Ser Asn Thr Lys Val Asp Lys Arg Val Glu Ser Lys Tyr Gly
    210                 215                 220
```

-continued

Pro Pro Cys Pro Pro Cys Pro Ala Pro Glu Phe Glu Gly Gly Pro Ser
225                 230                 235                 240

Val Phe Leu Phe Pro Pro Lys Pro Lys Asp Thr Leu Met Ile Ser Arg
            245                 250                 255

Thr Pro Glu Val Thr Cys Val Val Val Asp Val Ser Gln Glu Asp Pro
        260                 265                 270

Glu Val Gln Phe Asn Trp Tyr Val Asp Gly Val Glu Val His Asn Ala
    275                 280                 285

Lys Thr Lys Pro Arg Glu Glu Gln Phe Asn Ser Thr Tyr Arg Val Val
290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335

Ile Ser Lys Ala Lys Gly Gln Pro Arg Glu Pro Gln Val Cys Thr Leu
            340                 345                 350

Pro Pro Ser Gln Glu Glu Met Thr Lys Asn Gln Val Ser Leu Ser Cys
        355                 360                 365

Ala Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Val Ser Arg Leu Thr Val Asp Lys Ser
                405                 410                 415

Arg Trp Gln Glu Gly Asn Val Phe Ser Cys Ser Val Met His Glu Ala
            420                 425                 430

Leu His Asn His Tyr Thr Gln Lys Ser Leu Ser Leu Ser Leu Gly Lys
        435                 440                 445

<210> SEQ ID NO 86
<211> LENGTH: 697
<212> TYPE: PRT
<213> ORGANISM: Artificial
<220> FEATURE:
<223> OTHER INFORMATION: Bispecific <Tweak-IL-17> #20 antibody- heavy
      chain construct 2

<400> SEQUENCE: 86

Asp Ile Gln Met Thr Gln Ser Pro Ser Ser Val Ser Ala Ser Val Gly
1               5                   10                  15

Asp Arg Val Thr Ile Thr Cys Gln Ala Ser Gln Asn Ile Tyr Ser Asn
            20                  25                  30

Leu Ala Trp Tyr Gln Gln Lys Pro Gly Lys Ala Pro Lys Leu Leu Ile
        35                  40                  45

Tyr Thr Ala Ser Tyr Leu Ala Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Thr Ala Tyr Tyr Asn Ser Arg
                85                  90                  95

Pro Asp Thr Val Ala Phe Gly Gly Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr

```
            130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys Gly Gly Gly Ser Gly
210                 215                 220

Gly Gly Gly Ser Gly Gly Gly Gly Ser Gly Gly Gly Gly Ser Gly Gly
225                 230                 235                 240

Gly Gly Ser Gly Gly Gly Gly Ser Gly Gly Gln Val Gln Leu Val Gln
                245                 250                 255

Ser Gly Ala Glu Val Lys Lys Pro Gly Ser Ser Val Lys Val Ser Cys
            260                 265                 270

Lys Ala Ser Gly Phe Asp Phe Ser Thr Tyr Tyr Met Ser Trp Val Arg
        275                 280                 285

Gln Ala Pro Gly Gln Gly Leu Glu Trp Met Gly Thr Val Tyr Val Arg
        290                 295                 300

Gln Gly Thr Thr Tyr Tyr Ala Ser Trp Leu Asn Gly Arg Val Thr Ile
305                 310                 315                 320

Thr Ala Asp Glu Ser Thr Ser Thr Ala Tyr Met Glu Leu Ser Ser Leu
                325                 330                 335

Arg Ser Glu Asp Thr Ala Val Tyr Tyr Cys Ala Arg Gly Gly Tyr Asn
            340                 345                 350

Tyr Asp Asp Ala Phe Val Ile Trp Gly Gln Gly Thr Leu Val Thr Val
        355                 360                 365

Ser Ser Ala Ser Thr Lys Gly Pro Ser Val Phe Pro Leu Ala Pro Cys
        370                 375                 380

Ser Arg Ser Thr Ser Glu Ser Thr Ala Ala Leu Gly Cys Leu Val Lys
385                 390                 395                 400

Asp Tyr Phe Pro Glu Pro Val Thr Val Ser Trp Asn Ser Gly Ala Leu
                405                 410                 415

Thr Ser Gly Val His Thr Phe Pro Ala Val Leu Gln Ser Ser Gly Leu
            420                 425                 430

Tyr Ser Leu Ser Ser Val Val Thr Val Pro Ser Ser Ser Leu Gly Thr
        435                 440                 445

Lys Thr Tyr Thr Cys Asn Val Asp His Lys Pro Ser Asn Thr Lys Val
        450                 455                 460

Asp Lys Arg Val Glu Ser Lys Tyr Gly Pro Pro Cys Pro Pro Cys Pro
465                 470                 475                 480

Ala Pro Glu Phe Glu Gly Gly Pro Ser Val Phe Leu Phe Pro Pro Lys
                485                 490                 495

Pro Lys Asp Thr Leu Met Ile Ser Arg Thr Pro Glu Val Thr Cys Val
            500                 505                 510

Val Val Asp Val Ser Gln Glu Asp Pro Glu Val Gln Phe Asn Trp Tyr
        515                 520                 525

Val Asp Gly Val Glu Val His Asn Ala Lys Thr Lys Pro Arg Glu Glu
        530                 535                 540

Gln Phe Asn Ser Thr Tyr Arg Val Val Ser Val Leu Thr Val Leu His
545                 550                 555                 560
```

```
Gln Asp Trp Leu Asn Gly Lys Glu Tyr Lys Cys Lys Val Ser Asn Lys
                565                 570                 575

Gly Leu Pro Ser Ser Ile Glu Lys Thr Ile Ser Lys Ala Lys Gly Gln
            580                 585                 590

Pro Arg Glu Pro Gln Val Tyr Thr Leu Pro Pro Cys Gln Glu Glu Met
        595                 600                 605

Thr Lys Asn Gln Val Ser Leu Trp Cys Leu Val Lys Gly Phe Tyr Pro
    610                 615                 620

Ser Asp Ile Ala Val Glu Trp Glu Ser Asn Gly Gln Pro Glu Asn Asn
625                 630                 635                 640

Tyr Lys Thr Thr Pro Pro Val Leu Asp Ser Asp Gly Ser Phe Phe Leu
                645                 650                 655

Tyr Ser Arg Leu Thr Val Asp Lys Ser Arg Trp Gln Glu Gly Asn Val
            660                 665                 670

Phe Ser Cys Ser Val Met His Glu Ala Leu His Asn His Tyr Thr Gln
        675                 680                 685

Lys Ser Leu Ser Leu Ser Leu Gly Lys
    690                 695

<210> SEQ ID NO 87
<211> LENGTH: 219
<212> TYPE: PRT
<213> ORGANISM: Artificial
<220> FEATURE:
<223> OTHER INFORMATION: Bispecific <Tweak-IL-17> #20 antibody- light
      chain construct 1

<400> SEQUENCE: 87

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val His Ser
            20                  25                  30

Asn Gly Asp Thr Tyr Phe His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Thr
                85                  90                  95

Thr His Ala Pro Phe Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```

<210> SEQ ID NO 88
<211> LENGTH: 448
<212> TYPE: PRT
<213> ORGANISM: Artificial
<220> FEATURE:
<223> OTHER INFORMATION: Bispecific <Tweak-IL-17> #21 antibody- heavy chain construct 1

<400> SEQUENCE: 88

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Asp Ser Tyr
            20                  25                  30

Gly Val His Trp Val Arg Gln Ala Pro Gly Lys Gly Leu Glu Trp Val
        35                  40                  45

Ser Val Ile Trp Ser Asp Gly Thr Thr Thr Tyr Asn Ser Ala Leu Lys
    50                  55                  60

Ser Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Asp Thr His Tyr Arg Leu Tyr Tyr Tyr Ala Met Asp Tyr Trp Gly
            100                 105                 110

Gln Gly Thr Thr Val Thr Val Ser Ala Ser Thr Lys Gly Pro Ser
        115                 120                 125

Val Phe Pro Leu Ala Pro Cys Ser Arg Ser Thr Ser Glu Ser Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Lys Thr Tyr Thr Cys Asn Val Asp His
        195                 200                 205

Lys Pro Ser Asn Thr Lys Val Asp Lys Arg Val Glu Ser Lys Tyr Gly
    210                 215                 220

Pro Pro Cys Pro Pro Cys Pro Ala Pro Glu Phe Glu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser Gln Glu Asp Pro
            260                 265                 270

Glu Val Gln Phe Asn Trp Tyr Val Asp Gly Val Glu Val His Asn Ala
        275                 280                 285

Lys Thr Lys Pro Arg Glu Glu Gln Phe Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335

Ile Ser Lys Ala Lys Gly Gln Pro Arg Glu Pro Gln Val Cys Thr Leu
            340                 345                 350

```
Pro Pro Ser Gln Glu Glu Met Thr Lys Asn Gln Val Ser Leu Ser Cys
            355                 360                 365
Ala Val Lys Gly Phe Tyr Pro Ser Asp Ile Ala Val Glu Trp Glu Ser
370                 375                 380
Asn Gly Gln Pro Glu Asn Asn Tyr Lys Thr Thr Pro Pro Val Leu Asp
385                 390                 395                 400
Ser Asp Gly Ser Phe Phe Leu Val Ser Arg Leu Thr Val Asp Lys Ser
            405                 410                 415
Arg Trp Gln Glu Gly Asn Val Phe Ser Cys Ser Val Met His Glu Ala
            420                 425                 430
Leu His Asn His Tyr Thr Gln Lys Ser Leu Ser Leu Ser Leu Gly Lys
            435                 440                 445
```

<210> SEQ ID NO 89
<211> LENGTH: 697
<212> TYPE: PRT
<213> ORGANISM: Artificial
<220> FEATURE:
<223> OTHER INFORMATION: Bispecific <Tweak-IL-17> #21 antibody- heavy
      chain construct 2

<400> SEQUENCE: 89

```
Asp Ile Gln Met Thr Gln Ser Pro Ser Ser Val Ser Ala Ser Val Gly
1               5                   10                  15
Asp Arg Val Thr Ile Thr Cys Gln Ala Ser Gln Asn Ile Tyr Ser Asn
            20                  25                  30
Leu Ala Trp Tyr Gln Gln Lys Pro Gly Lys Ala Pro Lys Leu Leu Ile
        35                  40                  45
Tyr Thr Ala Ser Tyr Leu Ala Ser Gly Val Pro Ser Arg Phe Ser Gly
    50                  55                  60
Ser Gly Ser Gly Thr Asp Tyr Thr Leu Thr Ile Ser Ser Leu Gln Pro
65                  70                  75                  80
Glu Asp Phe Ala Thr Tyr Tyr Cys Gln Thr Ala Tyr Tyr Asn Ser Arg
                85                  90                  95
Pro Asp Thr Val Ala Phe Gly Gly Thr Lys Val Glu Ile Lys Arg
            100                 105                 110
Thr Val Ala Ala Pro Ser Val Phe Ile Phe Pro Pro Ser Asp Glu Gln
        115                 120                 125
Leu Lys Ser Gly Thr Ala Ser Val Val Cys Leu Leu Asn Asn Phe Tyr
    130                 135                 140
Pro Arg Glu Ala Lys Val Gln Trp Lys Val Asp Asn Ala Leu Gln Ser
145                 150                 155                 160
Gly Asn Ser Gln Glu Ser Val Thr Glu Gln Asp Ser Lys Asp Ser Thr
                165                 170                 175
Tyr Ser Leu Ser Ser Thr Leu Thr Leu Ser Lys Ala Asp Tyr Glu Lys
            180                 185                 190
His Lys Val Tyr Ala Cys Glu Val Thr His Gln Gly Leu Ser Ser Pro
        195                 200                 205
Val Thr Lys Ser Phe Asn Arg Gly Glu Cys Gly Gly Gly Gly Ser Gly
    210                 215                 220
Gly Gly Gly Ser Gly Gly Gly Gly Ser Gly Gly Gly Gly Ser Gly Gly
225                 230                 235                 240
Gly Gly Ser Gly Gly Gly Gly Ser Gly Gly Gln Val Gln Leu Val Gln
                245                 250                 255
Ser Gly Ala Glu Val Lys Lys Pro Gly Ser Ser Val Lys Val Ser Cys
            260                 265                 270
```

```
Lys Ala Ser Gly Phe Asp Phe Ser Thr Tyr Tyr Met Ser Trp Val Arg
            275                 280                 285

Gln Ala Pro Gly Gln Gly Leu Glu Trp Met Gly Thr Val Tyr Val Arg
        290                 295                 300

Gln Gly Thr Thr Tyr Tyr Ala Ser Trp Leu Asn Gly Arg Val Thr Ile
305                 310                 315                 320

Thr Ala Asp Glu Ser Thr Ser Thr Ala Tyr Met Glu Leu Ser Ser Leu
                325                 330                 335

Arg Ser Glu Asp Thr Ala Val Tyr Tyr Cys Ala Arg Gly Gly Tyr Asn
            340                 345                 350

Tyr Asp Asp Ala Phe Val Ile Trp Gly Gln Gly Thr Leu Val Thr Val
        355                 360                 365

Ser Ser Ala Ser Thr Lys Gly Pro Ser Val Phe Pro Leu Ala Pro Cys
    370                 375                 380

Ser Arg Ser Thr Ser Glu Ser Thr Ala Ala Leu Gly Cys Leu Val Lys
385                 390                 395                 400

Asp Tyr Phe Pro Glu Pro Val Thr Val Ser Trp Asn Ser Gly Ala Leu
                405                 410                 415

Thr Ser Gly Val His Thr Phe Pro Ala Val Leu Gln Ser Ser Gly Leu
            420                 425                 430

Tyr Ser Leu Ser Ser Val Val Thr Val Pro Ser Ser Ser Leu Gly Thr
        435                 440                 445

Lys Thr Tyr Thr Cys Asn Val Asp His Lys Pro Ser Asn Thr Lys Val
    450                 455                 460

Asp Lys Arg Val Glu Ser Lys Tyr Gly Pro Pro Cys Pro Pro Cys Pro
465                 470                 475                 480

Ala Pro Glu Phe Glu Gly Gly Pro Ser Val Phe Leu Phe Pro Pro Lys
                485                 490                 495

Pro Lys Asp Thr Leu Met Ile Ser Arg Thr Pro Glu Val Thr Cys Val
            500                 505                 510

Val Val Asp Val Ser Gln Glu Asp Pro Glu Val Gln Phe Asn Trp Tyr
        515                 520                 525

Val Asp Gly Val Glu Val His Asn Ala Lys Thr Lys Pro Arg Glu Glu
    530                 535                 540

Gln Phe Asn Ser Thr Tyr Arg Val Val Ser Val Leu Thr Val Leu His
545                 550                 555                 560

Gln Asp Trp Leu Asn Gly Lys Glu Tyr Lys Cys Lys Val Ser Asn Lys
                565                 570                 575

Gly Leu Pro Ser Ser Ile Glu Lys Thr Ile Ser Lys Ala Lys Gly Gln
            580                 585                 590

Pro Arg Glu Pro Gln Val Tyr Thr Leu Pro Pro Cys Gln Glu Glu Met
        595                 600                 605

Thr Lys Asn Gln Val Ser Leu Trp Cys Leu Val Lys Gly Phe Tyr Pro
    610                 615                 620

Ser Asp Ile Ala Val Glu Trp Glu Ser Asn Gly Gln Pro Glu Asn Asn
625                 630                 635                 640

Tyr Lys Thr Thr Pro Pro Val Leu Asp Ser Asp Gly Ser Phe Phe Leu
                645                 650                 655

Tyr Ser Arg Leu Thr Val Asp Lys Ser Arg Trp Gln Glu Gly Asn Val
            660                 665                 670

Phe Ser Cys Ser Val Met His Glu Ala Leu His Asn His Tyr Thr Gln
        675                 680                 685
```

```
Lys Ser Leu Ser Leu Ser Leu Gly Lys
    690                 695
```

<210> SEQ ID NO 90
<211> LENGTH: 219
<212> TYPE: PRT
<213> ORGANISM: Artificial
<220> FEATURE:
<223> OTHER INFORMATION: Bispecific <Tweak-IL-17> #21 antibody- light
      chain construct 1

<400> SEQUENCE: 90

```
Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val His Ser
            20                  25                  30

Asn Gly Asp Thr Tyr Phe His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Thr
                85                  90                  95

Thr His Ala Pro Phe Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```

<210> SEQ ID NO 91
<211> LENGTH: 451
<212> TYPE: PRT
<213> ORGANISM: Artificial
<220> FEATURE:
<223> OTHER INFORMATION: Bispecific <Tweak-IL-17> #23 antibody- heavy
      chain construct 1

<400> SEQUENCE: 91

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Asp Ser Tyr
            20                  25                  30

Gly Val His Trp Val Arg Gln Ala Pro Gly Lys Gly Leu Glu Trp Val
        35                  40                  45

Ser Val Ile Trp Ser Asp Gly Thr Thr Thr Tyr Asn Ser Ala Leu Lys
    50                  55                  60
```

```
Ser Arg Phe Thr Ile Ser Arg Asp Asn Ser Lys Asn Thr Leu Tyr Leu
 65                  70                  75                  80

Gln Met Asn Ser Leu Arg Ala Glu Asp Thr Ala Val Tyr Tyr Cys Ala
             85                  90                  95

Arg Asp Thr His Tyr Arg Leu Tyr Tyr Tyr Ala Met Asp Tyr Trp Gly
            100                 105                 110

Gln Gly Thr Thr Val Thr Val Ser Ala Ser Thr Lys Gly Pro Ser
        115                 120                 125

Val Phe Pro Leu Ala Pro Ser Ser Lys Ser Thr Ser Gly Gly Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Val Glu Pro Lys Ser Cys
210                 215                 220

Asp Lys Thr His Thr Cys Pro Pro Cys Pro Ala Pro Glu Ala Ala Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Gly Ala Pro Ile
                325                 330                 335

Glu Lys Thr Ile Ser Lys Ala Lys Gly Gln Pro Arg Glu Pro Gln Val
            340                 345                 350

Cys Thr Leu Pro Pro Ser Arg Asp Glu Leu Thr Lys Asn Gln Val Ser
        355                 360                 365

Leu Ser Cys Ala Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Val Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 92
<211> LENGTH: 700
<212> TYPE: PRT
```

<213> ORGANISM: Artificial
<220> FEATURE:
<223> OTHER INFORMATION: Bispecific <Tweak-IL-17> #23 antibody- heavy chain construct 2

<400> SEQUENCE: 92

| | | | | | | | | | | | | | | |
|---|---|---|---|---|---|---|---|---|---|---|---|---|---|---|
| Asp | Ile | Gln | Met | Thr | Gln | Ser | Pro | Ser | Ser | Val | Ser | Ala | Ser | Val | Gly |
| 1 | | | | 5 | | | | | 10 | | | | | 15 | |
| Asp | Arg | Val | Thr | Ile | Thr | Cys | Gln | Ala | Ser | Gln | Asn | Ile | Tyr | Ser | Asn |
| | | | 20 | | | | | 25 | | | | | 30 | | |
| Leu | Ala | Trp | Tyr | Gln | Gln | Lys | Pro | Gly | Lys | Ala | Pro | Lys | Leu | Leu | Ile |
| | | | 35 | | | | | 40 | | | | | 45 | | |
| Tyr | Thr | Ala | Ser | Tyr | Leu | Ala | Ser | Gly | Val | Pro | Ser | Arg | Phe | Ser | Gly |
| | 50 | | | | | 55 | | | | | 60 | | | | |
| Ser | Gly | Ser | Gly | Thr | Asp | Tyr | Thr | Leu | Thr | Ile | Ser | Ser | Leu | Gln | Pro |
| 65 | | | | | 70 | | | | | 75 | | | | | 80 |
| Glu | Asp | Phe | Ala | Thr | Tyr | Tyr | Cys | Gln | Thr | Ala | Tyr | Tyr | Asn | Ser | Arg |
| | | | | 85 | | | | | 90 | | | | | 95 | |
| Pro | Asp | Thr | Val | Ala | Phe | Gly | Gly | Thr | Lys | Val | Glu | Ile | Lys | Arg |
| | | | 100 | | | | | 105 | | | | | 110 | | |
| Thr | Val | Ala | Ala | Pro | Ser | Val | Phe | Ile | Phe | Pro | Pro | Ser | Asp | Glu | Gln |
| | | 115 | | | | | 120 | | | | | 125 | | | |
| Leu | Lys | Ser | Gly | Thr | Ala | Ser | Val | Val | Cys | Leu | Leu | Asn | Asn | Phe | Tyr |
| | 130 | | | | | 135 | | | | | 140 | | | | |
| Pro | Arg | Glu | Ala | Lys | Val | Gln | Trp | Lys | Val | Asp | Asn | Ala | Leu | Gln | Ser |
| 145 | | | | | 150 | | | | | 155 | | | | | 160 |
| Gly | Asn | Ser | Gln | Glu | Ser | Val | Thr | Glu | Gln | Asp | Ser | Lys | Asp | Ser | Thr |
| | | | | 165 | | | | | 170 | | | | | 175 | |
| Tyr | Ser | Leu | Ser | Ser | Thr | Leu | Thr | Leu | Ser | Lys | Ala | Asp | Tyr | Glu | Lys |
| | | | 180 | | | | | 185 | | | | | 190 | | |
| His | Lys | Val | Tyr | Ala | Cys | Glu | Val | Thr | His | Gln | Gly | Leu | Ser | Ser | Pro |
| | | 195 | | | | | 200 | | | | | 205 | | | |
| Val | Thr | Lys | Ser | Phe | Asn | Arg | Gly | Glu | Cys | Gly | Gly | Gly | Ser | Gly |
| | 210 | | | | | 215 | | | | | 220 | | | | |
| Gly | Gly | Gly | Ser | Gly | Gly | Gly | Ser | Gly | Gly | Gly | Ser | Gly | Gly |
| 225 | | | | | 230 | | | | | 235 | | | | | 240 |
| Gly | Gly | Ser | Gly | Gly | Gly | Ser | Gly | Gly | Gln | Val | Gln | Leu | Val | Gln |
| | | | | 245 | | | | | 250 | | | | | 255 | |
| Ser | Gly | Ala | Glu | Val | Lys | Lys | Pro | Gly | Ser | Ser | Val | Lys | Val | Ser | Cys |
| | | | 260 | | | | | 265 | | | | | 270 | | |
| Lys | Ala | Ser | Gly | Phe | Asp | Phe | Ser | Thr | Tyr | Tyr | Met | Ser | Trp | Val | Arg |
| | | 275 | | | | | 280 | | | | | 285 | | | |
| Gln | Ala | Pro | Gly | Gln | Gly | Leu | Glu | Trp | Met | Gly | Thr | Val | Tyr | Val | Arg |
| | 290 | | | | | 295 | | | | | 300 | | | | |
| Gln | Gly | Thr | Thr | Tyr | Tyr | Ala | Ser | Trp | Leu | Asn | Gly | Arg | Val | Thr | Ile |
| 305 | | | | | 310 | | | | | 315 | | | | | 320 |
| Thr | Ala | Asp | Glu | Ser | Thr | Ser | Thr | Ala | Tyr | Met | Glu | Leu | Ser | Ser | Leu |
| | | | | 325 | | | | | 330 | | | | | 335 | |
| Arg | Ser | Glu | Asp | Thr | Ala | Val | Tyr | Tyr | Cys | Ala | Arg | Gly | Gly | Tyr | Asn |
| | | | 340 | | | | | 345 | | | | | 350 | | |
| Tyr | Asp | Asp | Ala | Phe | Val | Ile | Trp | Gly | Gln | Gly | Thr | Leu | Val | Thr | Val |
| | | 355 | | | | | 360 | | | | | 365 | | | |
| Ser | Ser | Ala | Ser | Thr | Lys | Gly | Pro | Ser | Val | Phe | Pro | Leu | Ala | Pro | Ser |
| | 370 | | | | | 375 | | | | | 380 | | | | |

-continued

```
Ser Lys Ser Thr Ser Gly Gly Thr Ala Ala Leu Gly Cys Leu Val Lys
385                 390                 395                 400

Asp Tyr Phe Pro Glu Pro Val Thr Val Ser Trp Asn Ser Gly Ala Leu
            405                 410                 415

Thr Ser Gly Val His Thr Phe Pro Ala Val Leu Gln Ser Ser Gly Leu
        420                 425                 430

Tyr Ser Leu Ser Ser Val Val Thr Val Pro Ser Ser Ser Leu Gly Thr
    435                 440                 445

Gln Thr Tyr Ile Cys Asn Val Asn His Lys Pro Ser Asn Thr Lys Val
450                 455                 460

Asp Lys Lys Val Glu Pro Lys Ser Cys Asp Lys Thr His Thr Cys Pro
465                 470                 475                 480

Pro Cys Pro Ala Pro Glu Ala Ala Gly Gly Pro Ser Val Phe Leu Phe
            485                 490                 495

Pro Pro Lys Pro Lys Asp Thr Leu Met Ile Ser Arg Thr Pro Glu Val
        500                 505                 510

Thr Cys Val Val Val Asp Val Ser His Glu Asp Pro Glu Val Lys Phe
    515                 520                 525

Asn Trp Tyr Val Asp Gly Val Glu Val His Asn Ala Lys Thr Lys Pro
530                 535                 540

Arg Glu Glu Gln Tyr Asn Ser Thr Tyr Arg Val Val Ser Val Leu Thr
545                 550                 555                 560

Val Leu His Gln Asp Trp Leu Asn Gly Lys Glu Tyr Lys Cys Lys Val
            565                 570                 575

Ser Asn Lys Ala Leu Gly Ala Pro Ile Glu Lys Thr Ile Ser Lys Ala
        580                 585                 590

Lys Gly Gln Pro Arg Glu Pro Gln Val Tyr Thr Leu Pro Pro Cys Arg
    595                 600                 605

Asp Glu Leu Thr Lys Asn Gln Val Ser Leu Trp Cys Leu Val Lys Gly
610                 615                 620

Phe Tyr Pro Ser Asp Ile Ala Val Glu Trp Ser Asn Gly Gln Pro
625                 630                 635                 640

Glu Asn Asn Tyr Lys Thr Thr Pro Pro Val Leu Asp Ser Asp Gly Ser
            645                 650                 655

Phe Phe Leu Tyr Ser Lys Leu Thr Val Asp Lys Ser Arg Trp Gln Gln
        660                 665                 670

Gly Asn Val Phe Ser Cys Ser Val Met His Glu Ala Leu His Asn His
    675                 680                 685

Tyr Thr Gln Lys Ser Leu Ser Leu Ser Pro Gly Lys
690                 695                 700

<210> SEQ ID NO 93
<211> LENGTH: 219
<212> TYPE: PRT
<213> ORGANISM: Artificial
<220> FEATURE:
<223> OTHER INFORMATION: Bispecific <Tweak-IL-17> #23 antibody- light
      chain construct 1

<400> SEQUENCE: 93

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val His Ser
            20                  25                  30

Asn Gly Asp Thr Tyr Phe His Trp Tyr Leu Gln Lys Pro Gly Gln Ser
        35                  40                  45
```

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Thr
                85                  90                  95

Thr His Ala Pro Phe Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 94
<211> LENGTH: 450
<212> TYPE: PRT
<213> ORGANISM: Artificial
<220> FEATURE:
<223> OTHER INFORMATION: Bispecific <Tweak-IL-17> #24 antibody- heavy
      chain construct 1

<400> SEQUENCE: 94

Gln Val Gln Leu Val Gln Ser Gly Ala Glu Val Lys Lys Pro Gly Ser
1               5                   10                  15

Ser Val Lys Val Ser Cys Lys Ala Ser Gly Phe Asp Phe Ser Thr Tyr
            20                  25                  30

Tyr Met Ser Trp Val Arg Gln Ala Pro Gly Gln Gly Leu Glu Trp Met
        35                  40                  45

Gly Thr Val Tyr Val Arg Gln Gly Thr Thr Tyr Tyr Ala Ser Trp Leu
    50                  55                  60

Asn Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Tyr Asn Tyr Asp Asp Ala Phe Val Ile Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro

```
                180                 185                 190
Ser Ser Ser Leu Gly Thr Gln Thr Tyr Ile Cys Asn Val Asn His Lys
            195                 200                 205

Pro Ser Asn Thr Lys Val Asp Lys Lys Val Glu Pro Lys Ser Cys Asp
        210                 215                 220

Lys Thr His Thr Cys Pro Pro Cys Pro Ala Pro Glu Ala Ala Gly Gly
225                 230                 235                 240

Pro Ser Val Phe Leu Phe Pro Pro Lys Pro Lys Asp Thr Leu Met Ile
            245                 250                 255

Ser Arg Thr Pro Glu Val Thr Cys Val Val Val Asp Val Ser His Glu
        260                 265                 270

Asp Pro Glu Val Lys Phe Asn Trp Tyr Val Asp Gly Val Glu Val His
    275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Gly Ala Pro Ile Glu
                325                 330                 335

Lys Thr Ile Ser Lys Ala Lys Gly Gln Pro Arg Glu Pro Gln Val Cys
            340                 345                 350

Thr Leu Pro Pro Ser Arg Asp Glu Leu Thr Lys Asn Gln Val Ser Leu
        355                 360                 365

Ser Cys Ala Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Val Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 95
<211> LENGTH: 455
<212> TYPE: PRT
<213> ORGANISM: Artificial
<220> FEATURE:
<223> OTHER INFORMATION: Bispecific <Tweak-IL-17> #24 antibody- heavy
      chain construct 2

<400> SEQUENCE: 95

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Asp Ser Tyr
            20                  25                  30

Gly Val His Trp Val Arg Gln Ala Pro Gly Lys Gly Leu Glu Trp Val
        35                  40                  45

Ser Val Ile Trp Ser Asp Gly Thr Thr Tyr Asn Ser Ala Leu Lys
    50                  55                  60

Ser Arg Phe Thr Ile Ser Arg Asp Asn Ser Lys Asn Thr Leu Tyr Leu
65                  70                  75                  80
```

```
Gln Met Asn Ser Leu Arg Ala Glu Asp Thr Ala Val Tyr Tyr Cys Ala
                 85                  90                  95

Arg Asp Thr His Tyr Arg Leu Tyr Tyr Tyr Ala Met Asp Tyr Trp Gly
            100                 105                 110

Gln Gly Thr Thr Val Thr Val Ser Ser Ala Ser Val Ala Ala Pro Ser
        115                 120                 125

Val Phe Ile Phe Pro Pro Ser Asp Glu Gln Leu Lys Ser Gly Thr Ala
    130                 135                 140

Ser Val Val Cys Leu Leu Asn Asn Phe Tyr Pro Arg Glu Ala Lys Val
145                 150                 155                 160

Gln Trp Lys Val Asp Asn Ala Leu Gln Ser Gly Asn Ser Gln Glu Ser
                165                 170                 175

Val Thr Glu Gln Asp Ser Lys Asp Ser Thr Tyr Ser Leu Ser Ser Thr
            180                 185                 190

Leu Thr Leu Ser Lys Ala Asp Tyr Glu Lys His Lys Val Tyr Ala Cys
        195                 200                 205

Glu Val Thr His Gln Gly Leu Ser Ser Pro Val Thr Lys Ser Phe Asn
    210                 215                 220

Arg Gly Glu Cys Asp Lys Thr His Thr Cys Pro Pro Cys Pro Ala Pro
225                 230                 235                 240

Glu Ala Ala Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
        275                 280                 285

Gly Val Glu Val His Asn Ala Lys Thr Lys Pro Arg Glu Glu Gln Tyr
    290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Gly Ala Pro Ile Glu Lys Thr Ile Ser Lys Ala Lys Gly Gln Pro Arg
            340                 345                 350

Glu Pro Gln Val Tyr Thr Leu Pro Pro Cys Arg Asp Glu Leu Thr Lys
        355                 360                 365

Asn Gln Val Ser Leu Trp Cys Leu Val Lys Gly Phe Tyr Pro Ser Asp
    370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Lys Leu Thr Val Asp Lys Ser Arg Trp Gln Gln Gly Asn Val Phe Ser
            420                 425                 430

Cys Ser Val Met His Glu Ala Leu His Asn His Tyr Thr Gln Lys Ser
        435                 440                 445

Leu Ser Leu Ser Pro Gly Lys
    450                 455

<210> SEQ ID NO 96
<211> LENGTH: 218
<212> TYPE: PRT
<213> ORGANISM: Artificial
<220> FEATURE:
<223> OTHER INFORMATION: Bispecific <Tweak-IL-17> #24 antibody- light
``` chain construct 1

<400> SEQUENCE: 96

Asp Ile Gln Met Thr Gln Ser Pro Ser Ser Val Ser Ala Ser Val Gly
1               5                   10                  15

Asp Arg Val Thr Ile Thr Cys Gln Ala Ser Gln Asn Ile Tyr Ser Asn
            20                  25                  30

Leu Ala Trp Tyr Gln Gln Lys Pro Gly Lys Ala Pro Lys Leu Leu Ile
        35                  40                  45

Tyr Thr Ala Ser Tyr Leu Ala Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Thr Ala Tyr Tyr Asn Ser Arg
                85                  90                  95

Pro Asp Thr Val Ala Phe Gly Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 97
<211> LENGTH: 217
<212> TYPE: PRT
<213> ORGANISM: Artificial
<220> FEATURE:
<223> OTHER INFORMATION: Bispecific <Tweak-IL-17> #24 antibody- light
      chain construct 2

<400> SEQUENCE: 97

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val His Ser
            20                  25                  30

Asn Gly Asp Thr Tyr Phe His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Thr
                85                  90                  95

Thr His Ala Pro Phe Thr Phe Gly Gln Gly Thr Lys Leu Glu Ile Lys
            100                 105                 110

Ser Ser Ala Ser Thr Lys Gly Pro Ser Val Phe Pro Leu Ala Pro Ser

```
              115                 120                 125
Ser Lys Ser Thr Ser Gly Gly Thr Ala Ala Leu Gly Cys Leu Val Lys
    130                 135                 140

Asp Tyr Phe Pro Glu Pro Val Thr Val Ser Trp Asn Ser Gly Ala Leu
145                 150                 155                 160

Thr Ser Gly Val His Thr Phe Pro Ala Val Leu Gln Ser Ser Gly Leu
                165                 170                 175

Tyr Ser Leu Ser Ser Val Val Thr Val Pro Ser Ser Ser Leu Gly Thr
                180                 185                 190

Gln Thr Tyr Ile Cys Asn Val Asn His Lys Pro Ser Asn Thr Lys Val
                195                 200                 205

Asp Lys Lys Val Glu Pro Lys Ser Cys
    210                 215

<210> SEQ ID NO 98
<211> LENGTH: 129
<212> TYPE: PRT
<213> ORGANISM: Homo sapiens

<400> SEQUENCE: 98

Met Ala Arg Gly Ser Leu Arg Arg Leu Leu Arg Leu Leu Val Leu Gly
1               5                   10                  15

Leu Trp Leu Ala Leu Leu Arg Ser Val Ala Gly Glu Gln Ala Pro Gly
                20                  25                  30

Thr Ala Pro Cys Ser Arg Gly Ser Ser Trp Ser Ala Asp Leu Asp Lys
                35                  40                  45

Cys Met Asp Cys Ala Ser Cys Arg Ala Arg Pro His Ser Asp Phe Cys
    50                  55                  60

Leu Gly Cys Ala Ala Ala Pro Pro Ala Pro Phe Arg Leu Leu Trp Pro
65              70                  75                  80

Ile Leu Gly Gly Ala Leu Ser Leu Thr Phe Val Leu Gly Leu Leu Ser
                85                  90                  95

Gly Phe Leu Val Trp Arg Arg Cys Arg Arg Arg Glu Lys Phe Thr Thr
                100                 105                 110

Pro Ile Glu Glu Thr Gly Gly Glu Gly Cys Pro Ala Val Ala Leu Ile
                115                 120                 125

Gln

<210> SEQ ID NO 99
<211> LENGTH: 212
<212> TYPE: PRT
<213> ORGANISM: Homo sapiens

<400> SEQUENCE: 99

Met Asn Ser Phe Ser Thr Ser Ala Phe Gly Pro Val Ala Phe Ser Leu
1               5                   10                  15

Gly Leu Leu Leu Val Leu Pro Ala Ala Phe Pro Ala Pro Val Pro Pro
                20                  25                  30

Gly Glu Asp Ser Lys Asp Val Ala Ala Pro His Arg Gln Pro Leu Thr
                35                  40                  45

Ser Ser Glu Arg Ile Asp Lys Gln Ile Arg Tyr Ile Leu Asp Gly Ile
    50                  55                  60
```

```
Ser Ala Leu Arg Lys Glu Thr Cys Asn Lys Ser Asn Met Cys Glu Ser
 65                  70                  75                  80

Ser Lys Glu Ala Leu Ala Glu Asn Asn Leu Asn Leu Pro Lys Met Ala
             85                  90                  95

Glu Lys Asp Gly Cys Phe Gln Ser Gly Phe Asn Glu Glu Thr Cys Leu
            100                 105                 110

Val Lys Ile Ile Thr Gly Leu Leu Glu Phe Glu Val Tyr Leu Glu Tyr
            115                 120                 125

Leu Gln Asn Arg Phe Glu Ser Ser Glu Glu Gln Ala Arg Ala Val Gln
130                 135                 140

Met Ser Thr Lys Val Leu Ile Gln Phe Leu Gln Lys Lys Ala Lys Asn
145                 150                 155                 160

Leu Asp Ala Ile Thr Thr Pro Asp Pro Thr Thr Asn Ala Ser Leu Leu
                165                 170                 175

Thr Lys Leu Gln Ala Gln Asn Gln Trp Leu Gln Asp Met Thr Thr His
            180                 185                 190

Leu Ile Leu Arg Ser Phe Lys Glu Phe Leu Gln Ser Ser Leu Arg Ala
            195                 200                 205

Leu Arg Gln Met
    210

<210> SEQ ID NO 100
<211> LENGTH: 99
<212> TYPE: PRT
<213> ORGANISM: Homo sapiens

<400> SEQUENCE: 100

Met Thr Ser Lys Leu Ala Val Ala Leu Leu Ala Ala Phe Leu Ile Ser
 1               5                  10                  15

Ala Ala Leu Cys Glu Gly Ala Val Leu Pro Arg Ser Ala Lys Glu Leu
             20                  25                  30

Arg Cys Gln Cys Ile Lys Thr Tyr Ser Lys Pro Phe His Pro Lys Phe
            35                  40                  45

Ile Lys Glu Leu Arg Val Ile Glu Ser Gly Pro His Cys Ala Asn Thr
 50                  55                  60

Glu Ile Ile Val Lys Leu Ser Asp Gly Arg Glu Leu Cys Leu Asp Pro
 65                  70                  75                  80

Lys Glu Asn Trp Val Gln Arg Val Val Glu Lys Phe Leu Lys Arg Ala
             85                  90                  95

Glu Asn Ser
```

BISPECIFIC ANTIBODIES AGAINST HUMAN TWEAK AND HUMAN IL17 AND USES THEREOF

CROSS REFERENCE TO RELATED APPLICATIONS

This application is a continuation of International Application No. PCT/EP2013/056970 having an international filing date of Apr. 3, 2013, the entire contents of which are incorporated herein by reference, and which claims benefit under 35 U.S.C. §119 to European Patent Application No. 12163396.0, filed Apr. 5, 2012.

SEQUENCE LISTING

The instant application contains a Sequence Listing submitted via EFS-Web. Said ASCII copy, created on Sep. 25, 2014, is named P30945USSeqList.txt, and is 163,904 bytes in size.

The present invention relates to Bispecific antibodies against human TWEAK and human IL17 (bispecific TWEAK-IL17 antibodies), methods for their production, pharmaceutical compositions containing said antibodies, and uses thereof.

BACKGROUND OF THE INVENTION

Human TWEAK (UniProtKB O43508, TNF-related weak inducer of apoptosis; SEQ ID NO: 68) is a cell surface associated type II transmembrane protein. TWEAK is described in Chicheportiche, Y., et al., J. Biol. Chem. 272 (1997) 32401-32410; Marsters, S. A., et al., Curr. Biol. 8 (1998) 525-528; Lynch, C. N., et al., J. Biol. Chem. 274 (1999) 8455-8459. The active form of TWEAK is a soluble homotrimer. Human and murine TWEAK show 93% sequence identity in receptor binding domain. The TWEAK receptor Fn14 (fibroblast growth factor inducible 14 kDa protein) is a 129 amino acid (aa) type I transmembrane protein consisting of one single cysteine rich domain in ligand binding domain (SEQ ID NO: 98). Signaling of TWEAK occurs via NF-KB pathway activation. TWEAK mRNA is expressed in a variety of tissues and found in most major organs like heart, brain, skeletal muscle, and pancreas, tissues related to the immune system like spleen, lymph nodes, and thymus. Fn14 mRNA has been detected in heart, brain, lung, placenta, vascular EC and smooth muscle cells. TWEAK-null and Fn14-null knockout mice are viable, healthy and fertile and have more natural killer cells and display an enhanced innate inflammatory response. TWEAK is involved in apoptosis, proliferation, angiogenesis, ischemic penumbra, cerebral edema, multiple sclerosis.

Anti-TWEAK antibodies are mentioned in WO 1998/005783, WO 2000/042073, WO 2003/086311, WO 2006/130429, WO 2006/130374, WO 2006/122187, WO 2006/089095, WO 2006/088890, WO 2006/052926.

Human IL-17A (CTLA-8, Swiss Prot Q16552, further named as IL-17 or IL17; SEQ ID NO: 70)) is a pro-inflammatory cytokine produced by a subset of memory T cells (called Th17) that has been implicated in the pathogenesis of MS. IL-17A plays a role in the induction of other inflammatory cytokines, chemokines and adhesion molecules. Treatment of animals with IL-17A neutralizing antibodies decreases disease incidence and severity in autoimmune encephalomyelitis (Komiyama, Y. et al., J. Immunol. 177 (2006) 566-573). IL-17A is over-expressed in the cerebrospinal fluid of MS patients (Hellings, P. W. et al., Am. J. Resp. Cell Mol. Biol. 28 (2003) 42-50; Matusevicius, D. et al., Multiple Sclerosis 5 (1999) 101-104; WO 2005/051422). In addition, IL-17A neutralizing antibodies reduce severity and incidence of mouse RA model of collagen induced arthritis, and high levels of IL-17A can be detected in the synovial fluid of inflamed joints from RA patients (Ziolkowska, M,. et al., J. Immunol. 164 (2000) 2832-2838; Kotake, S., et al., J. Clin. Invest. 103 (1999) 1345-1352; Hellings, P. W., et al., Am. J. Resp. Cell Mol. Biol. 28 (2003) 42-50).

WO 96/17939, U.S. Pat. No. 5,716,623; WO 95/18826; WO 97/15320; WO 99/35276 and WO 00/69436 WO 95/18826 U.S. Pat. No. 6,274,711, U.S. Pat. No. 6,274,711, WO 97/15320, U.S. Pat. No. 6,063,372, WO 2006/013107 and WO 2008/02115 relate to IL-17A and antibodies against IL-17A. WO 2010/102251 relates IL17 binding proteins.

Bispecific Antibodies

A wide variety of recombinant antibody formats have been developed in the recent past, e.g. tetravalent bispecific antibodies by fusion of, e.g., an IgG antibody format and single chain domains (see e.g. Coloma, M. J., et al., Nature Biotech 15 (1997) 159-163; WO 2001/077342; and Morrison, S. L., Nature Biotech 25 (2007) 1233-1234).

Also several other new formats wherein the antibody core structure (IgA, IgD, IgE, IgG or IgM) is no longer retained such as dia-, tria- or tetrabodies, minibodies, several single chain formats (scFv, Bis-scFv), which are capable of binding two or more antigens, have been developed (Holliger, P., et al., Nature Biotech 23 (2005) 1126-1136; Fischer, N., Léger, O., Pathobiology 74 (2007) 3-14; Shen, J., et al., Journal of Immunological Methods 318 (2007) 65-74; Wu, C., et al., Nature Biotech. 25 (2007) 1290-1297).

All such formats use linkers either to fuse the antibody core (IgA, IgD, IgE, IgG or IgM) to a further binding protein (e.g. scFv) or to fuse e.g. two Fab fragments or scFvs (Fischer, N., Léger, O., Pathobiology 74 (2007) 3-14). It has to be kept in mind that one may want to retain effector functions, such as e.g. complement-dependent cytotoxicity (CDC) or antibody dependent cellular cytotoxicity (ADCC), which are mediated through the Fc receptor binding, by maintaining a high degree of similarity to naturally occurring antibodies.

In WO 2007/024715 are reported dual variable domain immunoglobulins as engineered multivalent and multispecific binding proteins. A process for the preparation of biologically active antibody dimers is reported in U.S. Pat. No. 6,897,044. Multivalent FV antibody construct having at least four variable domains which are linked with each over via peptide linkers are reported in U.S. Pat. No. 7,129,330. Dimeric and multimeric antigen binding structures are reported in US 2005/0079170. Tri- or tetra-valent monospecific antigen-binding protein comprising three or four Fab fragments bound to each other covalently by a connecting structure, which protein is not a natural immunoglobulin are reported in U.S. Pat. No. 6,511,663. In WO 2006/020258 tetravalent bispecific antibodies are reported that can be efficiently expressed in prokaryotic and eukaryotic cells, and are useful in therapeutic and diagnostic methods. A method of separating or preferentially synthesizing dimers which are linked via at least one interchain disulfide linkage from dimers which are not linked via at least one interchain disulfide linkage from a mixture comprising the two types of polypeptide dimers is reported in US 2005/0163782. Bispecific tetravalent receptors are reported in U.S. Pat. No. 5,959,083. Engineered antibodies with three or more functional antigen binding sites are reported in WO 2001/077342.

Multispecific and multivalent antigen-binding polypeptides are reported in WO 1997/001580. WO 1992/004053 reports homoconjugates, typically prepared from monoclonal antibodies of the IgG class which bind to the same antigenic determinant are covalently linked by synthetic cross-linking. Oligomeric monoclonal antibodies with high avidity for antigen are reported in WO 1991/06305 whereby the oligomers, typically of the IgG class, are secreted having two or more immunoglobulin monomers associated together to form tetravalent or hexavalent IgG molecules. Sheep-derived antibodies and engineered antibody constructs are reported in U.S. Pat. No. 6,350,860, which can be used to treat diseases wherein interferon gamma activity is pathogenic. In US 2005/0100543 are reported targetable constructs that are multivalent carriers of bi-specific antibodies, i.e., each molecule of a targetable construct can serve as a carrier of two or more bi-specific antibodies. Genetically engineered bispecific tetravalent antibodies are reported in WO 1995/009917. In WO 2007/109254 stabilized binding molecules that consist of or comprise a stabilized scFv are reported.

WO 2008/106131 relates to bispecific antibodies against IL23 and IL17 or TNF. WO 2007/027761 relates to bispecific antibodies against IL23 and IL17. WO 2010/003108 relates TNFalpha antagonist multitarget binding proteins.

SUMMARY OF THE INVENTION

One aspect of the invention is a bispecific antibody comprising a first antigen-binding site that specifically binds to human TWEAK and a second antigen-binding site that specifically binds to human IL17.

In one embodiment of the invention the bispecific antibody inhibits
a) TWEAK induced proliferation of human fibroblast-like synoviocytes-rheumatoid arthritis (HFLS-RA) with an IC50 value of 0.2 nM or lower; and
b) IL17 induced IL6 cytokine stimulation of human fibroblast-like synoviocytes-rheumatoid arthritis (HFLS-RA) with an IC50 value of 3.0 nM or lower; and
c) IL17 induced IL8 cytokine stimulation of human fibroblast-like synoviocytes-rheumatoid arthritis (HFLS-RA) with an IC50 value of 2.0 nM or lower.

In one embodiment of the invention the bispecific antibody comprising a first antigen-binding site that specifically binds to human TWEAK and a second antigen-binding site that specifically binds to human IL17 is a bivalent, bispecific antibody.

In one embodiment of the invention the bispecific antibody comprising a first antigen-binding site that specifically binds to human TWEAK and a second antigen-binding site that specifically binds to human IL17 is characterized in that
  i) said first antigen-binding site comprises
   a) CDR1H of SEQ ID NO:17, CDR2H of SEQ ID NO:18, CDR3H of SEQ ID NO:19, and CDR1L of SEQ ID NO:20, CDR2L of SEQ ID NO:21, CDR3L of SEQ ID NO:22; or
   b) CDR1H of SEQ ID NO:1, CDR2H of SEQ ID NO:2, CDR3H of SEQ ID NO:3, and CDR1L of SEQ ID NO:4, CDR2L of SEQ ID NO:5, CDR3L of SEQ ID NO:6; or
   c) CDR1H of SEQ ID NO:9, CDR2H of SEQ ID NO:10, CDR3H of SEQ ID NO:11, and CDR1L of SEQ ID NO:12, CDR2L of SEQ ID NO:13, CDR3L of SEQ ID NO:14; and
  ii) said second antigen-binding site comprises
   CDR1H of SEQ ID NO:47, CDR2H of SEQ ID NO:48, CDR3H of SEQ ID NO:49, and CDR1L of SEQ ID NO:50, CDR2L of SEQ ID NO:51, CDR3L of SEQ ID NO:52.

In one embodiment of the invention is a chimeric or humanized variant of the such bispecific antibody.

In one embodiment of the invention the bispecific antibody comprising a first antigen-binding site that specifically binds to human TWEAK and a second antigen-binding site that specifically binds to human IL17 is characterized in that
  i) said first antigen-binding site comprises
   a variable heavy chain domain (VH) of SEQ ID NO:25, of SEQ ID NO:26, of SEQ ID NO:27, of SEQ ID NO:28, of SEQ ID NO:29, of SEQ ID NO:30, of SEQ ID NO:31, of SEQ ID NO:32, of SEQ ID NO:33, of SEQ ID NO:34, or of SEQ ID NO:35, and a variable light chain domain of SEQ ID NO:26, of SEQ ID NO:37, of SEQ ID NO:38, of SEQ ID NO:39, of SEQ ID NO:40, of SEQ ID NO:41, of SEQ ID NO:42, of SEQ ID NO:43, of SEQ ID NO:44, of SEQ ID NO:45, or of SEQ ID NO:46; and
  ii) said second antigen-binding site comprises
   a variable heavy chain domain (VH) of SEQ ID NO:55, or of SEQ ID NO:56, and a variable light chain domain of SEQ ID NO:57, or of SEQ ID NO:58.

In one embodiment of the invention the bispecific antibody comprising a first antigen-binding site that specifically binds to human TWEAK and a second antigen-binding site that specifically binds to human IL17 is characterized in that
  i) said first antigen-binding site comprises
   a variable heavy chain domain (VH) of SEQ ID NO:28, and a variable light chain domain of SEQ ID NO:37; and
  ii) said second antigen-binding site comprises
   a) a variable heavy chain domain (VH) of SEQ ID NO:56, and a variable light chain domain of SEQ ID NO:58; or
   b) a variable heavy chain domain (VH) of SEQ ID NO:55, and a variable light chain domain of SEQ ID NO:57.

In one embodiment of the invention the bispecific antibody comprising a first antigen-binding site that specifically binds to human TWEAK and a second antigen-binding site that specifically binds to human IL17 is characterized in that
  i) said first antigen-binding site comprises
   a variable heavy chain domain (VH) of SEQ ID NO:28, and a variable light chain domain of SEQ ID NO:37; and
  ii) said second antigen-binding site comprises
   a variable heavy chain domain (VH) of SEQ ID NO:56, and a variable light chain domain of SEQ ID NO:58.

In one embodiment of the invention the bispecific antibody comprising a first antigen-binding site that specifically binds to human TWEAK and a second antigen-binding site that specifically binds to human IL17 is characterized in that
  i) said first antigen-binding site comprises
   a variable heavy chain domain (VH) of SEQ ID NO:28, and a variable light chain domain of SEQ ID NO:37; and
  ii) said second antigen-binding site comprises
   a variable heavy chain domain (VH) of SEQ ID NO:55, and a variable light chain domain of SEQ ID NO:57.

In one embodiment the bispecific antibody which binds to TWEAK and IL17 and being characterized by the above mentioned amino acid sequences and amino acid sequence fragments is of human IgG1 isotype, in one embodiment with mutations L234A and L235A, in one embodiment with mutations L234A, L235A and P329G.

In one embodiment the bispecific antibody which binds to TWEAK and IL17 and being characterized by the above mentioned amino acid sequences and amino acid sequence fragments is of human IgG4 isotype, in one embodiment with mutations S228P and L235E, in one embodiment with mutations S228P, L235E and P329G.

A further embodiment of the invention is a pharmaceutical composition comprising a bispecific antibody according to the invention.

A further embodiment of the invention is the use of a bispecific antibody according to the invention for the manufacture of a pharmaceutical composition.

A further embodiment of the invention is a nucleic acid encoding a bispecific antibody according to the invention.

A further embodiment of the invention is a nucleic acid encoding a heavy chain variable domain and/or a light chain variable domain of a bispecific antibody according to the invention.

The invention further provides expression vectors containing nucleic acid according to the invention capable of expressing said nucleic acid in a prokaryotic or eukaryotic host cell, and host cells containing such vectors for the recombinant production of such an antibody.

The invention further comprises a prokaryotic or eukaryotic host cell comprising a vector according to the invention.

The invention further comprises a method for the production of a recombinant chimeric, human or humanized antibody according to the invention, characterized by expressing a nucleic acid according to the invention in a prokaryotic or eukaryotic host cell and recovering said antibody from said cell or the cell culture supernatant. The invention further comprises the antibody obtainable by such a recombinant method.

Antibodies according to the invention show benefits for patients in need of a TWEAK and IL17 targeting therapy. The antibodies according to the invention have new and inventive properties causing a benefit for a patient suffering from a cancer disease, especially suffering from colon, lung, or pancreatic cancer or from inflammatory diseases, especially from autoimmune diseases, rheumatoid arthritis, psoratic arthritis, muscle diseases, e.g. muscular dystrophy, multiple sclerosis, chronic kidney diseases, bone diseases, e.g. bone degeneration in multiple myeloma, systemic lupus erythematosus, lupus nephritis, and vascular injury.

A further embodiment of the invention is a bispecific antibody according to the invention for use in the treatment of cancer, inflammatory diseases, autoimmune diseases, rheumatoid arthritis, psoratic arthritis, muscle diseases, e.g. muscular dystrophy, multiple sclerosis, chronic kidney diseases, bone diseases, e.g. bone degeneration in multiple myeloma, systemic lupus erythematosus, lupus nephritis, and vascular injury, especially for the treatment of systemic lupus erythematosus, lupus nephritis.

A further embodiment of the invention is a bispecific antibody according to the invention for manufacture of a medicament for the treatment of cancer, inflammatory diseases, autoimmune diseases, rheumatoid arthritis, psoratic arthritis, muscle diseases, e.g. muscular dystrophy, multiple sclerosis, chronic kidney diseases, bone diseases, e.g. bone degeneration in multiple myeloma, systemic lupus erythematosus, lupus nephritis, and vascular injury, especially for the treatment of systemic lupus erythematosus, lupus nephritis.

The invention further provides a method for treating a patient suffering from cancer, especially from colon, lung, or pancreatic cancer or from inflammatory diseases, especially from autoimmune diseases, rheumatoid arthritis, psoratic arthritis, muscle diseases, e.g. muscular dystrophy, multiple sclerosis, chronic kidney diseases, bone diseases, e.g. bone degeneration in multiple myeloma, systemic lupus erythematosus, lupus nephritis, and vascular injury, comprising administering to a patient diagnosed as having such a disease (and therefore being in need of such a therapy) an effective amount of the bispecific antibody which binds to TWEAK and IL17 according to the invention. The antibody is administered preferably in a pharmaceutical composition.

The invention further comprises a pharmaceutical composition comprising an antibody according to the invention, optionally together with a buffer and/or an adjuvant useful for the formulation of antibodies for pharmaceutical purposes.

The invention further provides a pharmaceutical composition comprising an antibody according to the invention in a pharmaceutically acceptable carrier. In one embodiment, the pharmaceutical composition may be included in an article of manufacture or kit.

The bispecific antibodies according to the invention show benefits for human patients in need of a TWEAK and IL17 targeting therapy and have valuable properties.

The antibodies according to the invention have valuable properties causing a benefit for a patient suffering from such a disease, especially suffering from inflammatory diseases such as rheumatoid arthritis or lupus nephritis. Such valuable properties include the simultaneous inhibition of both TWEAK and IL17 leading to complementary treatment benefits. There is a persistent high unmet medical need in RA as many patients fail to achieve a target of remission. Bispecific antibodies targeting both TWEAK and IL17 offer an opportunity for improved efficacy by inhibiting IL-17 and TWEAK thus providing complementary anti-inflammatory and anti-angiogenic activity and optimal impact on bone formation/resorption. TWEAK expression is significantly increased in synovial tissue of RA and PsA patients—mainly in $CD55^+$ synoviocytes and $CD168^+$ macrophages. (Van Kuijk, et al., Ann Rheum Dis 69 (2010) 301-304). IL-17A is produced in inflamed synovial tissue with lower IL-17 in TNF responders and higher IL-17 levels in TNF-non-responders (Moran, et al., Arthritis & Rheumatism 11 (2009) R113). In addition, available data supports a role for IL-17 and TWEAK in kidney inflammation with effects on mesangial cells, tubular epithelial cells, endothelial cells, elevated chemokines, cytokines, neutrophil infiltration and positive correlations of IL-17 and TWEAK with disease activity. Urinary TWEAK levels correlate with renal SLEDAI scores, TWEAK is elevated during flares and specific to renal disease (Schwartz, et al., J Autoimmunity 27 (2006) 242-25). In addition, TWEAK blockade reduces kidney inflammation in a model of acute kidney injury (AKI) (Sanz, et al., J Amer Soc Nephrol 19 (2008) 695-703). Elevated IL-17 is detected in tissues from lupus patients and IL-17 is detected in affected kidneys from patients with SLE (Crispin, et al., J Immunol. 181 (2008) 8761-8766).

Low viscosity and high stability in terms of aggregation (>55° C.) makes such antibodies suitable for high concentration formulation for a possible subcutaneous application (He, F., et al., J Pharm Sci. 100 (2010) 1330-1340).

In one embodiment the bispecific antibodies according to the invention are additionally characterized by one or more of the following properties (as determined in Examples 4, 10, 11, 16, 17 and 19): the bispecific antibody a) shows no cross reactivity with IL17B, IL17C, IL17D, IL17F (which means that the binding to IL17B, IL17C, IL17D and IL17F is 0% compared to the binding to IL17A, which is set as 100%);

b) inhibits IL17 induced IL8 cytokine stimulation of CCD-25SK cells with an IC50 value of 2.0 nM or lower (e.g. with an IC50 value between 2.0 nM and 0.0 nM);
c) inhibits IL17 induced IL6 cytokine stimulation of CCD-25SK cells with an IC50 value of 5.0 nM or lower (e.g. with an IC50 value between 5.0 nM and 0.0 nM); preferably with an IC50 value of 2.0 nM or lower;
d) human TWEAK/human Fn14 interaction with an IC50 value of 4.0 [ng/ml] or lower (e.g. with an IC50 value between 4.0 [ng/ml] and 0.0 [ng/ml]); preferably with an IC50 value of 3.0 [ng/ml] or lower;
e) binds to human TWEAK with an KD value of binding affinity of 0.1 nM or lower, and binds to human IL-17 with an KD value of binding affinity of 0.3 nM or lower; and/or
f) is capable to simultaneously bind to human <TWEAK> and human <IL17>, wherein the signal intensity (in RU) (in a surface plasmon resonance assay) of the binding of the bispecific TWEAK/IL17 antibody to a 1:1 mixture from human <TWEAK> and human <IL17> is at least the same or higher compared to the sum of a) the signal intensity (in RU) of the binding of the bispecific TWEAK/IL17 antibody to human <TWEAK> alone and b) the signal intensity (in RU) of the binding of the bispecific TWEAK/IL17 antibody to human <IL17> alone.

DETAILED DESCRIPTION OF THE INVENTION

Figure 1A:
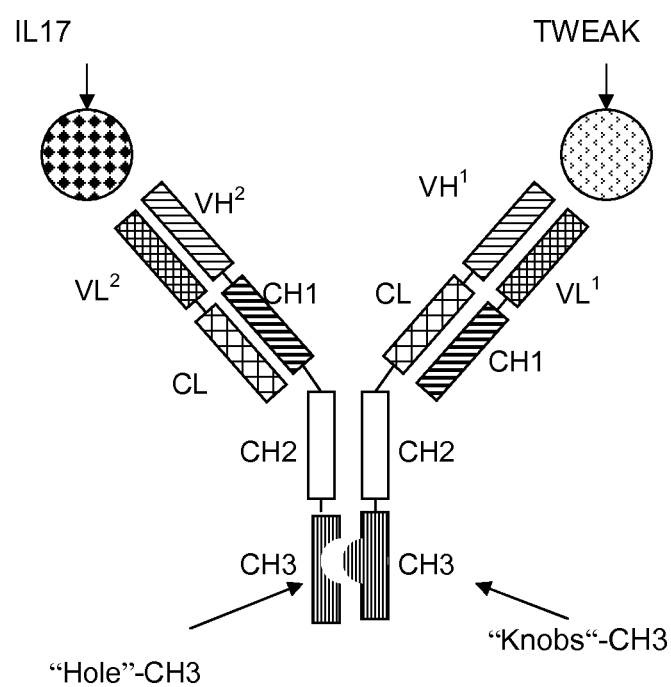
FIGS. 1a and b Two exemplary bispecific, bivalent antibody formats for the bispecific <TWEAK/IL17> antibodies according to the invention are shown.

As used herein, "antibody" refers to a binding protein that comprises antigen-binding sites. The terms "binding site" or "antigen-binding site" as used herein denotes the region(s) of an antibody molecule to which a ligand (i. e. the antigen) actually binds. The term "antigen-binding site" include antibody heavy chain variable domains (VH) and/or an antibody light chain variable domains (VL), or pairs of VH/VL, and can be derived from whole antibodies or antibody fragments such as single chain Fv, a VH domain and/or a VL domain, Fab, or (Fab)2. In one embodiment of the current invention each of the antigen-binding sites comprises an antibody heavy chain variable domain (VH) and/or an antibody light chain variable domain (VL), and preferably is formed by a pair consisting of an antibody light chain variable domain (VL) and an antibody heavy chain variable domain (VH). The antibody according to the invention is preferably a humanized antibody, chimeric antibody, or further genetically engineered antibody as long as the characteristic properties according to the invention are retained.

The antigen-binding site, and especially heavy chain variable domains (VH) and/or antibody light chain variable domains (VL), that specifically bind to human TWEAK can be derived a) from known anti-TWEAK antibodies as described in e.g. WO 1998/005783, WO 2000/042073, WO 2003/086311, WO 2006/130429, WO 2006/130374, WO 2006/122187, WO 2006/089095, WO 2006/088890, WO 2006/052926, WO 2010/115555 or PCT Application No. PCT/EP2011/067070; or b) from new anti-TWEAK antibodies obtained e.g. by de novo immunization methods using inter alia either the human TWEAK protein or nucleic acid or fragments thereof or by phage display methods.

The antigen-binding site, and especially heavy chain variable domains (VH) and/or antibody light chain variable domains (VL), that specifically bind to human IL17 can be derived a) from known anti-IL17 antibodies as described in e.g. WO 96/17939, U.S. Pat. No. 5,716,623; WO 95/18826; WO 97/15320; WO 99/35276, WO 00/69436, WO 95/18826, U.S. Pat. No. 6,274,711, U.S. Pat. No. 6,063,372, WO 2006/013107, WO 2008/02115, WO 2010/102251 or WO 2010/034443; or b) from new anti-IL17 antibodies obtained e.g. by de novo immunization methods using inter alia either the human IL17 protein or nucleic acid or fragments thereof or by phage display methods.

Human TWEAK (UniProtKB 043508, TNF-related weak inducer of apoptosis; SEQ ID NO: 68) is a cell surface associated type II transmembrane protein. TWEAK is described in Chicheportiche, Y., et al., J. Biol. Chem. 272 (1997) 32401-32410; Marsters, S. A., et al., Curr. Biol. 8 (1998) 525-528; Lynch, C. N., et al., J. Biol. Chem. 274 (1999) 8455-8459. The active form of TWEAK is a soluble homotrimer. Human and murine TWEAK show 93% sequence identity in receptor binding domain. The TWEAK receptor Fn14 (fibroblast growth factor inducible 14 kDa protein) is a 129 aa type I transmembrane protein consisting of one single cysteine rich domain in ligand binding domain (SEQ ID NO: 98). Signaling of TWEAK occurs via NF-KB pathway activation. TWEAK mRNA is expressed in a variety of tissues and found in most major organs like heart, brain, skeletal muscle, and pancreas, tissues related to the immune system like spleen, lymph nodes, and thymus. Fn14 mRNA has been detected in heart, brain, lung, placenta, vascular EC and smooth muscle cells. TWEAK-null and Fn14-null knockout mice are viable, healthy and fertile and have more natural killer cells and display an enhanced innate inflammatory response. TWEAK is involved in apoptosis, proliferation, angiogenesis, ischemic penumbra, cerebral edema, multiple sclerosis.

Human IL-17A (CTLA-8, Swiss Prot Q16552, further named as IL-17. IL17; SEQ ID NO: 70)) is a pro-inflammatory cytokine produced by a subset of memory T cells (called Th17) that has been implicated in the pathogenesis of MS. IL-17A plays a role in the induction of other inflammatory cytokines, chemokines and adhesion molecules. Treatment of animals with IL-17A neutralizing antibodies decreases disease incidence and severity in autoimmune encephalomyelitis (Komiyama, Y. et al., J. Immunol. 177 (2006) 566-573). IL-17A is over-expressed in the cerebrospinal fluid of MS patients (Hellings, P. W. et al., Am. J. Resp. Cell Mol. Biol. 28 (2003) 42-50; Matusevicius, D. et al., Multiple Sclerosis 5 (1999) 101-104; WO 2005/051422). In addition, IL-17A neutralizing antibodies reduce severity and incidence of mouse RA model of collagen induced arthritis, and high levels of IL-17A can be detected in the synovial fluid of inflamed joints from RA patients (Ziolkowska, M. et al., J. Immunol. 164 (2000) 2832-2838; Kotake, S., et al., J. Clin. Invest. 103 (1999) 1345-1352; Hellings, P. W. et al., Am. J. Resp. Cell Mol. Biol. 28 (2003) 42-50).

Antibody specificity refers to selective recognition of the antibody for a particular epitope of an antigen. Natural antibodies, for example, are monospecific.

"Bispecific antibodies" according to the invention are antibodies which have two different antigen-binding specificities. Where an antibody has more than one specificity, the recognized epitopes may be associated with a single antigen or with more than one antigen. Antibodies of the present invention are specific for two different antigens, i.e. TWEAK as first antigen and IL17 as second antigen.

The term "monospecific" antibody as used herein denotes an antibody that has one or more binding sites each of which bind to the same epitope of the same antigen.

The term "valent" as used within the current application denotes the presence of a specified number of binding sites in an antibody molecule. As such, the terms "bivalent", "tetravalent", and "hexavalent" denote the presence of two binding site, four binding sites, and six binding sites, respectively, in an antibody molecule. The bispecific antibodies according to the invention are at least "bivalent" and may be "trivalent" or "multivalent" (e.g. "tetravalent" or "hexavalent"). In one embodiment the bispecific antibody according to the invention is bivalent, trivalent or tetravalent. In one embodiment said bispecific antibody is bivalent. In one embodiment said bispecific antibody is trivalent. In one embodiment said bispecific antibody is tetravalent.

Antibodies of the present invention have two or more binding sites and are bispecific. That is, the antibodies may be bispecific even in cases where there are more than two binding sites (i.e. that the antibody is trivalent or multivalent). Bispecific antibodies of the invention include, for example, multivalent single chain antibodies, diabodies and triabodies, as well as antibodies having the constant domain structure of full length antibodies to which further antigen-binding sites (e.g., single chain Fv, a VH domain and/or a VL domain, Fab, or (Fab)2,) are linked via one or more peptide-linkers. The antibodies can be full length from a single species, or be chimerized or humanized. For an antibody with more than two antigen binding sites, some binding sites may be identical, so long as the protein has binding sites for two different antigens. That is, whereas a first binding site is specific for a TWEAK, a second binding site is specific for IL17, and vice versa.

The terms "monoclonal antibody" or "monoclonal antibody composition" as used herein refer to a preparation of antibody molecules of a single amino acid composition.

The term "humanized antibody" refers to antibodies in which the framework and/or "complementary determining regions" (CDR) have been modified to comprise the CDR of an immunoglobulin of different species as compared to that of the parent immunoglobulin. In a preferred embodiment, a non-human (e.g. mouse, rabbit or hamster) CDR is grafted into the framework region of a human antibody to prepare the "humanized antibody". See, e.g., Riechmann, L., et al., Nature 332 (1988) 323-327; and Neuberger, M. S., et al., Nature 314 (1985) 268-270.

The term "chimeric antibody" refers to a monoclonal antibody comprising a variable region, i.e., binding region, from mouse and at least a portion of a constant region derived from a different source or species, usually prepared by recombinant DNA techniques. Chimeric antibodies comprising for example a mouse variable region and a human constant region. Such mouse/human chimeric antibodies are the product of expressed immunoglobulin genes comprising DNA segments encoding rat immunoglobulin variable regions and DNA segments encoding human immunoglobulin constant regions. Other forms of "chimeric antibodies" encompassed by the present invention are those in which the class or subclass has been modified or changed from that of the original antibody. Such "chimeric" antibodies are also referred to as "class-switched antibodies." Methods for producing chimeric antibodies involve conventional recombinant DNA and gene transfection techniques now well known in the art. See, e.g., Morrison, S. L., et al., Proc. Natl. Acad Sci. USA 81 (1984) 6851-6855; U.S. Pat. Nos. 5,202, 238 and 5,204,244.

As used herein, the terms, "binds to", "binding" or "specifically binding" refers to the binding of the bispecific antibody to an epitope of the antigen (either human TWEAK or human IL17) with sufficient affinity such that the antibody is useful as a therapeutic agent in targeting human TWEAK and/or human IL17 according to the invention. The binding of the bispecific antibody to an epitope of the antigen (either human TWEAK or human IL17) can be measured in an in vitro assay, preferably in an plasmon resonance assay (e.g. BIAcore, GE-Healthcare Uppsala, Sweden) with purified wild-type human antigen (preferably with IL17A homodimer for the human IL17 antigen) (see e.g. Example 19). The affinity of the binding is defined by the terms ka (rate constant for the association of the antibody from the antibody/antigen complex), kd (dissociation constant), and KD (kd/ka). A bispecific antibody comprising a first antigen-binding site that specifically binds to human TWEAK and a second antigen-binding site that specifically binds to human IL17 refers to bispecific antibody with a first antigen-binding site which specifically binds to human TWEAK with a binding affinity (KD) of $1.0 \times 10^{-8}$ M or less, e.g. from $1.0 \times 10^{-8}$ M to $1.0 \times 10^{-13}$ M (in one embodiment from $1.0 \times 10^{-9}$ M to $1.0 \times 10^{-13}$ M), and with a second antigen-binding site which specifically binds to human IL17 with a binding affinity (KD) of $1.0 \times 10^{-8}$ M or less, e.g. from $1.0 \times 10^{-8}$ M to $1.0 \times 10^{-13}$ M (in one embodiment from $1.0 \times 10^{-9}$ M to $1.0 \times 10^{-13}$ M).

The term "epitope" denotes a protein determinant capable of specifically binding to an antibody. Epitopes usually consist of chemically active surface groupings of molecules such as amino acids or sugar side chains and usually epitopes have specific three dimensional structural characteristics, as well as specific charge characteristics. Conformational and nonconformational epitopes are distinguished in that the binding to the former but not the latter is lost in the presence of denaturing solvents.

One embodiment of the invention is a bispecific antibody comprising a first antigen-binding site that specifically binds to human TWEAK and a second antigen-binding site that specifically binds to human IL17, characterized in that
a) the first antigen-binding site binds to the same epitope on human TWEAK as an antibody which comprises a CDR1H of SEQ ID NO:17, CDR2H of SEQ ID NO:18, CDR3H of SEQ ID NO:19, and CDR1L of SEQ ID NO:20, CDR2L of SEQ ID NO:21, CDR3L of SEQ ID NO:22; and
b) the second antigen-binding site binds to the same epitope on human IL17 as an antibody which comprises a CDR1H of SEQ ID NO:47, CDR2H of SEQ ID NO:48, CDR3H of SEQ ID NO:49, and CDR1L of SEQ ID NO:50, CDR2L of SEQ ID NO:51, CDR3L of SEQ ID NO:52.

One embodiment of the invention is a bispecific antibody comprising a first antigen-binding site that specifically binds to human TWEAK and a second antigen-binding site that specifically binds to human IL17, characterized in that
a) the first antigen-binding site binds to the same epitope on human TWEAK as an antibody which comprises a variable heavy chain domain (VH) of SEQ ID NO:28, and a variable light chain domain of SEQ ID NO:37; and
b) the second antigen-binding site binds to the same epitope on human IL17 as an antibody which comprises a variable heavy chain domain (VH) of SEQ ID NO:56, and a variable light chain domain of SEQ ID NO:58.

One embodiment of the invention is a bispecific antibody comprising a first antigen-binding site that specifically binds to human TWEAK and a second antigen-binding site that specifically binds to human IL17, characterized in that
a) the first antigen-binding site competes for binding to the same epitope on human TWEAK as an antibody which comprises a CDR1H of SEQ ID NO:17, CDR2H of SEQ ID NO:18, CDR3H of SEQ ID NO:19, and CDR1L of SEQ ID NO:20, CDR2L of SEQ ID NO:21, CDR3L of SEQ ID NO:22; and
b) the second antigen-binding site competes for binding to the same epitope on human IL17 as an antibody which comprises a CDR1H of SEQ ID NO:47, CDR2H of SEQ ID NO:48, CDR3H of SEQ ID NO:49, and CDR1L of SEQ ID NO:50, CDR2L of SEQ ID NO:51, CDR3L of SEQ ID NO:52.

One embodiment of the invention is a bispecific antibody comprising a first antigen-binding site that specifically binds to human TWEAK and a second antigen-binding site that specifically binds to human IL17, characterized in that
a) the first antigen-binding site competes for binding to the same epitope on human TWEAK as an antibody which comprises a variable heavy chain domain (VH) of SEQ ID NO:28, and a variable light chain domain of SEQ ID NO:37; and
b) the second antigen-binding site competes for binding to the same epitope on human IL17 as an antibody which comprises a variable heavy chain domain (VH) of SEQ ID NO:56, and a variable light chain domain of SEQ ID NO:58.

Antibodies which compete for binding to the same epitope (and thus are likely to bind to the same epitope) cane identified by Surface Plasmon Resonance competition assay as described e.g. in Example 7.

The "variable domain" (variable domain of a light chain ($V_L$), variable domain of a heavy chain ($V_H$)) as used herein denotes each of the pair of light and heavy chain domains which are involved directly in binding the antibody to the antigen. The variable light and heavy chain domains have the same general structure and each domain comprises four framework (FR) regions whose sequences are widely conserved, connected by three "hypervariable regions" (or complementary determining regions, CDRs). The framework regions adopt a β-sheet conformation and the CDRs may form loops connecting the β-sheet structure. The CDRs in each chain are held in their three-dimensional structure by the framework regions and form together with the CDRs from the other chain the antigen binding site. The antibody's heavy and light chain CDR3 regions play a particularly important role in the binding specificity/affinity of the antibodies according to the invention and therefore provide a further object of the invention.

The term "antigen-binding portion of an antibody" when used herein refers to the amino acid residues of an antibody which are responsible for antigen-binding. The antigen-binding portion of an antibody comprises amino acid residues from the "complementary determining regions" or "CDRs". "Framework" or "FR" regions are those variable domain regions other than the hypervariable region residues as herein defined. Therefore, the light and heavy chain variable domains of an antibody comprise from N- to C-terminus the domains FR1, CDR1, FR2, CDR2, FR3, CDR3, and FR4. Especially, CDR3 of the heavy chain is the region which contributes most to antigen binding and defines the antibody's properties. CDR and FR regions are determined according to the standard definition of Kabat et al., Sequences of Proteins of Immunological Interest, 5th ed., Public Health Service, National Institutes of Health, Bethesda, Md. (1991) and/or those residues from a "hypervariable loop".

The term "CDR1H" denotes the CDR1 region of the heavy chain variable region calculated according to Kabat (Kabat et al., Sequences of Proteins of Immunological Interest, 5th ed., Public Health Service, National Institutes of Health, Bethesda, Md. (1991)). CDR2L, CDR3H, etc. mean the respective regions from the heavy(H) or light(L) chain. For example, an antigen binding site characterized by comprising CDR1H of SEQ ID NO:3 means that the antigen binding site comprises this amino acid sequence as a heavy chain variable chain CDR1 region in its variable heavy chain. For example, an antigen binding site characterized by comprising CDR1H of SEQ ID NO:1, CDR2H of SEQ ID NO:2, CDR3H of SEQ ID NO:3 means that the antigen binding sites comprises in its heavy chain as sequence of CDR1 SEQ ID NO:1, as sequence of CDR2 SEQ ID NO:2, and as sequence of CDR3 SEQ ID NO:3.

The terms "nucleic acid" or "nucleic acid molecule" as used herein are intended to include DNA molecules and RNA molecules. A nucleic acid molecule may be single-stranded or double-stranded, but preferably is double-stranded DNA.

The term "amino acid" as used within this application denotes the group of naturally occurring carboxy α-amino acids comprising alanine (three letter code: ala, one letter code: A), arginine (arg, R), asparagine (asn, N), aspartic acid (asp, D), cysteine (cys, C), glutamine (gln, Q), glutamic acid (glu, E), glycine (gly, G), histidine (his, H), isoleucine (ile, I), leucine (leu, L), lysine (lys, K), methionine (met, M), phenylalanine (phe, F), proline (pro, P), serine (ser, S), threonine (thr, T), tryptophan (tip, W), tyrosine (tyr, Y), and valine (val, V).

A nucleic acid is "operably linked" when it is placed into a functional relationship with another nucleic acid. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are colinear, and, in the case of a secretory leader, contiguous and in reading frame. However, enhancers do not have to be contiguous. Linking is accomplished by ligation at convenient restriction sites. If such sites do not exist, synthetic oligonucleotide adaptors or linkers are used in accordance with conventional practice.

As used herein, the expressions "cell", "cell line", and "cell culture" are used interchangeably and all such designations include progeny. Thus, the words "transformants" and "transformed cells" include the primary subject cell and cultures derived therefrom without regard for the number of transfers. It is also understood that all progeny may not be precisely identical in DNA content, due to deliberate or inadvertent mutations. Variant progeny that have the same function or biological activity as screened for in the originally transformed cell are included.

The "Fc part" of an antibody is not involved directly in binding of an antibody to an antigen, but exhibits various effector functions. An "Fc part of an antibody" is a term well known to the skilled artisan and defined on the basis of papain cleavage of antibodies. Depending on the amino acid sequence of the constant region of their heavy chains, antibodies or immunoglobulins are divided into the classes:

IgA, IgD, IgE, IgG and IgM, and several of these may be further divided into subclasses (isotypes; the expressions "isotype" or "subclass" are used interchangeable herein), e.g. IgG1, IgG2, IgG3, and IgG4, IgA1, and IgA2. According to the heavy chain constant regions the different classes of immunoglobulins are called α, δ, ε, γ, and μ, respectively. The Fc part of an antibody is directly involved in ADCC (antibody-dependent cell-mediated cytotoxicity) and CDC (complement-dependent cytotoxicity) based on complement activation, C1q binding and Fc receptor binding. Complement activation (CDC) is initiated by binding of complement factor C1q to the Fc part of most IgG antibody subclasses. While the influence of an antibody on the complement system is dependent on certain conditions, binding to C1q is caused by defined binding sites in the Fc part. Such binding sites are known in the state of the art and described, e.g., by Boackle, R. J., et al., Nature 282 (1979) 742-743; Lukas, T. J., et al., J. Immunol. 127 (1981) 2555-2560; Brunhouse, R. and Cebra, J. J., Mol. Immunol. 16 (1979) 907-917; Burton, D. R., et al., Nature 288 (1980) 338-344; Thommesen, J. E., et al., Mol. Immunol. 37 (2000) 995-1004; Idusogie, E. E., et al., J. Immunol. 164 (2000) 4178-4184; Hezareh, M. et al., J. Virology 75 (2001) 12161-12168; Morgan, A., et al., Immunology 86 (1995) 319-324; EP 0 307 434. Such binding sites are, e.g., L234, L235, D270, N297, E318, K320, K322, P331, and P329 (numbering according to EU index of Kabat used for the numbering of the constant domains, Kabat, et al., Sequences of Proteins of Immunological Interest, 5th ed., Public Health Service, National Institutes of Health, Bethesda, Md. (1991)).

Antibodies of subclass IgG1, IgG2 and IgG3 usually show complement activation and C1q and C3 binding, whereas IgG4 does not activate the complement system and does not bind C1q and C3.

In one embodiment the antibody according to the invention is characterized in that the constant chains are of human origin. Such constant chains are well known in the state of the art and e.g. described by Kabat (see e.g. Johnson, G. and Wu, T. T., Nucleic Acids Res. 28 (2000) 214-218 and Kabat et al., Sequences of Proteins of Immunological Interest, 5th ed., Public Health Service, National Institutes of Health, Bethesda, Md. (1991)). For example, useful human heavy chain constant regions comprises an amino acid sequence SEQ ID NO: 61, SEQ ID NO: 62, SEQ ID NO: 63 or SEQ ID NO: 64 (human IgG1 subclass allotypes (Caucasian and Afroamerican or mutants L234A/L235A, and L234A/L235A/P329G), SEQ ID NO: 65, SEQ ID NO: 66, or SEQ ID NO: 67 (human IgG4 subclass or mutants L234A/L235A, and L234A/L235A/P329G). For example, a useful human light chain constant region comprises an amino acid sequence of a kappa-light chain constant region of SEQ ID NO:59 or an amino acid sequence of a lambda-light chain constant region of SEQ ID NO:60. In one embodiment the antibody according to the invention comprises a Fc part derived from human origin and preferably all other parts of the human constant regions. As used herein the term "Fc part derived from human origin" denotes a Fc part which is either a Fc part of a human antibody of the subclass IgG1, IgG2, IgG3 or IgG4, in one embodiment a Fc part from human IgG1 subclass, a mutated Fc part from human IgG1 subclass (preferably with a mutations L234A and L235A, or L234A, L235A and P329G), a Fc part from human IgG4 subclass or a mutated Fc part from human IgG4 subclass (preferably with a mutations S228P and L235E, or S228P, L235E and P329G). In one embodiment the bispecific antibody comprise the human heavy chain constant regions of SEQ ID NO: 61, SEQ ID NO: 62, SEQ ID NO: 63 or SEQ ID NO: 64 (human IgG1 subclass allotypes (Caucasian and Afroamerican or mutants L234A/L235A, and L234A/L235A/P329G), SEQ ID NO: 65, SEQ ID NO: 66, or SEQ ID NO: 67 (human IgG4 subclass or mutants L234A/L235A, and L234A/L235A/P329G) (numbering according to the EU index of Kabat et al., Sequences of Proteins of Immunological Interest, 5th ed., Public Health Service, National Institutes of Health, Bethesda, Md. (1991). These human heavy chain constant regions can comprise additionally modifications and or mutations (see e.g. the knobs and hole mutations as described below or other modification which enhance the heterodimerization. In one embodiment the bispecific antibody comprises two heavy chain constant regions wherein in one of the two CH3 domains the mutations Y349C, T366W and in the other of the two CH3 domains the mutations S354C, T366S, L368A, Y407V are additionally comprised in the amino acid sequences of SEQ ID NO: 61, SEQ ID NO: 62, SEQ ID NO: 63 or SEQ ID NO: 64 (human IgG1 subclass allotypes (Caucasian and Afroamerican or mutants L234A/L235A, and L234A/L235A/P329G), SEQ ID NO: 65, SEQ ID NO: 66, or SEQ ID NO: 67 (human IgG4 subclass or mutants L234A/L235A, and L234A/L235A/P329G) (numbering according to the EU index of Kabat et al., Sequences of Proteins of Immunological Interest, 5th ed., Public Health Service, National Institutes of Health, Bethesda, Md. (1991).

In one embodiment the antibody according to the invention is of human IgG1 subclass or of human IgG4 subclass. In one embodiment the antibody according to the invention is of human IgG1 subclass. In one embodiment the antibody according to the invention is of human IgG4 subclass.

In one embodiment the bispecific antibody specifically binding to human TWEAK and human IL17 according to the invention is a bispecific, bivalent antibody with two different specificities as described e.g. in WO 2009/080251, WO 2009/080252, WO 2009/080253 or Schaefer, W., et al., PNAS 108 (2011) 11187-92 ("CrossMabs" or "domain exchanged antibodies"—see Example 14, and exemplary FIG. 1a; <Tweak-IL-17> #2, <Tweak-IL-17> #24 which have the format described in WO 2009/080253), in WO 2011/117330 ("bispecific one-armed scFab antibodies" see Example 14; <Tweak-IL-17> #4, <Tweak-IL-17> #20, <Tweak-IL-17> #21, <Tweak-IL-17> #23; see also and exemplary FIG. 1a), in Ridgway, J. B., Protein Eng. 9 (1996) 617-621; WO 96/027011; WO 98/050431, Merchant, A. M., et al., Nature Biotech 16 (1998) 677-681; Atwell, S., et al., J. Mol. Biol. 270 (1997) 26-35, EP 1 870 459 A1, Muda, M., et al, Protein Engineering, Design & Selection 24 (2011) 447-454, WO 2010/129304, WO 2011/028952, WO 2012/009544 and the like (which are all incorporated by references).

Typically such bispecific, bivalent antibody often comprise a Fc part and comprise two different heavy chain or heavy chain-like peptides which form heterodimers. To enforce the formation of such heterodimers (and reduce the formation of homodimeric by-products) the CH3 (and/or CH2) domains are modified in way that the formation of the heterodimer is preferred. There are different modifications known in the art to enhance such formation of the heterodimer, as described e.g. in WO 96/027011, Ridgway, J. B., et al., Protein Eng 9 (1996) 617-621; Merchant, A. M., et al., Nat Biotechnol 16 (1998) 677-681, WO 96/027011, WO 98/050431, US 2010/0015133, WO 2007/147901, WO 2009/089004, WO 2010/129304 and Muda, M., et al., Protein Engineering, Design & Selection 24 (2011) 447-454.

In one embodiment of the invention the bispecific, bivalent antibody comprises a Fc part derived from human origin and preferably all other parts of the human constant regions wherein the CH3 (and/or CH2) domains of the bispecific, bivalent antibody are altered by one or more modifications to enhance the formation of the heterodimers.

Thus one embodiment of the invention is a bispecific, bivalent antibody comprising a first antigen-binding site that specifically binds to human TWEAK and a second antigen-binding site that specifically binds to human IL17, wherein the bispecific, antibody is characterized in comprising the amino acid sequences of SEQ ID NO: 76, SEQ ID NO: 77, SEQ ID NO: 78, and SEQ ID NO: 79.

One embodiment of the invention is a bispecific, bivalent antibody comprising a first antigen-binding site that specifically binds to human TWEAK and a second antigen-binding site that specifically binds to human IL17, wherein the bispecific, antibody is characterized in comprising the amino acid sequences of SEQ ID NO: 80, SEQ ID NO: 81, and SEQ ID NO: 82.

One embodiment of the invention is a bispecific, bivalent antibody comprising a first antigen-binding site that specifically binds to human TWEAK and a second antigen-binding site that specifically binds to human IL17, wherein the bispecific, antibody is characterized in comprising the amino acid sequences of SEQ ID NO: 85, SEQ ID NO: 86, and SEQ ID NO: 87.

One embodiment of the invention is a bispecific, bivalent antibody comprising a first antigen-binding site that specifically binds to human TWEAK and a second antigen-binding site that specifically binds to human IL17, wherein the bispecific, antibody is characterized in comprising the amino acid sequences of SEQ ID NO: 88, SEQ ID NO: 89, and SEQ ID NO: 90.

One embodiment of the invention is a bispecific, bivalent antibody comprising a first antigen-binding site that specifically binds to human TWEAK and a second antigen-binding site that specifically binds to human IL17, wherein the bispecific, antibody is characterized in comprising the amino acid sequences of SEQ ID NO: 91, SEQ ID NO: 92, and SEQ ID NO: 93.

One embodiment of the invention is a bispecific, bivalent antibody comprising a first antigen-binding site that specifically binds to human TWEAK and a second antigen-binding site that specifically binds to human IL17, wherein the bispecific, antibody is characterized in comprising the amino acid sequences of SEQ ID NO: 94, SEQ ID NO: 95, SEQ ID NO: 96, and SEQ ID NO: 97.

In one embodiment of the invention the CH3 domains of the bispecific, bivalent antibody are altered by the "knob-into-holes" technology which is described in detail with several examples in e.g. WO 96/027011, WO98/050431, Ridgway, J. B., et al., Protein Eng 9 (1996) 617-621; and Merchant, A. M., et al., Nat Biotechnol 16 (1998) 677-681. In this method the interaction surfaces of the two CH3 domains are altered to increase the heterodimerisation of both heavy chains containing these two CH3 domains. Each of the two CH3 domains (of the two heavy chains) can be the "knob", while the other is the "hole". The introduction of a disulfide bridge stabilizes the heterodimers (Merchant, A. M, et al., Nature Biotech 16 (1998) 677-681; Atwell, S., et al. J. Mol. Biol. 270 (1997) 26-35) and increases the yield.

In a preferred aspect of the invention all bispecific antibodies according to the invention are characterized in that
the CH3 domain of one heavy chain and the CH3 domain of the other heavy chain each meet at an interface which comprises an original interface between the antibody CH3 domains;

wherein said interface is altered to promote the formation of the bispecific antibody, wherein the alteration is characterized in that:

a) the CH3 domain of one heavy chain is altered,
so that within the original interface the CH3 domain of one heavy chain that meets the original interface of the CH3 domain of the other heavy chain within the bispecific antibody,
an amino acid residue is replaced with an amino acid residue having a larger side chain volume, thereby generating a protuberance within the interface of the CH3 domain of one heavy chain which is positionable in a cavity within the interface of the CH3 domain of the other heavy chain
and
b) the CH3 domain of the other heavy chain is altered,
so that within the original interface of the second CH3 domain that meets the original interface of the first CH3 domain within the bispecific antibody
an amino acid residue is replaced with an amino acid residue having a smaller side chain volume, thereby generating a cavity within the interface of the second CH3 domain within which a protuberance within the interface of the first CH3 domain is positionable.

Thus the antibody according to invention is preferably characterized in that
the CH3 domain of the heavy chain of the full length antibody of a) and the CH3 domain of the heavy chain of the full length antibody of b) each meet at an interface which comprises an alteration in the original interface between the antibody CH3 domains;
wherein i) in the CH3 domain of one heavy chain
an amino acid residue is replaced with an amino acid residue having a larger side chain volume, thereby generating a protuberance within the interface of the CH3 domain of one heavy chain which is positionable in a cavity within the interface of the CH3 domain of the other heavy chain
and wherein ii) in the CH3 domain of the other heavy chain
an amino acid residue is replaced with an amino acid residue having a smaller side chain volume, thereby generating a cavity within the interface of the second CH3 domain within which a protuberance within the interface of the first CH3 domain is positionable.

Preferably said amino acid residue having a larger side chain volume is selected from the group consisting of arginine (R), phenylalanine (F), tyrosine (Y), tryptophan (W).

Preferably said amino acid residue having a smaller side chain volume is selected from the group consisting of alanine (A), serine (S), threonine (T), valine (V).

In one aspect of the invention both CH3 domains are further altered by the introduction of cysteine (C) as amino acid in the corresponding positions of each CH3 domain such that a disulfide bridge between both CH3 domains can be formed.

In one embodiment, the bispecific, bivalent antibody comprises a T366W mutation in the CH3 domain of the "knobs chain" and T366S, L368A, Y407V mutations in the CH3 domain of the "hole chain". An additional interchain disulfide bridge between the CH3 domains can also be used (Merchant, A. M, et al., Nature Biotech 16 (1998) 677-681) e.g. by introducing a Y349C mutation into the CH3 domain of the "knobs chain" and a E356C mutation or a S354C mutation into the CH3 domain of the "hole chain" (numbering according to the EU index of Kabat et al., Sequences of Proteins of Immunological Interest, 5th ed., Public Health Service, National Institutes of Health, Bethesda, Md. (1991)).

In another embodiment, the bispecific, bivalent antibody according to the invention comprises Y349C, T366W mutations in one of the two CH3 domains and E356C, T366S, L368A, Y407V mutations in the other of the two CH3 domains. In a another preferred embodiment the bispecific antibody comprises Y349C, T366W mutations in one of the two CH3 domains and S354C, T366S, L368A, Y407V mutations in the other of the two CH3 domains (the additional Y349C mutation in one CH3 domain and the additional E356C or S354C mutation in the other CH3 domain forming a interchain disulfide bridge) (numbering always according to EU index of Kabat; (Kabat, E. A., et al., Sequences of Proteins of Immunological Interest, 5th ed., Public Health Service, National Institutes of Health, Bethesda, Md. (1991))). But also other knobs-in-holes technologies as described by EP 1 870 459 A1, can be used alternatively or additionally. Thus another example for the bispecific antibody are R409D; K370E mutations in the CH3 domain of the "knobs chain" and D399K; E357K mutations in the CH3 domain of the "hole chain" (numbering always according to EU index of Kabat; (Kabat, E. A., et al., Sequences of Proteins of Immunological Interest, 5th ed., Public Health Service, National Institutes of Health, Bethesda, Md. (1991)).

In another embodiment the bispecific, bivalent antibody comprises a T366W mutation in the CH3 domain of the "knobs chain" and T366S, L368A, Y407V mutations in the CH3 domain of the "hole chain" and additionally R409D; K370E mutations in the CH3 domain of the "knobs chain" and D399K; E357K mutations in the CH3 domain of the "hole chain".

In another embodiment the bispecific, bivalent antibody comprises Y349C, T366W mutations in one of the two CH3 domains and S354C, T366S, L368A, Y407V mutations in the other of the two CH3 domains or said bispecific antibody comprises Y349C, T366W mutations in one of the two CH3 domains and S354C, T366S, L368A, Y407V mutations in the other of the two CH3 domains and additionally R409D; K370E mutations in the CH3 domain of the "knobs chain" and D399K; E357K mutations in the CH3 domain of the "hole chain". Such knob and hole mutations in the CH3 domain are typically used in human heavy chain constant regions of SEQ ID NO: 61, SEQ ID NO: 62, SEQ ID NO: 63 or SEQ ID NO: 64 (human IgG1 subclass allotypes (Caucasian and Afroamerican or mutants L234A/L235A, and L234A/L235A/P329G), SEQ ID NO: 65, SEQ ID NO: 66, or SEQ ID NO: 67 (human IgG4 subclass or mutants L234A/L235A, and L234A/L235A/P329G) (numbering according to the EU index of Kabat et al., Sequences of Proteins of Immunological Interest, 5th ed., Public Health Service, National Institutes of Health, Bethesda, Md. (1991)).

Thus in one embodiment, the bispecific antibody according to the invention comprises human heavy chain constant regions of SEQ ID NO: 61, SEQ ID NO: 62, SEQ ID NO: 63 or SEQ ID NO: 64 (human IgG1 subclass allotypes (Caucasian and Afroamerican or mutants L234A/L235A, and L234A/L235A/P329G), SEQ ID NO: 65, SEQ ID NO: 66, or SEQ ID NO: 67 (human IgG4 subclass or mutants L234A/L235A, and L234A/L235A/P329G) further including such "knob" and "hole" mutations in the CH3 domain (e.g. Y349C, T366W mutations in one of the two CH3 domains and S354C, T366S, L368A, Y407V mutations in the other of the two CH3 domains) (numbering according to the EU index of Kabat et al., Sequences of Proteins of Immunological Interest, 5th ed., Public Health Service, National Institutes of Health, Bethesda, Md. (1991)).

Such bivalent bispecific antibody specifically binding to human TWEAK and human IL17 according to the invention, have especially valuable properties such as low viscosity and high stability (so that they can be produced without high aggregation and in good yields). Such bivalent bispecific antibodies with their low viscosity and high stability are especially useful in highly concentrated formulations/compositions which can be used e.g. in a subcutaneous administration.

Thus one embodiment of the invention is a bispecific, bivalent antibody comprising a first antigen-binding site that specifically binds to human TWEAK and a second antigen-binding site that specifically binds to human IL17 characterized in that a) the viscosity at 100 mg/ml is 4.0 mPa·s or lower (and/or the viscosity at 70 mg/ml is 3.0 mPa·s or lower and/or the viscosity at 150 mg/ml is 8.5 mPa·s or lower) (as determined in Example 18)

b) aggregation temperature is 55° C. or higher (as determined in Example 18)

The aggregation temperature refers to the DLS aggregation onset temperature (see Example 18).

In one embodiment said bispecific antibody is trivalent using e.g. formats based on a full length antibody specifically binding to one of the two antigens TWEAK or IL17, to which only at one C-terminus of one heavy chain a scFab fragment is fused which specifically binds to the other of the two antigens TWEAK or IL17, including knobs—into holes technology, as described e.g. in WO 2010/112193 or e.g. formats based on a full length antibody specifically binding to one of the two antigens TWEAK or IL17, to which at one C-terminus of one heavy chain a VH or VH-CH1 fragment and at the other C-terminus of the second heavy chain a VL or VL-CL fragment is fused which specifically binds to the other of the two antigens TWEAK or IL17, including knobs—into holes technology, as described e.g. in WO 2010/115589 or WO 2011/028952.

In one embodiment the bispecific antibody specifically binding to human TWEAK and human IL17 according to the invention is a tetravalent antibody ("four binding arms") with two different specifities as described e.g. in WO 2007/024715, or WO 2007/109254, WO 2010/112193, WO 2010/145792 or WO 2010/145793 (see also Example 14; <Tweak-IL-17> #5).

One embodiment of the invention is a bispecific, tetravalent antibody comprising a first antigen-binding site that specifically binds to human TWEAK and a second antigen-binding site that specifically binds to human IL17, wherein the bispecific, antibody is characterized in comprising the amino acid sequences of SEQ ID NO: 83, and SEQ ID NO: 84.

Figure 1B:
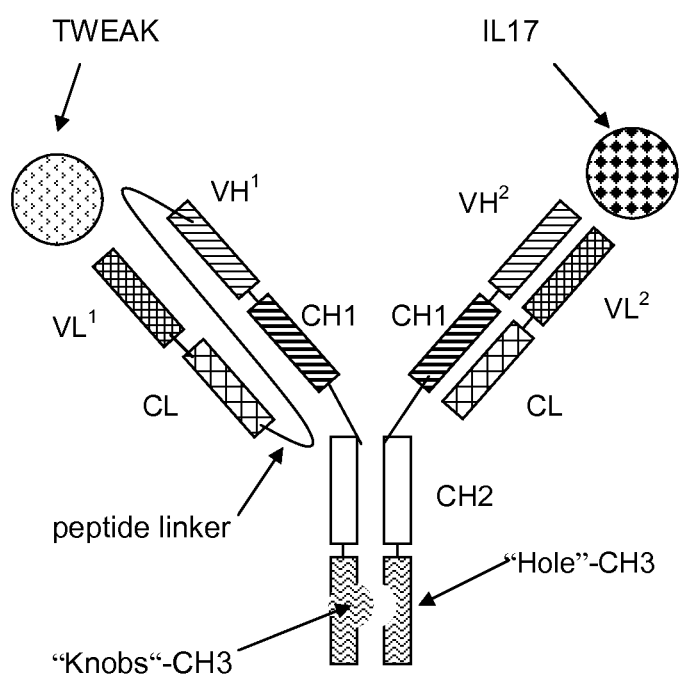
Figure 2:
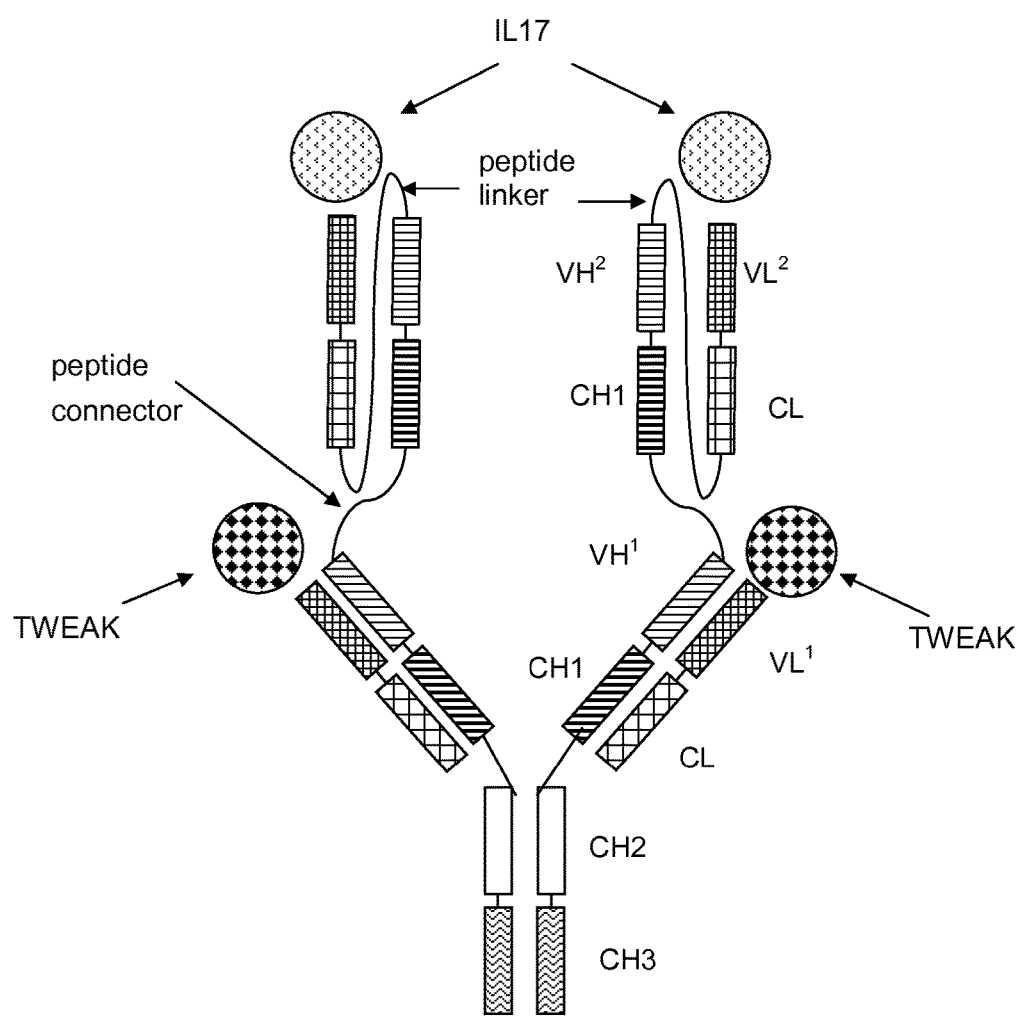
FIG. 2 One exemplary bispecific, tetravalent antibody format for the bispecific <TWEAK/IL17> antibodies according to the invention is shown.

The bispecific, bivalent antibody formats of WO 2011/117330 ("bispecific one-armed scFab antibodies") and the bispecific, tetravalent antibody formats of WO 2010/112193 comprise single chain Fab fragments (scFab) in which the Fab heavy and light chain fragments are linked via a peptide linker (see FIGS. 1b and 2, as well as WO 2011/117330 and WO 2010/112193). The peptide linker is typically a peptide with amino acid sequences, which is preferably of synthetic origin and has a length of at least 30 amino acids, preferably a length of 30 to 50 amino acids (in one embodiment with a length of 32 to 40 amino acids). In one embodiment said linker is (GxS)n with G=glycine, S=serine, (x=3, n=8, 9 or 10 and m=0, 1, 2 or 3) or (x=4 and n=6, 7 or 8 and m=0, 1, 2 or 3). In one embodiment said peptide linker is (G4S)6G2.

The bispecific, tetravalent antibody formats of WO 2007/024715, or WO 2007/109254, WO 2010/112193, WO 2010/145792 or WO 2010/145793 comprise peptide connectors to link the antigen binding site to a full length antibody. Typically such peptide connector is a peptide with amino acid sequences, which is preferably of synthetic origin and has a length of at least 5 amino acids, preferably with a length of 5 to 100, (in one embodiment with a length of 10 to 50 amino acids; in one embodiment with a length of 10 to 50 amino acids). In one embodiment said peptide connector is (GxS)n or (GxS)nGm with G=glycine, S=serine, and (x=3, n=3, 4, 5 or 6, and m=0, 1, 2 or 3) or (x=4, n=2, 3, 4 or 5 and m=0, 1, 2 or 3). In one embodiment said peptide connector is (G3S)3 or (G4S)2.

A further embodiment of the invention is a method for the production of a bispecific antibody according to the invention, characterized in that the sequence of a nucleic acid encoding the heavy chain of an antibody according to the invention and the nucleic acid encoding the light chain of said antibody are inserted into one or two expression vector(s), said vector(s) is/are inserted in a eukaryotic host cell, the encoded antibody is expressed and recovered from the host cell or the supernatant.

The antibodies according to the invention are preferably produced by recombinant means. Such methods are widely known in the state of the art and comprise protein expression in prokaryotic and eukaryotic cells with subsequent isolation of the antibody polypeptide and usually purification to a pharmaceutically acceptable purity. For the protein expression nucleic acids encoding light and heavy chains or fragments thereof are inserted into expression vectors by standard methods. Expression is performed in appropriate prokaryotic or eukaryotic host cells, such as CHO cells, NS0 cells, SP2/0 cells, HEK293 cells, COS cells, yeast, or *E. coli* cells, and the antibody is recovered from the cells (from the supernatant or after cells lysis).

Recombinant production of antibodies is well-known in the state of the art and described, for example, in the review articles of Makrides, S. C., Protein Expr. Purif. 17 (1999) 183-202; Geisse, S., et al., Protein Expr. Purif. 8 (1996) 271-282; Kaufman, R. J., Mol. Biotechnol. 16 (2000) 151-160; Werner, R. G., Arzneimittelforschung (Drug Res.) 48 (1998) 870-880.

The antibodies may be present in whole cells, in a cell lysate, or in a partially purified, or substantially pure form. Purification is performed in order to eliminate other cellular components or other contaminants, e.g., other cellular nucleic acids or proteins, by standard techniques, including column chromatography and others well known in the art. See Ausubel, F. et al. (eds.), Current Protocols in Molecular Biology, Greene Publishing and Wiley Interscience, New York (1987).

Expression in NS0 cells is described by, e.g., Barnes, L. M., et al., Cytotechnology 32 (2000) 109-123; Barnes, L. M., et al., Biotech. Bioeng. 73 (2001) 261-270. Transient expression is described by, e.g., Durocher, Y., et al., Nucl. Acids. Res. 30 (2002) E9. Cloning of variable domains is described by Orlandi, R., et al., Proc. Natl. Acad. Sci. USA 86 (1989) 3833-3837; Carter, P., et al., Proc. Natl. Acad. Sci. USA 89 (1992) 4285-4289; Norderhaug, L., et al., J. Immunol. Methods 204 (1997) 77-87. A preferred transient expression system (HEK 293) is described by Schlaeger, E.-J. and Christensen, K., in Cytotechnology 30 (1999) 71-83, and by Schlaeger, E.-J., in J. Immunol. Methods 194 (1996) 191-199.

Monoclonal antibodies are suitably separated from the culture medium by conventional immunoglobulin purification procedures such as, for example, protein A-Sepharose, hydroxylapatite chromatography, dialysis, or affinity chromatography. DNA and RNA encoding the monoclonal antibodies is readily isolated and sequenced using conventional procedures. The hybridoma cells can serve as a source of such DNA and RNA. Once isolated, the DNA may be inserted into expression vectors, which are then transfected into host cells, such as HEK 293 cells, CHO cells, or myeloma cells that do not otherwise produce immunoglobulin protein, to obtain the synthesis of recombinant monoclonal antibodies in the host cells.

Nucleic acid molecules encoding amino acid sequence variants of anti-TWEAK/anti-IL17 bispecific antibody are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of anti-TWEAK/anti-IL17 bispecific antibody.

The heavy and light chain variable domains according to the invention are combined with sequences of promoter, translation initiation, constant region, 3' untranslated region, polyadenylation, and transcription termination to form expression vector constructs. The heavy and light chain expression constructs can be combined into a single vector, co-transfected, serially transfected, or separately transfected into host cells which are then fused to form a single host cell expressing both chains.

The bispecific TWEAK/IL17 antibody, especially the bispecific bivalent antibodies have valuable properties such good developability and producibility, (e.g. no hotspots are contained which require specific production conditions), good titers and yields and are producible in high amounts and with relatively low impurities (>60% Monomer after Protein A (SE-HPLC) with an estimated purity after 2nd column (ESI-MS)>80%) (see Example 14 and 15).

Pharmaceutical Compositions

Pharmaceutical compositions of a bispecific TWEAK/IL17 antibody as described herein are prepared by mixing such antibody having the desired degree of purity with one or more optional pharmaceutically acceptable carriers (Remington's Pharmaceutical Sciences, 16th edition, Osol, A. (ed.) (1980)), in the form of lyophilized formulations or aqueous solutions. Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyl dimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as poly(vinylpyrrolidone); amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG). Exemplary pharmaceutically acceptable carriers herein further include interstitial drug dispersion agents such as soluble neutral-active hyaluronidase glycoproteins (sHASEGP), for example, human soluble PH-20 hyaluronidase glycoproteins, such as rhuPH2O (HYLENEX®, Baxter International, Inc.). Certain exemplary sHASEGPs and methods of use, including rhuPH2O, are described in US Patent Publication Nos. 2005/0260186 and 2006/0104968. In one aspect, a sHASEGP is combined with one or more additional glycosaminoglycanases such as chondroitinases.

Exemplary lyophilized antibody formulations are described in U.S. Pat. No. 6,267,958. Aqueous antibody formulations include those described in U.S. Pat. No. 6,171,586 and WO 2006/044908, the latter formulations including a histidine-acetate buffer.

The formulation herein may also contain more than one active ingredients as necessary for the particular indication being treated, preferably those with complementary activities that do not adversely affect each other.

The bispecific antibodies specifically binding to human TWEAK and human IL17 according to the invention (especially the bispecific, bivalent), have especially valuable properties such as low viscosity and high stability (so that they can be produced without high aggregation and in good yields) (see Example 18). Such bivalent bispecific antibodies with their low viscosity and high stability are especially useful in highly concentrated formulations/compositions which can be used e.g. in a subcutaneous administration.

The bispecific antibodies according to the invention may be administered as the sole active ingredient or in conjunction with, e.g. as an adjuvant to or in combination to, other drugs e.g. immunosuppressive or immunomodulating agents or other anti-inflammatory agents, e.g. for the treatment or prevention of diseases mentioned above. For example, the bispecific antibodies as described herein may be used in combination with DMARD, e.g. Gold salts, sulphasalazine, antimalarias, methotrexate, D-penicillamine, azathioprine, mycophenolic acid, cyclosporine A, tacrolimus, sirolimus, minocycline, leflunomide, glococorticoids; a calcineurin inhibitor, e.g. cyclosporin A or FK 506; a modulator of lymphocyte recirculation, e.g. FTY720 and FTY720 analogs; a mTOR inhibitor, e.g. rapamycin, 40-O-(2-hydroxyethyl)-rapamycin, CCI779, ABT578, AP23573 or TAFA-93; an ascomycin having immuno-suppressive properties, e.g. ABT-281, ASM981, etc.; corticosteroids; cyclophosphamide; azathioprene; methotrexate; leflunomide; mizoribine; mycophenolic acid; myco-pheno-late mofetil; 15-deoxyspergualine or an immunosuppressive homologue, analogue or derivative thereof; immunosuppressive monoclonal antibodies, e.g., monoclonal antibodies to leukocyte receptors, e.g., MHC, CD2, CD3, CD4, CD7, CD8, CD25, CD28, CD40. CD45, CD58, CD80, CD86 or their ligands; other immunomodulatory compounds, e.g. a recombinant binding molecule having at least a portion of the extracellular domain of CTLA4 or a mutant thereof, e.g. an at least extracellular portion of CTLA4 or a mutant thereof joined to a non-CTLA4 protein sequence, e.g. CTLA4Ig (for ex. designated ATCC 68629) or a mutant thereof, e.g. LEA29Y; adhesion molecule inhibitors, e.g. LFA-1 antagonists, ICAM-1 or -3 antagonists, VCAM-4 antagonists or VLA-4 antagonists; or a chemotherapeutic agent, e.g. paclitaxel, gemcitabine, cisplatinum, doxorubicin or 5-fluorouracil; anti TNF agents, e.g. monoclonal antibodies to TNF, e.g. infliximab, adalimumab, CDP870, or receptor constructs to TNF-RI or TNF-RII, e.g. Etanercept, PEG-TNF-RI; blockers of proinflammatory cytokines, IL-1 blockers, e.g. Anakinra or IL-1 trap, AAL160, ACZ 885, IL-6 blockers; chemokines blockers, e.g. inhibitors or activators of proteases, e.g. metalloproteases, anti-IL-15 antibodies, anti-IL-6 antibodies, anti-IL-23 antibodies, anti-CD20 antibodies, NSAIDs, such as aspirin or an anti-infectious agent (the list not limited to the agent mentioned).

A bispecific antibody according to the present invention may be provided in combination or addition with one or more of the following agents:

an antagonist of cytokine function, (e.g. an agent which act on cytokine signaling pathways such as a modulator of the SOCS system), such as an alpha-, beta-, and/or gamma-interferon; modulators of insulin-like growth factor type I (IGF-I), its receptors and associated binding proteins; interleukins (IL) e.g. one or more of IL-1 to 33, and/or an interleukin antagonist or inhibitor such as anakinra; inhibitors of receptors of interleukin family members or inhibitors of specific subunits of such receptors; a tumor necrosis factor alpha (TNF-.alpha.) inhibitor such as an anti-TNF monoclonal antibody (for example infliximab; adalimumab, and/or CDP-870), and/or a TNF receptor antagonist e.g. an immunoglobulin molecule (such as etanercept) and/or a low-molecular-weight agent such as pentoxyfylline;

a modulator of B cells, e.g. a monoclonal antibody targeting B-lymphocytes (such as CD20 (rituximab) or MRA-aIL16R) or T-lymphocytes (e.g. CTLA4-Ig, HuMax 11-15 or Abatacept);

a modulator that inhibits osteoclast activity, for example an antibody to RANKL;

a modulator of chemokine or chemokine receptor function such as an antagonist of CCR1, CCR2, CCR2A, CCR2B, CCR3, CCR4, CCR5, CCR6, CCR7, CCR8, CCR9, CCR1O and CCRI1 (for the C-C family); CXCR1, CXCR2, CXCR3, CXCR4 and CXCR5 and CXCR6 (for the C-X-C family) and CX3 CR1 for the C-X3-C family;

an inhibitor of matrix metalloproteases (MMPs), i.e., one or more of the stromelysins, the collagenases, and the gelatinases, as well as aggrecanase; especially collagenase-1 (MMP1), collagenase-2 (MMP8), collagenase-3 (MMP13), stromelysin-1 (MMP3), stromelysin-2 (MMP10), and/or stromelysin-3 (MMP11) and/or MMP9 and/or MMP12, e.g. an agent such as doxycycline; a leukotriene biosynthesis inhibitor, 5-lipoxygenase (5-LO) inhibitor or 5-lipoxygenase activating protein (FLAP) antagonist such as; zileuton; ABT-761; fenleuton; tepoxalin; Abbott-79175; Abbott-85761; N-(5-substituted)-thiophene-2-alkylsulfonamides; 2, 6-di-tert-butylphenolhydrazones; methoxytetrahydropyrans such as Zeneca ZD-2138; the compound SB-210661; a pyridinyl-substituted 2-cyanonaphthalene compound such as L-739,010; a 2-cyanoquinoline compound such as L-746,530; indole and/or a quinoline compound such as MK-591, MK-886, and/or BAY x 1005; a receptor antagonist for leukotrienes (LT) B4, LTC4, LTD4, and LTE4, selected from the group consisting of the phenothiazin-3-1s such as L-651,392; amidino compounds such as CGS-25019c; benzoxalamines such as ontazolast; benzenecarboximidamides such as BIIL 284/260; and compounds such as zafirlukast, ablukast, montelukast, pranlukast, verlukast (MK-679), RG-12525, Ro-245913, iralukast (CGP 45715A), and BAY x 7195; a phosphodiesterase (PDE) inhibitor such as a methylxanthanine, e.g. theophylline and/or aminophylline; and/or a selective PDE isoenzyme inhibitor e.g. a PDE4 inhibitor and/or inhibitor of the isoform PDE4D, and/or an inhibitor of PDE5;

a histamine type 1 receptor antagonist such as cetirizine, loratadine, desloratadine, fexofenadine, acrivastine, terfenadine, astemizole, azelastine, levocabastine, chlorpheniramine, promethazine, cyclizine, and/or mizolastine (generally applied orally, topically or parenterally);

a proton pump inhibitor (such as omeprazole) or gastroprotective histamine type 2 receptor antagonist; —an antagonist of the histamine type 4 receptor; an alpha-1/alpha-2 adrenoceptor agonist vasoconstrictor sympathomimetic agent, such as propylhexedrine, phenylephrine, phenylpropanolamine, ephedrine, pseudoephedrine, naphazoline hydrochloride, oxymetazoline hydrochloride, tetrahydrozoline hydrochloride, xylometazoline hydrochloride, tramazoline hydrochloride, and ethylnorepinephrine hydrochloride; an anticholinergic agent, e.g. a muscarinic receptor (M1, M2, and M3) antagonist such as atropine, hyoscine, glycopyrrrolate, ipratropium bromide, tiotropium bromide, oxitropium bromide, pirenzepine, and telenzepine;

a beta-adrenoceptor agonist (including beta receptor subtypes 1-4) such as isoprenaline, salbutamol, formoterol, salmeterol, terbutaline, orciprenaline, bitolterol mesylate, and/or pirbuterol, e.g. a chiral enantiomer thereof;

a chromone, e.g. sodium chromoglycate and/or nedocromil sodium;

a glucocorticoid, such as flunisolide, triamcinolone acetonide, beclomethasone dipropionate, budesonide, fluticasone propionate, ciclesonide, and/or mometasone furoate; an agent that modulate nuclear hormone receptors such as a PPAR;

an immunoglobulin (Ig) or Ig preparation or an antagonist or antibody modulating Ig function such as anti-IgE (e.g. omalizumab);

other systemic or topically-applied anti-inflammatory agent, e.g. thalidomide or a derivative thereof, a retinoid, dithranol, and/or calcipotriol;

combinations of aminosalicylates and sulfapyridine such as sulfasalazine, mesalazine, balsalazide, and olsalazine; and immunomodulatory agents such as the thiopurines, and corticosteroids such as budesonide;

an antibacterial agent e.g. a penicillin derivative, a tetracycline, a macrolide, a beta-lactam, a fluoroquinolone, metronidazole, and/or an inhaled aminoglycoside; and/or an antiviral agent e.g. acyclovir, famciclovir, valaciclovir, ganciclovir, cidofovir; amantadine, rimantadine; ribavirin; zanamavir and/or oseltamivir; a protease inhibitor such as indinavir, nelfinavir, ritonavir, and/or saquinavir; a nucleoside reverse transcriptase inhibitor such as didanosine, lamivudine, stavudine, zalcitabine, zidovudine; a non-nucleoside reverse transcriptase inhibitor such as nevirapine, efavirenz; a cardiovascular agent such as a calcium channel blocker, beta-adrenoceptor blocker, angiotensin-converting enzyme (ACE) inhibitor, angiotensin-2 receptor antagonist; lipid lowering agent such as a statin, and/or fibrate; a modulator of blood cell morphology such as pentoxyfylline; a thrombolytic, and/or an anticoagulant e.g. a platelet aggregation inhibitor;

a CNS agent such as an antidepressant (such as sertraline), anti-Parkinsonian drug (such as deprenyl, L-dopa, ropinirole, pramipexole, MAOB inhibitor such as selegine and rasagiline, comP inhibitor such as tasmar, A-2 inhibitor, dopamine reuptake inhibitor, NMDA antagonist, nicotine agonist, dopamine agonist and/or inhibitor of neuronal nitric oxide synthase), and an anti-Alzheimer's drug such as donepezil, rivastigmine, tacrine, COX-2 inhibitor, propentofylline or metrifonate; an agent for the treatment of acute and chronic pain, e.g. a centrally or peripherally-acting analgesic such as an opioid analogue or derivative, carbamazepine, phenytoin, sodium valproate, amitryptiline or other antidepressant agent, paracetamol, or nonsteroidal anti-inflammatory agent; a parenterally or topically-applied (including inhaled) local anaesthetic agent such as lignocaine or an analogue thereof; an anti-osteoporosis agent e.g. a hormonal agent such as raloxifene, or a biphosphonate such as alendronate;

(i) a tryptase inhibitor; (ii) a platelet activating factor (PAF) antagonist; (iii) an interleukin converting enzyme (ICE) inhibitor; (iv) an IMPDH inhibitor; (v) an adhesion molecule inhibitors including VLA-4 antagonist; (vi) a cathepsin; (vii) a kinase inhibitor e.g. an inhibitor of tyrosine kinases (such as Btk, Itk, Jak3 MAP examples of inhibitors might include Gefitinib, Imatinib mesylate), a serine/threonine kinase (e.g. an inhibitor of MAP kinase such as p38, JNK, protein kinases A, B and C and IKK), or a kinase involved in cell cycle regulation (e.g. a cylin dependent kinase); (viii) a glucose-6 phosphate dehydrogenase inhibitor; (ix) a kinin-B. sub1.- and/or B.sub2.-receptor antagonist; (x) an anti-gout agent, e.g., colchicine; (xi) a xanthine oxidase inhibitor, e.g., allopurinol; (xii) a uricosuric agent, e.g., probenecid, sulfinpyrazone, and/or benzbromarone; (xiii) a growth hormone secretagogue; (xiv) transforming growth factor (TGF.beta.); (xv) platelet-derived growth factor (PDGF); (xvi) fibroblast growth factor, e.g., basic fibroblast growth factor (bFGF); (xvii) granulocyte macrophage colony stimulating factor (GM-CSF); (xviii) capsaicin cream; (xix) a tachykinin NK. sub1. and/or NK.sub3. receptor antagonist such NKP-608C, SB-233412 (talnetant), and/or D-4418; (xx) an elastase inhibitor e.g. UT-77 and/or ZD-0892; (xxi) a TNF-alpha converting enzyme inhibitor (TACE); (xxii) induced nitric oxide synthase (iNOS) inhibitor or (xxiii) a chemoattractant receptor-homologous molecule expressed on TH2 cells, (such as a CRTH2 antagonist) (xxiv) an inhibitor of a P38 (xxv) agent modulating the function of Toll-like receptors (TLR) and (xxvi) an agent modulating the activity of purinergic receptors such as P2X7; (xxvii) an inhibitor of transcription factor activation such as NFkB, API, and/or STATS.

An inhibitor may be specific or may be a mixed inhibitor, e.g. an inhibitor targeting more than one of the molecules (e.g. receptors) or molecular classes mentioned above.

The bispecific antibody could also be used in association with a chemotherapeutic agent or another tyrosine kinase inhibitor in coadministration or in the form of an immunoconjugate. Fragments of said antibody could also be used in bispecific antibodies obtained by recombinant mechanisms or biochemical coupling, and then associating the specificity of the above described antibody with the specificity of other antibodies able to recognize other molecules involved in the activity for which IL-17 is associated. For treatment of an inflammatory disease, a bispecific antibody of the invention may be combined with one or more agents such as: —Nonsteroidal anti-inflammatory agents (hereinafter NSAIDs) including non-selective cyclo-oxygenase (COX)-1/COX-2 inhibitors whether applied topically or systemically (such as piroxicam, diclofenac, propionic acids such as naproxen, flurbiprofen, fenoprofen, ketoprofen and ibuprofen, fenamates such as mefenamic acid, indomethacin, sulindac, azapropazone, pyrazolones such as phenylbutazone, salicylates such as aspirin); selective COX-2 inhibitors (such as meloxicam, celecoxib, rofecoxib, valdecoxib, lumarocoxib, parecoxib and etoricoxib); cyclo-oxygenase inhibiting nitric oxide donors (CINODs); glucocorticosteroids (whether administered by topical, oral, intramuscular, intravenous, or intra-articular routes); methotrexate, leflunomide; hydroxychloroquine, d-penicillamine, auranofin or other parenteral or oral gold preparations; analgesics; diacerein; intra-articular therapies such as hyaluronic acid derivatives; and nutritional supplements such as glucosamine.

A bispecific antibody of the invention can also be used in combination with an existing therapeutic agent for the treatment of cancer. Suitable agents to be used in combination include: (i) antiproliferative/antineoplastic drugs and combinations thereof, as used in medical oncology, such as alkylating agents (for example cis-platin, carboplatin, cyclophosphamide, nitrogen mustard, melphalan, chlorambucil, busulphan and nitrosoureas); antimetabolites (for example antifolates such as fluoropyrimidines like 5-fluorouracil and tegafur, raltitrexed, methotrexate, cytosine arabinoside, hydroxyurea, gemcitabine and paclitaxel; antitumour antibiotics (for example anthracyclines like adriamycin, bleomycin, doxorubicin, daunomycin, epirubicin, idarubicin, mitomycin-C, dactinomycin and mithramycin); antimitotic agents (for example vinca alkaloids like vincristine, vinblastine, vindesine and vinorelbine and taxoids like taxol and taxotere); and topoisomerase inhibitors (for example epipodophyllotoxins like etoposide and teniposide, amsacrine, topotecan and camptothecins);

(ii) cytostatic agents such as antioestrogens (for example tamoxifen, toremifene, raloxifene, droloxifene and iodoxyfene), oestrogen receptor down regulators (for example fulvestrant), antiandrogens (for example bicalutamide, flutamide, nilutamide and cyproterone acetate), LHRH antagonists or LHRH agonists (for example goserelin, leuprorelin and buserelin), progestogens (for example megestrol acetate), aromatase inhibitors (for example as anastrozole, letrozole, vorazole and exemestane) and inhibitors of 5.alpha.-reductase such as finasteride;

(iii) Agents which inhibit cancer cell invasion (for example metalloproteinase inhibitors like marimastat and inhibitors of urokinase plasminogen activator receptor function); (iv) inhibitors of growth factor function, for example such inhibitors include growth factor antibodies, growth factor receptor antibodies (for example the anti-erbb2 antibody trastuzumab and the anti-erbb1 antibody cetuximab [C225]), farnesyl transferase inhibitors, tyrosine kinase inhibitors and serine/threonine kinase inhibitors, for example inhibitors of the epidermal growth factor family (for example EGFR family tyrosine kinase inhibitors such as N-(3-chloro-4-fluorophenyl)-7-methoxy-6-(3-morpholinopropoxy) quinazolin-4-amine (gefitinib, AZD1839), N-(3-ethynylphenyl)-6,7-bis(2-methoxyethoxy)quinazolin-4-amine (erlotinib, OSI-774) and 6-acrylamido-N-(3-chloro-4-fluorophenyl)-7-(3-morpholinopropoxy)quinazolin-4-amine (CI 1033)), for example inhibitors of the platelet-derived growth factor family and for example inhibitors of the hepatocyte growth factor family; (v) antiangiogenic agents such as those which inhibit the effects of vascular endothelial growth factor, (for example the anti-vascular endothelial cell growth factor antibody bevacizumab, compounds such as those disclosed in International Patent Applications WO 97/22596, WO 97/30035, WO 97/32856 and WO 98/13354, each of which is incorporated herein in its entirety) and compounds that work by other mechanisms (for example linomide, inhibitors of integrin .alpha.v.beta.3 function and angiostatin); (vi) vascular damaging agents such as combretastatin A4 and compounds disclosed in International Patent Applications WO 99/02166, WO 00/40529, WO 00/41669, WO 01/92224, WO 02/04434 and WO 02/08213, each of which is incorporated herein in its entirety; (vii) antisense therapies, for example those which are directed to the targets listed above, such as ISIS 2503, an anti-ras antisense; (viii) gene therapy approaches, including for example approaches to replace aberrant genes such as aberrant p53 or aberrant BRCA1 or BRCA2, GDEPT (gene directed enzyme pro-drug therapy) approaches such as those using cytosine deaminase, thymidine kinase or a bacterial nitroreductase enzyme and approaches to increase patient tolerance to chemotherapy or radiotherapy such as multi-drug resistance gene therapy; and (ix) immunotherapeutic approaches, including for example ex vivo and in vivo approaches to increase the immunogenicity of patient tumor cells, such as transfection with cytokines such as interleukin 2, interleukin 4 or granulocyte macrophage colony stimulating factor, approaches to decrease T cell anergy, approaches using transfected immune cells such as cytokine transfected dendritic cells, approaches using cytokine transfected tumor cell lines and approaches using anti-idiotypic antibodies.

Such active ingredients are suitably present in combination in amounts that are effective for the purpose intended.

Active ingredients may be entrapped in microcapsules prepared, for example, by coacervation techniques or by interfacial polymerization, for example, hydroxymethylcellulose or gelatin-microcapsules and poly-(methyl methacrylate) microcapsules, respectively, in colloidal drug delivery systems (for example liposomes, albumin microspheres, microemulsions, nano-particles and nanocapsules) or in macroemulsions. Such techniques are disclosed in Remington's Pharmaceutical Sciences, 16th edition, Osol, A. (ed.) (1980).

Sustained-release preparations may be prepared. Suitable examples of sustained-release preparations include semipermeable matrices of solid hydrophobic polymers containing the antibody, which matrices are in the form of shaped articles, e.g. films, or microcapsules.

The compositions to be used for in vivo administration are generally sterile. Sterility may be readily accomplished, e.g., by filtration through sterile filtration membranes.

The bispecific antibody according to the invention, especially the bispecific bivalent antibody, have valuable biological properties (determined in assays as described in Examples 3, 4, 10, 11, 16, 17 and 19):

A) the bispecific TWEAK/IL17 antibody inhibits
  a) TWEAK induced proliferation of human fibroblast-like synoviocytes-rheumatoid arthritis (HFLS-RA) with an IC50 value of 0.2 nM or lower (e.g. with an IC50 value between 0.2 nM and 0.0 nM); preferably with an IC50 value of 0.1 nM or lower (as determined in Example 17 as IC50/per valency); and
  b) IL17 induced IL6 cytokine stimulation of human fibroblast-like synoviocytes-rheumatoid arthritis (HFLS-RA) with an IC50 value of 3.0 nM or lower (e.g. with an IC50 value between 3.0 nM and 0.0 nM); preferably with an IC50 value of 2.0 nM or lower (as determined in Example 16); and
  c) IL17 induced IL8 cytokine stimulation of human fibroblast-like synoviocytes-rheumatoid arthritis (HFLS-RA) with an IC50 value of 2.0 nM or lower (e.g. with an IC50 value between 2.0 nM and 0.0 nM); preferably with an IC50 value of 1.5 nM or lower (as determined in Example 16);

B) the bispecific TWEAK/IL17 antibody is capable to simultaneously bind to human <TWEAK> and human <IL17>, wherein the signal intensity (in RU) (in a surface plasmon resonance assay (Example 19) of the binding of the bispecific TWEAK/IL17 antibody to a 1:1 mixture from human <TWEAK> and human <IL17> is at least the same or higher compared to the sum of a) the signal intensity (in RU) of the binding of the bispecific TWEAK/IL17 antibody to human <TWEAK> alone and b) the signal intensity (in RU) of the binding of the bispecific TWEAK/IL17 antibody to human <IL17> alone (as determined in Example 19);
C) the bispecific TWEAK/IL17 antibody shows no cross reactivity with IL17B, IL17C, IL17D, IL17F (which means that the binding to IL17B, IL17C, IL17D and IL17F is 0% compared to the binding to IL17A, which is set as 100%) (as determined in Example 10);
D) the bispecific TWEAK/IL17 antibody inhibits IL17 induced IL6 cytokine stimulation of CCD-25SK cells with an IC50 value of 2.0 nM or lower (e.g. with an IC50 value between 2.0 nM and 0.0 nM); (as determined in Example 11);
E) the bispecific TWEAK/IL17 antibody inhibits IL17 induced IL8 cytokine stimulation of CCD-25SK cells with an IC50 value of 5.0 nM or lower (e.g. with an IC50 value between 5.0 nM and 0.0 nM); preferably with an IC50 value of 2.0 nM or lower; (as determined in Example 11);
F) the bispecific TWEAK/IL17 antibody inhibits human TWEAK/human Fn14 interaction with an IC50 value of 4.0 [ng/ml] or lower (e.g. with an IC50 value between 4.0 [ng/ml] and 0.0 [ng/ml]); preferably with an IC50 value of 3.0 [ng/ml] or lower; (as determined in Example 4);
G) the bispecific TWEAK/IL17 antibody binds to human TWEAK with an KD value of binding affinity of 0.1 nM or lower, and binds to human IL-17 with an KD value of binding affinity of 0.3 nM or lower; (as determined in Example 19); and/or
H) the bispecific TWEAK/IL17 antibody shows a half-life of a complex between soluble human TWEAK (amino acids 99-249 of SEQ ID NO: 68) and antibody of 100 minutes or more at 25° C., measured by Biacore (as determined in Example 19).

The term "human fibroblast-like synoviocytes-rheumatoid arthritis (HFLS-RA)" refers to human adult fibroblast-like synoviocytes obtained from RA patients (human fibroblast-like synoviocytes-rheumatoid arthritis (HFLS-RA)), e.g. to HFLS-RA (Cat. #408RA-05a) obtainable from Cell Applications Inc. (San Diego, Calif., USA). Human Fibroblast-Like Synoviocytes-Rheumatoid Arthritis (HFLS-RA) are isolated from synovial tissues obtained from patients with Rheumatoid Arthritis (RA). They are cryopreserved at second passage and can be cultured and propagated at least 5 population doublings. HFLS are long known for their role in joint destruction by producing cytokines and metalloproteinases that contribute to cartilage degradation (Firestein, G. S., et al., J. Immunol. 149 (1992) 1054; Firestein, G. S., et al., Arthritis and Rheumatism 37(5) (1994) 644) Proinflammatory cytokines induce the proliferation, collagenase and aggrecanase production and GM-CSF secretion on HFLS (Alvaro, J. M., et al., J. Clin. Immunol. 13(3) (1993) 212; Yamanishi, Y., et al., J. Immunol. 168(3) (2002) 1405). Ongoing arthritis research also has shown that HFLS express apoptosis and P53 mutations (Firestein, G. S., et al., J. Clin. Invest. 96 (1995) 1631; Firestein, G. S., et al., Am. J. Pathol. 148(6) (1996) 2143). We provide two types of HFLS that are useful cellular models for studying the differences between HFLS-RA and HFLS-OA, such as the expression and regulation of proteases (Firestein, G. S., et al., Am. J. Pathol. 148(6) (1996) 2143) and integrin subunits (Rinaldi, N., et al., Ann. Rheum. Dis. 56(12) (1997) 729).

The "IL17 induced IL6 or IL8 cytokine stimulation" refers to the human IL6 or human IL8 cytokine stimulation by human IL17. The IC50 values for the TWEAK induced proliferation of human fibroblast-like synoviocytes-rheumatoid arthritis (HFLS-RA) and for the IL17 induced IL6 cytokine stimulation of human fibroblast-like synoviocytes-rheumatoid arthritis (HFLS-RA) are calculated as IC50 values per valency (per binding arm against the respective antigen (IL17 in Example 16 and TWEAK in Example 17). This mean that for a bispecific, bivalent antibody which has one binding arm for each antigen (=which is monovalent for each antigen), the IC50 values are identical to the determined IC50 values (of Examples 16 and 17). To compare such monovalent binding with that of a bispecific, tetravalent antibody which has two binding arms for each antigen (=which is bivalent for each antigen), the IC50 value is calculated with the assumption that the double molar concentration of binding arms was used to achieve the IC50, so the IC50 value is doubled (to get the corresponding 50% inhibitory concentration per binding arm).

The invention comprises a method for the treatment of a patient in need of therapy, characterized by administering to the patient a therapeutically effective amount of an antibody according to the invention.

The invention comprises the use of an antibody according to the invention for the preparation of a medicament for the treatment of cancer, especially colon, lung, or pancreatic cancer or for the treatment of autoimmune diseases, rheumatoid arthritis, psoratic arthritis, muscle diseases, e.g. muscular dystrophy, multiple sclerosis, chronic kidney diseases, bone diseases, e.g. bone degeneration in multiple myeloma, systemic lupus erythematosus, lupus nephritis, and vascular injury.

The invention comprises the use of an antibody according to the invention for the preparation of a medicament for the treatment of systemic lupus erythematosus, or lupus nephritis.

The invention comprises the use of an antibody according to the invention for the treatment of cancer or inflammatory diseases, preferably for the treatment of colon, lung, or pancreatic cancer or for the treatment of autoimmune diseases, rheumatoid arthritis, psoratic arthritis, muscle diseases, e.g. muscular dystrophy, multiple sclerosis, chronic kidney diseases, bone diseases, e.g. bone degeneration in multiple myeloma, systemic lupus erythematosus, lupus nephritis, and vascular injury.

The invention comprises the use of an antibody according to the invention for the treatment of cancer or inflammatory diseases, preferably for the treatment of systemic lupus erythematosus, or lupus nephritis. The invention comprises the use of the bispecific antibodies specifically binding to human TWEAK and human IL17 according to the invention for the treatment (or the bispecific antibodies for use in the treatment) of a patient suffering from cancer, especially from colon, lung, or pancreatic cancer or from autoimmune diseases, rheumatoid arthritis, psoratic arthritis, psoriasis, muscle diseases, e.g. muscular dystrophy, multiple sclerosis, chronic kidney diseases, bone diseases, e.g. bone degeneration in multiple myeloma, systemic lupus erythematosus, lupus nephritis, and vascular injury.

The invention comprises the use of the bispecific antibodies specifically binding to human TWEAK and human IL17 according to the invention for the treatment (or the bispecific antibodies for use in the treatment) of a patient suffering from systemic lupus erythematosus or lupus nephritis.

The invention comprises the use of the bispecific antibodies specifically binding to human TWEAK and human IL17 according to the invention for the treatment (or the bispecific antibodies for use in the treatment) of a variety of inflammatory, immune and proliferative disorders, including rheumatoid arthritis (RA), osteoarthritis, rheumatoid arthritis osteoporosis, inflammatory fibrosis (e.g. scleroderma, lung fibrosis, and cirrhosis), gingivitis, periodontitis or other inflammatory periodontal diseases, inflammatory bowel disorders (e.g. Crohn's disease, ulcerative colitis and inflammatory bowel disease), asthma (including allergic asthma), allergies, chronic obstructive pulmonary disease (COPD), multiple sclerosis, psoriasis and cancer, ankylosing spondylitis, systemic sclerosis, psoriatic arthritis, inflammatory arthritis, osteoarthritis, inflammatory joint disease, autoimmune disease including autoimmune vasculitis, multiple sclerosis, lupus, diabetes (e.g., insulin diabetes), inflammatory bowel disease, transplant rejection, graft vs. host disease, and inflammatory conditions resulting from strain, sprain, cartilage damage, trauma, orthopedic surgery, infection or other disease processes. Other diseases influenced by the dysfunction of the immune system are encompassed within the scope of the invention, including but not limited to, allergies.

Bispecific antibodies of the invention are particularly useful for the treatment, prevention, or amelioration of autoimmune disease and of inflammatory conditions, in particular inflammatory conditions with an aetiology including an autoimmune component such as arthritis (for example rheumatoid arthritis, arthritis chronica progrediente and arthritis deformans) and rheumatic diseases, including inflammatory conditions and rheumatic diseases involving bone loss, inflammatory pain, spondyloarhropathies including ankolsing spondylitis, Reiter syndrome, reactive arthritis, psoriatic arthritis, and enterophathis arthritis, hypersensitivity (including both airways hypersensitivity and dermal hypersensitivity) and allergies. Specific auto-immune diseases for which the bispecific antibodies as described herein may be employed include autoimmune haematological disorders (including e.g. hemolytic anaemia, aplastic anaemia, pure red cell anaemia and idiopathic thrombocytopenia), systemic lupus erythematosus, inflammatory muscle disorders, polychondritis, sclerodoma, Wegener granulomatosis, dermatomyositis, chronic active hepatitis, myasthenia gravis, psoriasis, Steven-Johnson syndrome, idiopathic sprue, autoimmune inflammatory bowel disease (including e.g. ulcerative colitis, Crohn's disease and Irritable Bowel Syndrome), endocrine ophthalmopathy, Graves' disease, sarcoidosis, multiple sclerosis, primary biliary cirrhosis, juvenile diabetes (diabetes mellitus type I), uveitis (anterior and posterior), keratoconjunctivitis sicca and vernal keratoconjunctivitis, interstitial lung fibrosis, psoriatic arthritis and glomerulonephritis (with and without nephrotic syndrome, e.g. including idiopathic nephrotic syndrome or minimal change nephropathy), tumors, multiple sclerosis, inflammatory disease of skin and cornea, myositis, loosening of bone implants, metabolic disorders, such as atherosclerosis, diabetes, and dislipidemia. The bispecific antibodies according to the invention are also useful for the treatment, prevention, or amelioration of asthma, bronchitis, pneumoconiosis, pulmonary emphysema, and other obstructive or inflammatory diseases of the airways.

The invention comprises also a method for the treatment of a patient suffering from such disease.

The invention further provides a method for the manufacture of a pharmaceutical composition comprising an effective amount of an antibody according to the invention together with a pharmaceutically acceptable carrier and the use of the antibody according to the invention for such a method.

The invention also provides the use of an antibody according to the invention in an effective amount for the manufacture of a pharmaceutical agent, preferably together with a pharmaceutically acceptable carrier, for the treatment of a patient suffering from cancer, especially from colon, lung, or pancreatic cancer or from autoimmune diseases, rheumatoid arthritis, psoratic arthritis, muscle diseases, e.g. muscular dystrophy, multiple sclerosis, chronic kidney diseases, bone diseases, e.g. bone degeneration in multiple myeloma, systemic lupus erythematosus, lupus nephritis, and vascular injury.

The invention also provides the use of an antibody according to the invention in an effective amount for the manufacture of a pharmaceutical agent, preferably together with a pharmaceutically acceptable carrier, for the treatment of a patient suffering from of autoimmune disease and of inflammatory conditions, in particular inflammatory conditions with an aetiology including an autoimmune component such as arthritis (for example rheumatoid arthritis, arthritis chronica progrediente and arthritis deformans) and rheumatic diseases, including inflammatory conditions and rheumatic diseases involving bone loss, inflammatory pain, spondyloarhropathies including ankolsing spondylitis, Reiter syndrome, reactive arthritis, psoriatic arthritis, and enterophathis arthritis, hypersensitivity (including both airways hypersensitivity and dermal hypersensitivity) and allergies. Specific auto-immune diseases for which the bispecific antibodies as described herein may be employed include autoimmune haematological disorders (including e.g. hemolytic anaemia, aplastic anaemia, pure red cell anaemia and idiopathic thrombocytopenia), systemic lupus erythematosus, inflammatory muscle disorders, polychondritis, sclerodoma, Wegener granulomatosis, dermatomyositis, chronic active hepatitis, myasthenia gravis, psoriasis, Steven-Johnson syndrome, idiopathic sprue, autoimmune inflammatory bowel disease (including e.g. ulcerative colitis, Crohn's disease and Irritable Bowel Syndrome), endocrine ophthalmopathy, Graves' disease, sarcoidosis, multiple sclerosis, primary biliary cirrhosis, juvenile diabetes (diabetes mellitus type I), uveitis (anterior and posterior), keratoconjunctivitis sicca and vernal keratoconjunctivitis, interstitial lung fibrosis, psoriatic arthritis and glomerulonephritis (with and without nephrotic syndrome, e.g. including idiopathic nephrotic syndrome or minimal change nephropathy), tumors, multiple sclerosis, inflammatory disease of skin and cornea, myositis, loosening of bone implants, metabolic disorders, such as atherosclerosis, diabetes, and dislipidemia. The bispecific antibodies according to the invention are also useful for the treatment, prevention, or amelioration of asthma, bronchitis, pneumoconiosis, pulmonary emphysema, and other obstructive or inflammatory diseases of the airways.

In another aspect, the present invention provides a composition, e.g. a pharmaceutical composition, containing a bispecific TWEAK/IL17 antibody as described herein, formulated together with a pharmaceutically acceptable carrier, e.g., for use in any of the above therapeutic methods.

As used herein, "pharmaceutically acceptable carrier" includes any and all solvents, dispersion media, coatings, antibacterial and antifungal agents, isotonic and absorption/ resorption delaying agents, and the like that are physiologically compatible. Preferably, the carrier is suitable for injection or infusion.

A composition of the present invention can be administered by a variety of methods known in the art. As will be appreciated by the skilled artisan, the route and/or mode of administration will vary depending upon the desired results.

Pharmaceutically acceptable carriers include sterile aqueous solutions or dispersions and sterile powders for the preparation of sterile injectable solutions or dispersion. The use of such media and agents for pharmaceutically active substances is known in the art. In addition to water, the carrier can be, for example, an isotonic buffered saline solution.

In another embodiment, a pharmaceutical formulation comprises any of the bispecific TWEAK/IL17 antibodies provided herein and at least one additional therapeutic agent, e.g., as described below.

Antibodies of the invention can be used either alone or in combination with other agents in a therapy. For instance, an antibody of the invention may be co-administered with at least one additional therapeutic agent. In certain embodiments, an additional therapeutic agent is a immunosuppressive or immunomodulating agents or other anti-inflammatory agents. For example, the bispecific antibodies as described herein may be used in combination with DMARD, e.g. Gold salts, sulphasalazine, antimalarias, methotrexate, D-penicillamine, azathioprine, mycophenolic acid, cyclosporine A, tacrolimus, sirolimus, minocycline, leflunomide, glococorticoids; a calcineurin inhibitor, e.g. cyclosporin A or FK 506; a modulator of lymphocyte recirculation, e.g. FTY720 and FTY720 analogs; a mTOR inhibitor, e.g. rapamycin, 40-O-(2-hydroxyethyl)-rapamycin, CCI779, ABT578, AP23573 or TAFA-93; an ascomycin having immuno-suppressive properties, e.g. ABT-281, ASM981, etc.; corticosteroids; cyclophosphamide; azathioprene; methotrexate; leflunomide; mizoribine; mycophenolic acid; myco-pheno-late mofetil; 15-deoxyspergualine or an immunosuppressive homologue, analogue or derivative thereof; immunosuppressive monoclonal antibodies, e.g., monoclonal antibodies to leukocyte receptors, e.g., MHC, CD2, CD3, CD4, CD7, CD8, CD25, CD28, CD40. CD45, CD58, CD80, CD86 or their ligands; other immunomodulatory compounds, e.g. a recombinant binding molecule having at least a portion of the extracellular domain of CTLA4 or a mutant thereof, e.g. an at least extracellular portion of CTLA4 or a mutant thereof joined to a non-CTLA4 protein sequence, e.g. CTLA4Ig (for ex. designated ATCC 68629) or a mutant thereof, e.g. LEA29Y; adhesion molecule inhibitors, e.g. LFA-1 antagonists, ICAM-1 or -3 antagonists, VCAM-4 antagonists or VLA-4 antagonists; or a chemotherapeutic agent, e.g. paclitaxel, gemcitabine, cisplatinum, doxorubicin or 5-fluorouracil; anti TNF agents, e.g. monoclonal antibodies to TNF, e.g. infliximab, adalimumab, CDP870, or receptor constructs to TNF-RI or TNF-RII, e.g. Etanercept, PEG-TNF-RI; blockers of proinflammatory cytokines, IL-1 blockers, e.g. Anakinra or IL-1 trap, AAL160, ACZ 885, IL-6 blockers; chemokines blockers, e.g. inhibitors or activators of proteases, e.g. metalloproteases, anti-IL-15 antibodies, anti-IL-6 antibodies, anti-IL-23 antibodies, anti-CD20 antibodies, NSAIDs, such as aspirin or an anti-infectious agent (the list not limited to the agent mentioned).

Such combination therapies noted above encompass combined administration (where two or more therapeutic agents are included in the same or separate formulations), and separate administration, in which case, administration of the antibody of the invention can occur prior to, simultaneously, and/or following, administration of the additional therapeutic agent and/or adjuvant.

An antibody of the invention (and any additional therapeutic agent) can be administered by any suitable means, including parenteral, intrapulmonary, and intranasal, and, if desired for local treatment, intralesional administration. Parenteral infusions include intramuscular, intravenous, intraarterial, intraperitoneal, or subcutaneous administration. Dosing can be by any suitable route, e.g. by injections, such as intravenous or subcutaneous injections, depending in part on whether the administration is brief or chronic. Various dosing schedules including but not limited to single or multiple administrations over various time-points, bolus administration, and pulse infusion are contemplated herein.

Antibodies of the invention would be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The antibody need not be, but is optionally formulated with one or more agents currently used to prevent or treat the disorder in question. The effective amount of such other agents depends on the amount of antibody present in the formulation, the type of disorder or treatment, and other factors discussed above. These are generally used in the same dosages and with administration routes as described herein, or about from 1 to 99% of the dosages described herein, or in any dosage and by any route that is empirically/clinically determined to be appropriate.

For the prevention or treatment of disease, the appropriate dosage of an antibody of the invention (when used alone or in combination with one or more other additional therapeutic agents) will depend on the type of disease to be treated, the type of antibody, the severity and course of the disease, whether the antibody is administered for preventive or therapeutic purposes, previous therapy, the patient's clinical history and response to the antibody, and the discretion of the attending physician. The antibody is suitably administered to the patient at one time or over a series of treatments. Depending on the type and severity of the disease, about 1 µg/kg to 15 mg/kg (e.g. 0.5 mg/kg-10 mg/kg) of antibody can be an initial candidate dosage for administration to the patient, whether, for example, by one or more separate administrations, or by continuous infusion. One typical daily dosage might range from about 1 µg/kg to 100 mg/kg or more, depending on the factors mentioned above. For repeated administrations over several days or longer, depending on the condition, the treatment would generally be sustained until a desired suppression of disease symptoms occurs. One exemplary dosage of the antibody would be in the range from about 0.05 mg/kg to about 10 mg/kg. Thus, one or more doses of about 0.5 mg/kg, 2.0 mg/kg, 4.0 mg/kg or 10 mg/kg (or any combination thereof) may be administered to the patient. Such doses may be administered intermittently, e.g. every week or every three weeks (e.g. such that the patient receives from about two to about twenty, or e.g. about six doses of the antibody). An initial higher loading dose, followed by one or more lower doses may be administered. An exemplary dosing regimen comprises administering. However, other dosage regimens may be useful. The progress of this therapy is easily monitored by conventional techniques and assays.

Regardless of the route of administration selected, the compounds of the present invention, which may be used in a suitable hydrated form, and/or the pharmaceutical compositions of the present invention, are formulated into pharmaceutically acceptable dosage forms by conventional methods known to those of skill in the art.

Actual dosage levels of the active ingredients in the pharmaceutical compositions of the present invention may be varied so as to obtain an amount of the active ingredient which is effective to achieve the desired therapeutic response for a particular patient, composition, and mode of administration, without being toxic to the patient (effective amount). The selected dosage level will depend upon a variety of pharmacokinetic factors including the activity of the particular compositions of the present invention employed, or the ester, salt or amide thereof, the route of administration, the time of administration, the rate of excretion of the particular compound being employed, other drugs, compounds and/or materials used in combination with the particular compositions employed, the age, sex, weight, condition, general health and prior medical history of the patient being treated, and like factors well known in the medical arts.

Articles of Manufacture

In another aspect of the invention, an article of manufacture containing materials useful for the treatment, prevention and/or diagnosis of the disorders described above is provided. The article of manufacture comprises a container and a label or package insert on or associated with the container. Suitable containers include, for example, bottles, vials, syringes, IV solution bags, etc. The containers may be formed from a variety of materials such as glass or plastic. The container holds a composition which is by itself or combined with another composition effective for treating, preventing and/or diagnosing the condition and may have a sterile access port (for example the container may be an intravenous solution bag or a vial having a stopper pierceable by a hypodermic injection needle). At least one active agent in the composition is an antibody of the invention. The label or package insert indicates that the composition is used for treating the condition of choice. Moreover, the article of manufacture may comprise (a) a first container with a composition contained therein, wherein the composition comprises an antibody of the invention; and (b) a second container with a composition contained therein, wherein the composition comprises a further cytotoxic or otherwise therapeutic agent. The article of manufacture in this embodiment of the invention may further comprise a package insert indicating that the compositions can be used to treat a particular condition. Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

Description of the Sequences

| | | |
|---|---|---|
| SEQ ID NO: | 1 | CDR1H <TWEAK> 301 |
| SEQ ID NO: | 2 | CDR2H <TWEAK> 301 |
| SEQ ID NO: | 3 | CDR3H <TWEAK> 301 |
| SEQ ID NO: | 4 | CDR1L <TWEAK> 301 |
| SEQ ID NO: | 5 | CDR2L <TWEAK> 301 |
| SEQ ID NO: | 6 | CDR3L <TWEAK> 301 |
| SEQ ID NO: | 7 | Rabbit variable heavy chain domain (VH) <TWEAK> 301 |
| SEQ ID NO: | 8 | Rabbit variable light chain domain (VL) <TWEAK> 301 |
| SEQ ID NO: | 9 | CDR1H <TWEAK> 304 |
| SEQ ID NO: | 10 | CDR2H <TWEAK> 304 |
| SEQ ID NO: | 11 | CDR3H <TWEAK> 304 |
| SEQ ID NO: | 12 | CDR1L <TWEAK> 304 |
| SEQ ID NO: | 13 | CDR2L <TWEAK> 304 |
| SEQ ID NO: | 14 | CDR3L <TWEAK> 304 |
| SEQ ID NO: | 15 | Rabbit variable heavy chain domain (VH) <TWEAK> 304 |
| SEQ ID NO: | 16 | Rabbit variable light chain domain (VL) <TWEAK> 304 |
| SEQ ID NO: | 17 | CDR1H <TWEAK> 305 |
| SEQ ID NO: | 18 | CDR2H <TWEAK> 305 |
| SEQ ID NO: | 19 | CDR3H <TWEAK> 305 |
| SEQ ID NO: | 20 | CDR1L <TWEAK> 305 |
| SEQ ID NO: | 21 | CDR2L <TWEAK> 305 |
| SEQ ID NO: | 22 | CDR3L <TWEAK> 305 |
| SEQ ID NO: | 23 | Rabbit variable heavy chain domain (VH) <TWEAK> 305 |
| SEQ ID NO: | 24 | Rabbit variable light chain domain (VL) <TWEAK> 305 |
| SEQ ID NO: | 25 | Humanized variant of VH, <TWEAK> 305-HC1 |
| SEQ ID NO: | 26 | Humanized variant of VH, <TWEAK> 305-HC2 |
| SEQ ID NO: | 27 | Humanized variant of VH, <TWEAK> 305-HC3 |
| SEQ ID NO: | 28 | Humanized variant of VH, <TWEAK> 305-HC4 |
| SEQ ID NO: | 29 | Humanized variant of VH, <TWEAK> 305-HC5 |
| SEQ ID NO: | 30 | Humanized variant of VH, <TWEAK> 305-HC6 |
| SEQ ID NO: | 31 | Humanized variant of VH, <TWEAK> 305-HC7 |
| SEQ ID NO: | 32 | Humanized variant of VH, <TWEAK> 305-HC8 |
| SEQ ID NO: | 33 | Humanized variant of VH, <TWEAK> 305-HC9 |
| SEQ ID NO: | 34 | Humanized variant of VH, <TWEAK> 305-HC10 |
| SEQ ID NO: | 35 | Humanized variant of VH, <TWEAK> 305-HC11 |
| SEQ ID NO: | 36 | Humanized variant of VL, <TWEAK> 305-LC1 |
| SEQ ID NO: | 37 | Humanized variant of VL, <TWEAK> 305-LC2 |
| SEQ ID NO: | 38 | Humanized variant of VL, <TWEAK> 305-LC3 |
| SEQ ID NO: | 39 | Humanized variant of VL, <TWEAK> 305-LC4 |
| SEQ ID NO: | 40 | Humanized variant of VL, <TWEAK> 305-LC5 |
| SEQ ID NO: | 41 | Humanized variant of VL, <TWEAK> 305-LC6 |
| SEQ ID NO: | 42 | Humanized variant of VL, <TWEAK> 305-LC7 |
| SEQ ID NO: | 43 | Humanized variant of VL, <TWEAK> 305-LC8 |
| SEQ ID NO: | 44 | Humanized variant of VL, <TWEAK> 305-LC9 |

| | | |
|---|---|---|
| SEQ ID NO: | 45 | Humanized variant of VL, <TWEAK> 305-LC10 |
| SEQ ID NO: | 46 | Humanized variant of VL, <TWEAK> 305-LC11 |
| SEQ ID NO: | 47 | CDR1H <IL17> 9C6-2B6 |
| SEQ ID NO: | 48 | CDR2H <IL17> 9C6-2B6 |
| SEQ ID NO: | 49 | CDR3H <IL17> 9C6-2B6 |
| SEQ ID NO: | 50 | CDR1L <IL17> 9C6-2B6 |
| SEQ ID NO: | 51 | CDR2L <IL17> 9C6-2B6 |
| SEQ ID NO: | 52 | CDR3L <IL17> 9C6-2B6 |
| SEQ ID NO: | 53 | Mouse variable heavy chain domain (VH), <IL17> 9C6-2B6 |
| SEQ ID NO: | 54 | Mouse variable light chain domain (VH), <IL17> 9C6-2B6 |
| SEQ ID NO: | 55 | Humanized variant of VH, <IL17> 9C6-2B6-HC134 |
| SEQ ID NO: | 56 | Humanized variant of VH, <IL17> 9C6-2B6-HC136 |
| SEQ ID NO: | 57 | Humanized variant of VL, <IL17> 9C6-2B6-LC134 |
| SEQ ID NO: | 58 | Humanized variant of VL, <IL17> 9C6-2B6-LC136 |
| SEQ ID NO | 59 | Human kappa light chain constant region |
| SEQ ID NO | 60 | Human lambda light chain constant region |
| SEQ ID NO | 61 | Human IgG1 (Caucasian Allotype) constant region |
| SEQ ID NO | 62 | Human IgG1 (Afroamerican Allotype) constant region |
| SEQ ID NO | 63 | Human IgG1 L234A/L235A Mutant (Caucasian Allotype) |
| SEQ ID NO | 64 | Human IgG1 L234A/L235A/P329G Mutant (Caucasian Allotype) |
| SEQ ID NO | 65 | Human IgG4 constant region |
| SEQ ID NO | 66 | Human IgG4 S228P/L235E Mutant |
| SEQ ID NO | 67 | Human IgG4 S228P/L235E/P329G Mutant |
| SEQ ID NO | 68 | Human TWEAK |
| SEQ ID NO | 69 | Murine TWEAK |
| SEQ ID NO | 70 | Human IL17 (IL17A) |
| SEQ ID NO | 71 | Human IL17B |
| SEQ ID NO | 72 | Human IL17C |
| SEQ ID NO | 73 | Human IL17D |
| SEQ ID NO | 74 | Human IL17E |
| SEQ ID NO | 75 | Human IL17F |
| SEQ ID NO | 76 | Bispecific <Tweak-IL-17> #2 antibody- heavy chain construct 1 |
| SEQ ID NO | 77 | Bispecific <Tweak-IL-17> #2 antibody- heavy chain construct 2 |
| SEQ ID NO | 78 | Bispecific <Tweak-IL-17> #2 anitbody- light chain construct 1 |
| SEQ ID NO | 79 | Bispecific <Tweak-IL-17> #2 antibody- lght chain construct 2 |
| SEQ ID NO | 80 | Bispecific <Tweak-IL-17> #4 antibody- heavy chain construct 1 |
| SEQ ID NO | 81 | Bispecific <Tweak-IL-17> #4 antibody- heavy chain construct 2 |
| SEQ ID NO | 82 | Bispecific <Tweak-IL-17> #4 antibody- light chain construct 1 |
| SEQ ID NO | 83 | Bispecific <Tweak-IL-17> #5 antibody-heavy chain construct |
| SEQ ID NO | 84 | Bispecific <Tweak-IL-17> #5 antibody- light chain construct |
| SEQ ID NO | 85 | Bispecific <Tweak-IL-17> #20 antibody- heavy chain construct 1 |
| SEQ ID NO | 86 | Bispecific <Tweak-IL-17> #20 antibody- heavy chain construct 2 |
| SEQ ID NO | 87 | Bispecific <Tweak-IL-17> #20 antibody- light chain construct 1 |
| SEQ ID NO | 88 | Bispecific <Tweak-IL-17> #21 antibody- heavy chain construct 1 |
| SEQ ID NO | 89 | Bispecific <Tweak-IL-17> #21 antibody- heavy chain construct 2 |
| SEQ ID NO | 90 | Bispecific <Tweak-IL-17> #21 antibody- light chain construct 1 |
| SEQ ID NO | 91 | Bispecific <Tweak-IL-17> #23 antibody- heavy chain construct 1 |
| SEQ ID NO | 92 | Bispecific <Tweak-IL-17> #23 antibody- heavy chain construct 2 |
| SEQ ID NO | 93 | Bispecific <Tweak-IL-17> #23 antibody- light chain construct 1 |
| SEQ ID NO | 94 | Bispecific <Tweak-IL-17> #24 antibody- heavy chain construct 1 |
| SEQ ID NO | 95 | Bispecific <Tweak-IL-17> #24 antibody- heavy chain construct 2 |
| SEQ ID NO | 96 | Bispecific <Tweak-IL-17> #24 antibody- light chain construct 1 |
| SEQ ID NO | 97 | Bispecific <Tweak-IL-17> #24 antibody- light chain construct 2 |
| SEQ ID NO | 98 | Human Fn14 (TWEAK receptor) |
| SEQ ID NO | 99 | Human IL6 |
| SEQ ID NO | 100 | Human IL8 |

In the Following, Embodiments of the Invention are Listed

1. A bispecific antibody comprising a first antigen-binding site that specifically binds to human TWEAK and a second antigen-binding site that specifically binds to human IL17.
2. The bispecific, bivalent antibody according to embodiment 1, wherein the bispecific antibody inhibits
   a) TWEAK induced proliferation of human fibroblast-like synoviocytes-rheumatoid arthritis (HFLS-RA) with an IC50 value of 0.2 nM or lower; and
   b) IL17 induced IL6 cytokine stimulation of human fibroblast-like synoviocytes-rheumatoid arthritis (HFLS-RA) with an IC50 value of 3.0 nM or lower; and
   c) IL17 induced IL8 cytokine stimulation of human fibroblast-like synoviocytes-rheumatoid arthritis (HFLS-RA) with an IC50 value of 2.0 nM or lower.
3. The bispecific, bivalent antibody according to embodiment 1, characterized in that the bispecific antibody is bivalent.
4. The bispecific antibody according to any of embodiments 1 to 3, characterized in that
   i) said first antigen-binding site comprises
   a) CDR1H of SEQ ID NO:17, CDR2H of SEQ ID NO:18, CDR3H of SEQ ID NO:19, and CDR1L of SEQ ID NO:20, CDR2L of SEQ ID NO:21, CDR3L of SEQ ID NO:22; or
   b) CDR1H of SEQ ID NO:1, CDR2H of SEQ ID NO:2, CDR3H of SEQ ID NO:3, and CDR1L of SEQ ID NO:4, CDR2L of SEQ ID NO:5, CDR3L of SEQ ID NO:6; or c) CDR1H of SEQ ID NO:9, CDR2H of SEQ ID NO:10, CDR3H of SEQ ID NO:11, and CDR1L of SEQ ID NO:12, CDR2L of SEQ ID NO:13, CDR3L of SEQ ID NO:14; and
ii) said second antigen-binding site comprises CDR1H of SEQ ID NO:47, CDR2H of SEQ ID NO:48, CDR3H of SEQ ID NO:49, and CDR1L of SEQ ID NO:50, CDR2L of SEQ ID NO:51, CDR3L of SEQ ID NO:52.

5. A chimeric or humanized variant of the bispecific, antibody according to embodiment 4.

6. The bispecific antibody according to any of embodiments 1 to 3, characterized in that
i) said first antigen-binding site comprises
a variable heavy chain domain (VH) of SEQ ID NO:25, of SEQ ID NO:26, of SEQ ID NO:27, of SEQ ID NO:28, of SEQ ID NO:29, of SEQ ID NO:30, of SEQ ID NO:31, of SEQ ID NO:32, of SEQ ID NO:33, of SEQ ID NO:34, or of SEQ ID NO:35, and a variable light chain domain of SEQ ID NO:26, of SEQ ID NO:37, of SEQ ID NO:38, of SEQ ID NO:39, of SEQ ID NO:40, of SEQ ID NO:41, of SEQ ID NO:42, of SEQ ID NO:43, of SEQ ID NO:44, of SEQ ID NO:45, or of SEQ ID NO:46; and
ii) said second antigen-binding site comprises
a variable heavy chain domain (VH) of SEQ ID NO:55, or of SEQ ID NO:56, and a variable light chain domain of SEQ ID NO:57, or of SEQ ID NO:58.

7. The bispecific antibody according to any of embodiments 1 to 3, characterized in that
i) said first antigen-binding site comprises
a variable heavy chain domain (VH) of SEQ ID NO:28, and a variable light chain domain of SEQ ID NO:37; and
ii) said second antigen-binding site comprises
a) a variable heavy chain domain (VH) of SEQ ID NO:56, and a variable light chain domain of SEQ ID NO:58; or
b) a variable heavy chain domain (VH) of SEQ ID NO:55, and a variable light chain domain of SEQ ID NO:57.

8. The bispecific antibody according to any of embodiments 1 to 3, characterized in that
i) said first antigen-binding site comprises
a variable heavy chain domain (VH) of SEQ ID NO:28, and a variable light chain domain of SEQ ID NO:37; and
ii) said second antigen-binding site comprises
a variable heavy chain domain (VH) of SEQ ID NO:56, and a variable light chain domain of SEQ ID NO:58.

9. The bispecific antibody according to any of embodiments 1 to 3, characterized in that
i) said first antigen-binding site comprises
a variable heavy chain domain (VH) of SEQ ID NO:28, and a variable light chain domain of SEQ ID NO:37; and
ii) said second antigen-binding site comprises
a variable heavy chain domain (VH) of SEQ ID NO:55, and a variable light chain domain of SEQ ID NO:57.

10. The bispecific antibody according to any of the preceding embodiments, characterized in that it is of IgG1 or IgG4 subclass.

11. The bispecific antibody according to any of the preceding embodiments, characterized in being of IgG1 subclass with the mutations L234A and L235A (numbering according to the EU index of Kabat).

12. The bispecific antibody according to any of the preceding embodiments, characterized in being of IgG1 subclass with the mutations L234A, L235A and P329G (numbering according to the EU index of Kabat).

13. The bispecific antibody according to any of the preceding embodiments, characterized in being of IgG4 subclass with the mutations S228P and L235E (numbering according to the EU index of Kabat).

14. The bispecific antibody according to any of the preceding embodiments, characterized in being of IgG4 subclass with the mutations S228P, L235E and P329G (numbering according to the EU index of Kabat).

15. Pharmaceutical composition characterized by comprising an antibody according to embodiments 1 to 14.

16. Use of an antibody according to embodiments 1 to 14 for the manufacture of a pharmaceutical composition.

17. An antibody according to embodiments 1 to 14 for use in the treatment of cancer, or inflammatory diseases, autoimmune diseases, rheumatoid arthritis, psoratic arthritis, muscle diseases, e.g. muscular dystrophy, multiple sclerosis, chronic kidney diseases, bone diseases, e.g. bone degeneration in multiple myeloma, systemic lupus erythematosus, lupus nephritis, and vascular injury.

18. Use of an antibody according to embodiments 1 to 14 for manufacture of a medicament for the treatment of cancer, or inflammatory diseases, autoimmune diseases, rheumatoid arthritis, psoratic arthritis, muscle diseases, e.g. muscular dystrophy, multiple sclerosis, chronic kidney diseases, bone diseases, e.g. bone degeneration in multiple myeloma, systemic lupus erythematosus, lupus nephritis, and vascular injury.

19. Nucleic acid encoding an antibody according to embodiments 1 to 14.

20. Expression vectors characterized by comprising a nucleic acid according to embodiment 19 for the expression of the bispecific antibody according to embodiments 1 to 14 in a prokaryotic or eukaryotic host cell.

21. Prokaryotic or eukaryotic host cell comprising a vector according to embodiment 20.

22. Method for the production of a recombinant antibody according to embodiments 1 to 14, characterized by expressing a nucleic acid according to embodiment 19 in a prokaryotic or eukaryotic host cell and recovering said antibody from said cell or the cell culture supernatant.

23. Method for the treatment of a patient suffering from cancer or from inflammatory diseases, autoimmune diseases, rheumatoid arthritis, psoratic arthritis, muscle diseases, e.g. muscular dystrophy, multiple sclerosis, chronic kidney diseases, bone diseases, e.g. bone degeneration in multiple myeloma, systemic lupus erythematosus, lupus nephritis, and vascular injury, characterized by administering to the patient an antibody according to embodiments 1 to 14.

The following examples, figures and sequence listing are provided to aid the understanding of the present invention, the true scope of which is set forth in the appended claims. It is understood that modifications can be made in the procedures set forth without departing from the spirit of the invention.

EXAMPLES

Materials & General Methods

General information regarding the nucleotide sequences of human immunoglobulins light and heavy chains is given in: Kabat, E. A., et al., Sequences of Proteins of Immunological Interest, 5th ed., Public Health Service, National Institutes of Health, Bethesda, Md. (1991). Amino acids of antibody constant chains are numbered and referred to according to EU index according to Kabat (Kabat, E. A., et al., Sequences of Proteins of Immunological Interest, 5th ed., Public Health Service, National Institutes of Health, Bethesda, Md., (1991)).

Recombinant DNA Techniques

Standard methods were used to manipulate DNA as described in Sambrook, J., et al., Molecular Cloning: A Laboratory Manual; Cold Spring Harbor Laboratory Press, Cold Spring Harbor, N.Y. (1989). The molecular biological reagents were used according to the manufacturer's instructions.

Gene Synthesis

Desired gene segments can be prepared from oligonucleotides made by chemical synthesis. The gene segments, which are flanked by singular restriction endonuclease cleavage sites, were assembled by annealing and ligation of oligonucleotides including PCR amplification and subsequently cloned via the indicated restriction sites e.g. KpnI/SacI or AscI/PacI into a pPCRScript (Stratagene) based pGA4 cloning vector. The DNA sequences of the subcloned gene fragments were confirmed by DNA sequencing.

Gene synthesis fragments were ordered according to given specifications at Geneart (Regensburg, Germany). All gene segments encoding light and heavy chains of Tweak/IL-17 bispecific antibodies were synthesized with a 5'-end DNA sequence coding for a leader peptide which targets proteins for secretion in eukaryotic cells, and unique restriction sites at the 5' and 3' ends of the synthesized gene. DNA sequences carrying disulfide stabilized "knobs-into-hole" modified heavy chains were designed with S354C and T366W mutations in the "knobs" heavy chain and Y349C, T366S, L368A and Y407V mutations in the "hole" heavy chain.

DNA Sequence Determination

DNA sequences were determined by double strand sequencing performed at MediGenomix GmbH (Martinsried, Germany) or Sequiserve GmbH (Vaterstetten, Germany).

DNA and Protein Sequence Analysis and Sequence Data Management

The GCG's (Genetics Computer Group, Madison, Wis.) software package version 10.2 and Infomax's Vector NT1 Advance suite version 11.5 was used for sequence creation, mapping, analysis, annotation and illustration.

Expression Vectors

For the expression of the described antibodies variants of expression plasmids for transient expression (e.g. in HEK293 EBNA or HEK293-F cells) or for stable expression (e.g. in CHO cells) based either on a cDNA organization with a CMV-Intron A promoter or on a genomic organization with a CMV promoter were applied.

In case of IgG4_SPLE the intron between the CH1 domain and the hinge domain was removed, keeping the remainder of the antibody gene in a genomic organization. The intron-deleted version of IgG4_SPLE no longer shows hingeless antibodies as a result of a splice artefact commonly seen in IgG4_SPLE encoded in total genomic organization.

Beside the antibody expression cassette the vectors contained:

an origin of replication which allows replication of this plasmid in *E. coli*, and a β-lactamase gene which confers ampicillin resistance in *E. coli*.

The transcription unit of the antibody gene is composed of the following elements:
unique restriction site(s) at the 5' end
the immediate early enhancer and promoter from the human cytomegalovirus,
followed by the Intron A sequence in the case of the cDNA organization,
a 5'-untranslated region of a human antibody gene,
an immunoglobulin heavy chain signal sequence,
the human antibody chain (heavy chain, modified heavy chain or light chain) either as cDNA or as genomic organization with an the immunoglobulin exon-intron organization
a 3' untranslated region with a polyadenylation signal sequence, and
unique restriction site(s) at the 3'end. For transient and stable transfections larger quantities of the plasmids were prepared by plasmid preparation from transformed *E. coli* cultures (Nucleobond AX, Macherey-Nagel).

Cell Culture Techniques

Standard cell culture techniques were used as described in Current Protocols in Cell Biology (2000), Bonifacino, J. S., Dasso, M., Harford, J. B., Lippincott-Schwartz, J. and Yamada, K. M. (eds.), John Wiley & Sons, Inc.

Transient Transfections in HEK293-F System

Recombinant immunoglobulin variants were expressed by transient transfection of human embryonic kidney 293-F cells using the FreeStyle™ 293 Expression System according to the manufacturer's instruction (Invitrogen, USA). Briefly, suspension FreeStyle™ 293-F cells were cultivated in FreeStyle™ 293 Expression medium at 37° C./8% $CO_2$ and the cells were seeded in fresh medium at a density of $1-2 \times 10^6$ viable cells/ml on the day of transfection. DNA-293Fectin™ complexes were prepared in Opti-MEM® I medium (Invitrogen, USA) using 325 μl of 293Fectin™ (Invitrogen, Germany) and 250 μg of heavy and light chain plasmid DNA in a 1:1 molar ratio for a 250 ml final transfection volume for monospecific parent antibodies. "Knobs-into-hole" DNA-293fectin complexes with two heavy chains and one light chain were prepared in Opti-MEM® I medium (Invitrogen, USA) using 325 μl of 293Fectin™ (Invitrogen, Germany) and 250 μg of "Knobs-into-hole" heavy chain 1 and 2 and light chain plasmid DNA generally in a 1:1:1 molar ratio for a 250 ml final transfection volume (For format described in WO2011/117330 ("bispecific one-armed scFab antibodies")). For expression yield and product quality optimization the ratio can be varied. DNA-293fectin complexes were prepared in Opti-MEM® I medium (Invitrogen, USA) using 325 μl of 293Fectin™ (Invitrogen, Germany) and 250 μg of "Knobs-into-hole" heavy chain 1 and 2 and light chain 1 and 2 plasmid DNA in a 1:1:1:1 molar ratio for a 250 ml final transfection volume (For the format described in WO 2009/080253 ("CrossMabs" or "CH1-CL domain exchanged antibodies")). For expression yield and product quality optimization the ratio can be varied. Antibody containing cell culture supernatants were harvested 7 days after transfection by centrifugation at 14000 g for 30 minutes and filtered through a sterile filter (0.22 μm). Supernatants were stored at −20° C. until purification.

Protein Determination

The protein concentration of purified antibodies and derivatives was determined by determining the optical density (OD) at 280 nm, using the molar extinction coefficient calculated on the basis of the amino acid sequence according to Pace, C. N., et. al., Protein Science 4 (1995) 2411-1423.

Antibody Concentration Determination in Supernatants

The concentration of antibodies and derivatives in cell culture supernatants was estimated by immunoprecipitation with Protein A Agarose-beads (Roche). 60 µL Protein A Agarose beads are washed three times in TBS-NP40 (50 mM Tris, pH 7.5, 150 mM NaCl, 1% Nonidet-P40). Subsequently, 1-15 mL cell culture supernatant are applied to the Protein A Agarose beads pre-equilibrated in TBS-NP40. After incubation for at 1 h at room temperature the beads are washed on an Ultrafree-MC-filter column (Amicon] once with 0.5 mL TBS-NP40, twice with 0.5 mL 2× phosphate buffered saline (2×PBS, Roche) and briefly four times with 0.5 mL 100 mM Na-citrate pH 5.0. Bound antibody is eluted by addition of 35 µl NuPAGE® LDS Sample Buffer (Invitrogen). Half of the sample is combined with NuPAGE® Sample Reducing Agent or left unreduced, respectively, and heated for 10 min at 70° C. Consequently, 20 µl are applied to an 4-12% NuPAGE® Bis-Tris SDS-PAGE (Invitrogen) (with MOPS buffer for non-reduced SDS-PAGE and MES buffer with NuPAGE® Antioxidant running buffer additive (Invitrogen) for reduced SDS-PAGE) and stained with Coomassie Blue.

The concentration of antibodies and derivatives in cell culture supernatants was measured by Protein A-HPLC chromatography. Briefly, cell culture supernatants containing antibodies and derivatives that bind to Protein A were applied to a HiTrap Protein A column (GE Healthcare) in 50 mM K2HPO4, 300 mM NaCl, pH 7.3 and eluted from the matrix with 550 mM acetic acid, pH 2.5 on a Dionex HPLC-System. The eluted protein was quantified by UV absorbance and integration of peak areas. A purified standard IgG1 antibody served as a standard.

Alternatively, the concentration of antibodies and derivatives in cell culture supernatants was measured by Sandwich-IgG-ELISA. Briefly, StreptaWell High Bind Strepatavidin A-96 well microtiter plates (Roche) were coated with 100 µL/well biotinylated anti-human IgG capture molecule F(ab')2<h-Fcgamma> BI (Dianova) at 0.1 µg/mL for 1 h at room temperature or alternatively over night at 4° C. and subsequently washed three times with 200 µL/well PBS, 0.05% Tween (PBST, Sigma). 100 µL/well of a dilution series in PBS (Sigma) of the respective antibody containing cell culture supernatants was added to the wells and incubated for 1-2 h on a microtiterplate shaker at room temperature. The wells were washed three times with 200 µL/well PBST and bound antibody was detected with 100 µl F(ab')2<hFcgamma>POD (Dianova) at 0.1 µg/mL as detection antibody for 1-2 h on a microtiterplate shaker at room temperature. Unbound detection antibody was washed away three times with 200 µL/well PBST and the bound detection antibody was detected by addition of 100 µL ABTS/well. Determination of absorbance was performed on a Tecan Fluor Spectrometer at a measurement wavelength of 405 nm (reference wavelength 492 nm).

Purification of Bispecific Antibodies

Bispecific antibodies were purified from cell culture supernatants by affinity chromatography using Protein A-Sepharose™ (GE Healthcare, Sweden) and Superdex200 size exclusion chromatography. Briefly, sterile filtered cell culture supernatants were applied on a HiTrap ProteinA HP (5 ml) column equilibrated with PBS buffer (10 mM $Na_2HPO_4$, 1 mM $KH_2PO_4$, 137 mM NaCl and 2.7 mM KCl, pH 7.4). Unbound proteins were washed out with equilibration buffer. Antibody and antibody variants were eluted with 0.1 M citrate buffer, pH 2.8, and the protein containing fractions were neutralized with 0.1 ml 1 M Tris, pH 8.5. Then, the eluted protein fractions were pooled, concentrated with an Amicon Ultra centrifugal filter device (MWCO: 30 K, Millipore) to a volume of 3 ml and loaded on a Superdex200 HiLoad 120 ml 16/60 gel filtration column (GE Healthcare, Sweden) equilibrated with 20 mM Histidin, 140 mM NaCl, pH 6.0. Fractions containing purified bispecific antibodies with less than 5% high molecular weight aggregates were pooled and stored as 1.0 mg/ml aliquots at −80° C.

SDS-PAGE

The NuPAGE® Pre-Cast gel system (Invitrogen) was used according to the manufacturer's instruction. In particular, 4-20% NuPAGE® Novex® TRIS-Glycine Pre-Cast gels and a Novex® TRIS-Glycine SDS running buffer were used. Reducing of samples was achieved by adding NuPAGE® sample reducing agent prior to running the gel.

Analytical Size Exclusion Chromatography

Size exclusion chromatography for the determination of the aggregation and oligomeric state of antibodies was performed by HPLC chromatography. Briefly, Protein A purified antibodies were applied to a Tosoh TSKgel G3000SW column in 300 mM NaCl, 50 mM KH2PO4/K2HPO4, pH 7.5 on an Agilent HPLC 1100 system or to a Superdex 200 column (GE Healthcare) in 2×PBS on a Dionex HPLC-System. The eluted protein was quantified by UV absorbance and integration of peak areas. BioRad Gel Filtration Standard 151-1901 served as a standard.

Mass Spectrometry

The total deglycosylated mass of the bispecific antibodies was determined and confirmed via electrospray ionization mass spectrometry (ESI-MS). Moreover potential sideproducts such as LC and HC mispairing were detected and relatively quantified. Briefly, 100 µg purified antibodies at a protein concentration of up to 3 mg/ml were deglycosylated with 14 or 28 U N-Glycosidase F (Roche) in 100 mM NaH2PO4/Na2HPO4, pH 7 at 37 or 45° C. for 16 or 2 h and subsequently desalted via HPLC on a Sephadex G25 column (GE Healthcare). The mass of the respective heavy and light chains was determined by ESI-MS after deglycosylation and reduction. In brief, 50 µg antibody in 115 µl were incubated at 37° C. for 30 min with 60 µl 0.5 M TCEP in 4 M Guanidine-hydrochloride and 50 µl 8 M Guanidine-hydrochloride and subsequently desalted. The total mass and the mass of the reduced heavy and light chains were determined via ESI-MS on a maXis UHR-TOF (Bruker) MS system equipped with a TriVersa NanoMate (Advion) source.

Example 1

Generation of TWEAK Antigen Binding Sites Via Immunization (Generation of Parent TWEAK Antibodies from which the TWEAK Antigen Binding Sites for the TWEAK/IL17 Bispecific Antibodies Can be Derived)

Immunization of Rabbits with Human/Murine TWEAK

New Zealand White rabbits (*Oryctolagus cuniculus*) were immunized with 400 µg of recombinant human TWEAK at day 0 with complete Freund's adjuvant, with 200 μg of human TWEAK at days 21, 43 and 65 with incomplete Freund's adjuvant and with 200 μg of murine TWEAK at day 85 with incomplete Freund's adjuvant. All immunizations were done subcutaneously at several sites. Sera were prepared at days 77 and 98 for titer determination. The final boost was done by intravenous injection of 200 μg of human and 200 μg of murine soluble TWEAK and antibodies were selected based on their ability to bind human and mouse TWEAK (Example 2), neutralize human and mouse TWEAK-Fn14 interaction (Examples 4 and 5), and inhibit IL8 secretion (Example 6). In addition, the half-life of the antibody-TWEAK complex was investigated (Example 3). Anti-tumor efficacy of the antibody was tested in B16BL6 (murine melanoma; metastatic lung subline of B16), SJSA (osteosarcoma, ATCC CRL-2098) and HCT-116 (colon, ATCC CCL-247) xenograft models.

Example 2

Binding to Human and Mouse TWEAK (ELISA)

Binding of parent anti-TWEAK antibodies to human and mouse TWEAK was determined by ELISA. Human or mouse recombinant TWEAK were immobilized on a 384-well Nunc Maxisorp plate at 1 μg/ml, 25 μl/well, in 0.5 M carbonate coating buffer, pH 9.5, by incubation overnight at 2-8° C. Blocking of the plate with PBS/1% BSA for 1 h at room temperature was followed by two wash steps (0.1% Tween® 20 in PBS) and incubation with anti-TWEAK antibodies at different concentrations in blocking buffer or hybridoma supernatants of said antibodies for 1 h at room temperature. After further four washes, antibodies were detected with anti-rabbit-HRP antibody diluted 1:5000 in blocking buffer, for 1 h at room temperature. Signal was developed by addition of ABTS® (Roche Diagnostics GmbH) for 10-30 minutes after another four wash steps. Absorbance was read out at 405 nm.

Example 3

Half-Life Determination of the Antibody-TWEAK Complexes Using Biacore

A Biacore 2000 instrument was used with a Biacore streptavidin coated sensor mounted into the system. The system buffer HBS-ET (10 mM HEPES pH 7.4, 150 mM NaCl, 1 mM EDTA, 0.05% Tween® 20) was used at a flow rate of 100 μl/min. The sample buffer was the system buffer. Biotinylated human soluble TWEAK (amino acids 99-249 of SEQ ID NO: 68) and biotinylated murine soluble TWEAK (amino acids 81-225 of SEQ ID NO: 69) was immobilized on different flow cells on the SA sensor at 150 RU each. The flow cell FC1 was used as a blank reference cell. Each antibody was injected into the system as an analyte at 100 nM at 100 μl/min for 2 min association time. The dissociation of the immunecomplexes were monitored for 5 min. The sensor surface was washed with HBS-ET for 10 seconds and regenerated using 2×2 minutes injections with 10 mM glycine pH 2.25. This procedure was done at 25° C. The kinetically rate limiting step of the complex dissociation phase in the interval [240 s-300 s] was taken to calculate the dissociation rate kd [l/s] (Biacore Evaluation Software 4.0). According to the equation t1/2 diss=ln(2)/(60×kd), the half-life of the immunecomplexes in minutes was calculated. Results are shown in tables 1a and 1b, as well as in table 2b.

TABLE 1a

| Antibody | | Human TWEAK t/2 diss [min] 25° C. | Murine TWEAK t/2 diss [min] 25° C. |
|---|---|---|---|
| <TWEAK> 301chi | Chimer[1] | 110 | n.d. |
| <TWEAK> 304chi | Chimer[1] | 37 | n.d. |
| <TWEAK> 305chi | Chimer[1] | 147 | 39 |
| Chimeric P2D10 | Chimer[1] | 76 | 41 |

[1]human constant regions of the human kappa light chain constant region of SEQ ID NO: 59 and the human IgG1 constant region of SEQ ID NO: 61

In a further experiment the half-Life of the antibody-TWEAK complexes (t/2 diss [min] at 25° C.) of the chimeric <TWEAK> 305chi and the chimeric version of P2D10 of WO 2006/130374 was determined (both chimeric antibodies have as human constant regions the human kappa light chain constant region of SEQ ID NO:59 and the human IgG1 constant region of SEQ ID NO: 61).

TABLE 1b

| Antibody | | Human TWEAK t/2 diss [min] 25° C. | Murine TWEAK t/2 diss [min] 25° C. |
|---|---|---|---|
| <TWEAK> 305chi | Chimer[1] | 148 | 41 |
| Chimeric P2D10 | Chimer[1] | 76 | 41 |

[1]human constant regions of the human kappa light chain constant region of SEQ ID NO: 59 and the human IgG1 constant region of SEQ ID NO: 61

The antibodies according to the invention show a valuable properties like a half-life of a complex between soluble human TWEAK (amino acids 99-249 of SEQ ID NO: 68) and antibody of 100 minutes or more, preferably of 110 minutes or more at 25° C., measured by Biacore. Anti-TWEAK antibodies showing such half-life are especially preferred for use in the treatment of autoimmune diseases, rheumatoid arthritis, psoratic arthritis, muscle diseases, e.g. muscular dystrophy, multiple sclerosis, chronic kidney diseases, bone diseases, e.g. bone degeneration in multiple myeloma, systemic lupus erythematosus, lupus nephritis, and vascular injury.

Example 4

Neutralization of TWEAK-Fn14 Interaction (Human)

Blocking of human TWEAK/human Fn14 interaction was shown by receptor interaction ELISA. 96-well Maxisorp® plates (Nunc) were coated with 100 μl 1 μg/ml human Fn14:Fc (extracellular domain of human Fn14 (amino acids 1-75 of SEQ ID NO: 98) fused to Fc portion of human IgG1) in PBS per well for 1.5 h at room temperature and blocked with a solution of 5% FBS in PBS for 30 minutes at room temperature under shaking. In the meantime, human Flag-tagged soluble TWEAK (amino acids 106-249) at 2.5 ng/ml in blocking solution was incubated with different concentrations of anti-TWEAK antibodies or hybridoma supernatant for 2 h at room temperature under shaking. After washing the Fn14-coated plate once with wash buffer (0.1% Tween® 20 in PBS), 100 μl of the TWEAK-antibody solution were transferred to each well and the plate was incubated for 1 h at room temperature, followed by four washes with wash buffer. Wells were filled with 100 μl of anti-FLAG-HRP detection antibody, diluted 1:5000 in blocking buffer, and incubated for 1 h at room temperature.

After four more wash steps, the signal was developed by addition of 100 μl 3,3,5,5-Tetramethylbenzidine (TMB) solution for approximately ten minutes. The reaction was stopped by adding 100 μl of 1 N HCl, and absorbance measured at 450 nm (reference wavelength 620 nm). Results are shown in table 2a and b.

Example 5

Neutralization of TWEAK-Fn14 Interaction (Mouse)

The mouse TWEAK/mouse Fn14 interaction ELISA followed a similar principle as described for the human proteins but used a different detection system, as mouse soluble TWEAK was not tagged. Briefly, Maxisorp plates were coated with mouse Fn14:Fc (extracellular domain of mouse Fn14 (amino acids 1-75 of SEQ ID NO: 98) fused to Fc portion of human IgG1) as described above for human Fn14:Fc, followed by blocking and washing. Mouse soluble TWEAK at 4 ng/ml was pre-incubated with anti-TWEAK-antibodies or hybridoma supernatant in blocking buffer and 100 μl of the mixture were added per well of the Fn14-coated plate. After 1 h of incubation at room temperature and four washes, biotinylated anti-mouse TWEAK antibody at 125 ng/ml in blocking buffer was added for 1 h at room temperature, followed by another four wash steps. The TWEAK antibody was detected by incubation with streptavidin-HRP, diluted 1:5000 in blocking buffer, for 30 minutes at room temperature. Signal was developed and absorbance measured as described above. Results are shown in table 2a and 2b below.

by the ELISA according to the manufacturer's instructions. Results are shown in table 2a and 2b.

TABLE 2a

| Antibody | Inhibition of TWEAK-Fn14 Interaction | | Inhibition of IL-8 Secretion IC50 [ng/ml] |
|---|---|---|---|
| | Human TWEAK IC50 [ng/ml] | Murine TWEAK IC50 [ng/ml] | |
| <TWEAK> 301 Rabbit | 3.4 | 4.7 | 128 |
| TW-304 Rabbit | 2.8 | 3.6 | 109 |
| <TWEAK> 305 Rabbit | 2.5 | 3.3 | 99 |
| <TWEAK> 301 Chimer | 2.8 | 6.4 | 121 |
| <TWEAK> 304chi Chimer | 2.6 | 4.4 | 122 |
| <TWEAK> 305chi Chimer | 2.6 | 4.9 | 104 |

TABLE 2b

| Humanized <TWEAK> 305- antibody | SEQ ID NOs VH, and VL | Interaction Inhibition | | Inhibition of IL8- Secretion [ng/ml] | Biacore t/2 diss. [min] | | | |
|---|---|---|---|---|---|---|---|---|
| | | human IC50 [ng/ml] | murine IC50 [ng/ml] | | 25° C. human | 25° C. murine | 37° C. human | 37° C. murine |
| 27 | 28, 37 | 2.3 | 8.2 | 197 | 110 | 19 | 147 | 19 |
| 28 | 31, 37 | 1.5 | 6.5 | 165 | 87 | 19 | 115 | 17 |
| 29 | 32, 37 | 1.8 | 5.7 | 78 | 146 | 22 | 195 | 21 |
| 30 | 34, 36 | 2.3 | 7.6 | 207 | 50 | 17 | 45 | 15 |
| 31 | 31, 39 | 1.7 | 7.1 | 94 | 115 | 19 | 151 | 19 |
| 32 | 32, 41 | 1.5 | 5.4 | 134 | 67 | 17 | 50 | 20 |
| 33 | 28, 39 | 1.7 | 6.7 | 26 | 127 | 19 | 99 | 15 |
| 34 | 26, 39 | 1.9 | 5.9 | 24 | 158 | 22 | 185 | 20 |

Example 6

IL-8 Secretion ELISA

Blocking of TWEAK activity by anti-TWEAK antibodies in a cellular system was shown in an IL-8 secretion assay using A375 melanoma cells. 10,000 A375 cells (ATCC #CRL1619) were seeded per well of 96-well cell culture plate in 100 μl of growth medium (DMEM with 4.5 g/L glucose, with pyruvate and GlutaMAX™/10% FBS) and incubated at 37° C./5% $CO_2$ for 48 h. Human recombinant soluble TWEAK was pre-incubated at 300 ng/ml with different concentrations of anti-TWEAK antibodies in growth medium for 30 minutes at room temperature. Then, 50 μl of the mixture were added to each well of the cell plate, followed by another 48 h-incubation to allow for IL-8 secretion. 20 μl of the cell supernatant were removed after centrifuging the plate for five minutes at 200×g and mixed with 980 μl of RD5P Calibrator Diluent from the "CXCL8 Quantikine ELISA" kit (R&D Systems). IL-8 was detected Example 7

Determination of the Epitope Region of <TWEAK> 301, <TWEAK> 304, <TWEAK> 305 (abbreviated as TW-301, TW-304, TW-305)

A Biacore 2000 instrument was used together with the Biacore Evaluation Software 4.0. The sample and system buffer was HBS-ET pH 7.4. Due to strong unspecific binding of the TWEAK analyte to the sensor surface epitope mapping of individual antibodies could not be done as usual by a Biacore cross-competition experiment as described by Johne, B., et al., J. Immun. Meth. 160 (1993) 191-198.

Because of the individual biochemical properties of the TWEAK protein another method had to be developed using TWEAK as ligand. Biotinylated TWEAK was immobilized on the streptavidin-coated chip surface and epitope coverage of consecutively injected antibodies (antibody 1) was measured. The aim was to detect the relative binding levels of a secondary antibody (antibody 2) in the presence of an already bound primary antibody. From these relative binding levels a quotient was calculated (Ab2/Ab1, molar ratio given in %, table 3).

5 nM of biotinylated TWEAK was immobilized at 20 µl/min for 1 min on a streptavidin coated sensor flow cell. Primary and secondary mAbs were consecutively injected at 10 µl/min for 4 min into the system at 100 nM each until saturation of the respective TWEAK epitopes was achieved. As a reference an SA coated flow cell was used.

The system was washed with HBS-ET for 20 sec at 30 µl/min followed by two regeneration steps with 1 min at 30 µl/min 6 M GuadHCl and 100 mM HCl. These regeneration steps stripped off the bound mAbs from the sensor surface and immobilized biotinylated TWEAK was irreversibly denatured. The process was repeated by the immobilization of native biotinylated TWEAK protein (feed batch mode) on the same flow cell until the streptavidin sensor surface was completely saturated by biotinylated TWEAK.

TABLE 3

| MR % | Antibody 2 | | |
|---|---|---|---|
| Antibody 1 | TW-301chi | TW-304chi | TW-305chi |
| TW-301chi | 0 | 6 | 9 |
| TW-304chi | 0 | 0 | 3 |
| TW-305chi | 0 | 1 | 0 |

The crossblocking experiment shows accessibility values of the respective antibodies smaller than 10%, which is within the noise of this assay. It is clearly shown, that TW-301chi, TW-304chi and TW-305chi bind to the same epitope region.

Example 8

In Vivo-Inhibition of Collagen-Induced Arthritis (Murine Model of Rheumatoid Arthritis)-Antibody <TWEAK> 305-(Chimeric; TW305)) Inhibits Collagen-Induced Arthritis, a Murine Model of Rheumatoid Arthritis.

Male DBA1/J mice (Jackson Laboratory, Bal Harbor, Me.), 6 to 8 weeks old, were immunized with type II bovine collagen in complete Freund's adjuvant and again in incomplete Freund's adjuvant 3 weeks later (boost, day 0). Mice were administered with chimeric antibody <TWEAK> 305-(=TW305,) (10 mg/kg, n=12), Enbrel (10 mg/kg, n=12) or vehicle (phosphate buffered saline, n=12) every other day starting the day before the boost. Mice were examined for arthritis on day 0, 2, 5, 7, 9, 12 and 14 after the boost. Severity of arthritis was scored based on the following criteria: 1=swelling and/or redness of one digit; 2=swelling in two or more joints; 3=gross swelling of the paw with more than two joints involved; 4=severe arthritis of the entire paw and digits. Compared with vehicle, TW-305 significantly reduced clinical scores (p<0.05, day 14), by a similar magnitude to that of the TNF blocker Enbrel.

Example 9

Generation of IL17 Antigen Binding Sites Via Immunization (Generation of Parent IL17 Antibodies from which the IL17 Antigen Binding Sites for the TWEAK/IL17 Bispecific Antibodies can be Derived)

Immunization was performed within 20 weeks using 5 female Balb/c mice using 250 (1×) and 100 µg (3×) recombinant human IL17 from Peprotech (http://www.peprotech.com; Cat. No.: 200-17 in 1% PBS with 1% Albumin) per mouse. Hybridoma generation. The mouse lymphocytes were isolated and fused with a mouse myeloma cell line using PEG based standard protocols to generate hybridomas. The resulting hybridomas were then screened for the production of antigen-specific antibodies. From resulting hybridomas mouse clone <IL17> 9C6-2B6 was selected using the binding to IL-17 subtypes measured by ELISA and a cytokine release assay (via the inhibition of IL-17A induced hIL-6 and hIL-8 release. Humanization of mouse clone <IL17> 9C6-2B6 resulted in the humanized variants <IL17> 9C6-2B6-134 (with the humanized variant of VH, <IL17> 9C6-2B6-HC134 and humanized variant of VL, <IL17> 9C6-2B6-LC134 of SEQ ID No. 55 and 57) and <IL17> 9C6-2B6 (with the humanized variant of VH, <IL17> 9C6-2B6-HC136 and humanized variant of VL, <IL17> 9C6-2B6-LC136 of SEQ ID No. 56 and 58).

Example 10

Binding to IL-17 and Crossreactivity with IL17 Subtypes Measured by ELISA

NUNC® Maxisorp plates (96-well) are coated with recombinant human IL-17 (Peprotech #200-17, www.peprotech.com) at a concentration of 0.5 µg/ml in PBS (100 ml/well). Plates are incubated at 37° C. on an orbital shaker with agitation for 2 hours. Thereafter coating solution is removed and 100 µl/well PBSTC (phosphate buffered saline, 0.05% Tween®20, 2% chicken serum) is added. Plates are incubated at room temperature for 1 hour. Blocking solution is removed and samples (blank: PBSTC, samples (10 µg/ml in PBS): anti-human IL-17 antibodies <IL17> 9C6-2B6, <IL17> 9C6-2B6-134, <IL17> 9C6-2B6-136, Mab 16-7178-85 of eBioscience (www.ebioscience.com); MAB 317 of R&D Systems (www.rndsystems.com), NVP-AIN-497 (WO 2006/013107); are added to the plate (100 µl/well). Plates are incubated at room temperature with agitation. Samples are removed, plates are washed three times with 200 µl/well PBST (phosphate buffered saline, 0.05% Tween® 20) and second antibody (Goat anti-mouse IgG, Fc gamma, HRP conjugate; Chemicon AP127P, www.millipore.com) for the detection of mouse antibodies or Goat Anti-human IgG, Fc gamma, HRP conjugate (Chemicon AP113P) for the detection of humanized antibodies is added. The second antibody is diluted 1:10000 in PBSTC and plates are incubated for 1 hour at room temperature with agitation. Second antibody is removed, plates are washed three times with 200 µl/well PBST (phosphate buffered saline, 0.05% Tween®20) and 100 µl/well ABTS® (Roche Diagnostics GmbH) is added. Optical density is measured at 405/492 nm in relation to IL-17A binding (set as 100%). Binding to other human IL-17 subtypes (IL-17B, IL-17C, IL-17D, IL-17E and IL-17F) were performed with the same assay format. Results are shown in table 4. The results show that the antibody with the most similar binding behavior against the different IL17 subtypes is MAB 317 of R&D Systems (www.rndsystems.com).

TABLE 4

| IL17-Antibody | Binding (IL-17A binding set as 100) | | | | | |
|---|---|---|---|---|---|---|
| | IL17A | IL17B | IL17C | IL17D | IL17E | IL17F |
| <IL17> 9C6-2B6 | 100 | 0 | 0 | 0 | 0 | 0 |
| <IL17> 9C6-2B6-134 | 100 | 0 | 0 | 0 | 0 | 0 |
| <IL17> 9C6-2B6-136 | 100 | 0 | 0 | 0 | 0 | 0 |
| <IL17> Mab 317 | 100 | 0 | 0 | 0 | 0 | 0 |
| <IL17> 16-7178-85 | 100 | 7 | 97 | 6 | 5 | 5 |

TABLE 4-continued

| | Binding (IL-17A binding set as 100) | | | | |
|---|---|---|---|---|---|
| IL17-Antibody | IL17A | IL17B | IL17C | IL17D | IL17HL17F |
| <IL17> NVP-AIN-497 | 100 | 2 | 2 | 0 | 3 | 62 |

Example 11

Cytokine Release Assay, Inhibition of IL-17A Induced hIL-6 and hIL-8 Release in CCD-25SK Cells The assay is performed as detection of hIL-8 production of CCD-25SK cells (skin fibroblasts, ATCC No: CRL-1474) after stimulation with IL-17A and TNF-alpha with preincubation of anti-IL-17 antibodies. CCD-25SK cells have the IL-17 receptor. Soluble IL-17A binds to the these IL-17 receptor. Antibodies against IL-17A bind to IL-17A. The mechanism is only working in the presence of TNFalpha. Through the binding of IL-17A to the IL-17 receptor, the cells produce hIL-6 and hIL-8 which can be detected by ELISA as a read out. The measured hIL-6 and hIL-8 give the information in which concentrations anti-IL-17 antibodies inhibit the stimulation of CCD-25SK cells by IL-17.

CCD-25SK cells were seeded with a cell density of $2.5 \times 10^4$ cells/well in a 48-well plate (volume 0.45 ml/well) and incubated for 24 h at 37° C. and 5% $CO_2$. After overnight incubation the cells were treated with anti-IL-17 antibodies for 30 minutes with end concentrations of 9000; 3000; 1000; 333.3; 111.1; 37.03; 12.34; and 4.11 ng/ml. Each antibody dilution series was made with medium, 50 µl/well (10× concentrated). After 30 min the cells were stimulated with a mixture of 10 ng/ml IL-17A and 50 pg/ml TNF-alpha. 50 µl/well (10× concentrated) and incubated for 24 h at 37° C. and 5% $CO_2$. After overnight incubation the supernatants were transferred to 96-well plates and frozen at −20° C. as intermediates for hIL-8 ELISA.

hIL-6 and hIL-8 ELISA was performed as follows. 100 µl diluted capture antibody was added to each well and incubated overnight at 4° C. Dilutions were made with coating buffer. Plates were aspirated, washed with 200 µl/well for 3 times, blocked with 200 µl/well assay diluent, and incubated for 1 h at RT. The plates were aspirated and washed with 200 µl/well for 3 times. 100 µl standard and samples were added and incubated for 2 h at RT. Standard dilution series: 400 pg/ml; 200 pg/ml; 100 pg/ml; 50 pg/ml; 25 pg/ml; 12.5 pg/ml; 6.3 pg/ml and assay diluent as negative control. Sample dilution was 1:200. Plates were aspirated and washed with 250 µl/well for 4 times. 100 µl conjugate was added to each well. The conjugate was prepared with detection antibody and enzyme reagent 1:250 diluted in assay diluent. Plates were aspirated and washed with 250 µl/well for 6 times. 100 µl substrate was added to each well and incubated for 12 minutes. After incubation the reaction was stopped with 50 µl/well 1M $H_2SO_4$. Read out was performed at 450 nm within 30 min with λ correction at 570 nm. Results are shown in table 5 ($IC_{50}$ values measured in relation to a maximal inhibition of 80%).

TABLE 5

| Antibody | IL-6 Inhibition IC50 (nM) | IL-8 Inhibition IC50 (nM) |
|---|---|---|
| <IL17> 9C6-2B6 | 1.6 | 4.8 |
| <IL17> 9C6-2B6-134 | n.d. | 4.5 |
| <IL17> 9C6-2B6-136 | n.d. | 1.8 |
| Mab 317 | 2.8 | n.d |

Example 12

Crossreactivity with Cynomolgous IL-17A (Binding Assay)

Relative binding to human and cynomolgous IL17A was determined. The binding assay was performed according to example 2. The results for two separates experiments (one in which mouse IL17 antibodies were compared and one in which human and humanized IL17 antibodies were compared) are shown in tables 6a and 6b.

TABLE 6a

| IL17 Antibody (mouse) | Relative binding to human IL-17A in % | Relative binding to cynomolgous IL-17A in % |
|---|---|---|
| Mab 317 (R&D) | 100 | 100 |
| eBio64CAP17 | 122 | 124 |
| 9C6/2B6 | 127 | 134 |

TABLE 6b

| IL17 Antibody (human/ized) | Relative binding to human IL-17A | Relative binding to cynomolgous IL-17A |
|---|---|---|
| NVP-AIN-497 | 100 | 100 |
| 9C6/2B6-134 | 108 | n.d |
| 9C6/2B6-136 | 108 | 149 |

Example 13

Cynomolgous Monkey (*Maccaca Fasicularis*) Cytokine Release Assay, Inhibition of Cynomolgous IL-17A Induced IL-6 and IL-8 Production Cynomolgous dermal fibroblasts (CDF) cells produce cynomolgous IL-6 and IL-8 in response to human or cynomolgous IL-17A stimulation. The assay is performed to measure the inhibition of this cynomolgous IL-17A stimulated IL-6 and IL-8 production by CDF cells following preincubation of the cells with anti-IL-17 antibodies raised against human IL-17 prior to stimulation.

CDF cells are seeded with a cell density of $2 \times 10^5$ cells/ml in a volume of 0.5 ml in a 48-well plate, and incubated overnight at 37° C. and 5% $CO_2$ to adhere. After overnight incubation, the media is replaced with 400 µl fresh media and the cells are treated with anti-IL-17 antibodies for 30 minutes across a range of antibody concentrations (10000, 3000, 1000, 300, 100, 30, 10, 3, 0 ng/ml). Each antibody dilution series is made with medium using 50 µl/well (10× concentrated). After 30 min the cells are stimulated with 100 ng/ml IL-17A (50 µl of 1000 ng/ml 10× concentration) and incubated overnight (18 h) at 37° C. and 5% $CO_2$. After the incubation period, supernatants are transferred into fresh tubes and either analyzed immediately or stored at −80° C. until analysis by ELISA hIL-6 and hIL-8 ELISA were shown to be cross-reactive with their respective cynomolgous cytokines and are used to quantitate cytokine levels. For the ELISA's 100 µl diluted capture antibody is added to each well and incubated overnight at 4° C. Dilutions are made with coating buffer. Plates are aspirated, washed with 200 μl/well for 3 times, blocked with 200 μl/well assay diluent, and incubated for 1 h at RT. The plates are aspirated and washed with 200 μl/well for 3 times. 100 μl standard and samples are added and incubated for 2 h at RT according to the manufacturer's instructions. Plates are aspirated and washed with 250 μl/well for at least 3 times. 100 μl conjugate is added to each well. The conjugate is prepared with detection antibody and enzyme reagent 1:250 diluted in assay diluent. Plates are aspirated and washed with 250 μl/well for at least 3 times. 100 μl substrate was added to each well and incubated until sufficient color had developed for reading. After incubation the reaction is stopped with 50 μl/well 1M $H_2SO_4$ and read on the plate reader at a wavelength of 450 nm within 30 min.

Example 14

Expression and Purification of Bispecific <TWEAK-IL-17> Antibody Molecules <Tweak-IL-17> #2, <Tweak-IL-17> #4, <Tweak-IL-17> #20, <Tweak-IL-17> #21, <Tweak-IL-17> #23, <Tweak-IL-17> #24, <Tweak-IL-17> #5

Light and heavy chains of the following bispecific antibodies <Tweak-IL-17> #2, <Tweak-IL-17> #4, <Tweak-IL-17> #20, <Tweak-IL-17> #21, <Tweak-IL-17> #23, <Tweak-IL-17> #5 (based on the antigen binding sites (VH/VL) as described in the Table 7 below) were constructed in genomic, partly genomic or cDNA-derived expression vectors as described. For the bispecific, bivalent antibodies <Tweak-IL-17> #2, <Tweak-IL-17> #24 the format described in WO 2009/080253 ("CrossMabs" or "CH1-CL domain exchanged antibodies") has been used. For the bispecific, bivalent <Tweak-IL-17> #4, <Tweak-IL-17> #20, <Tweak-IL-17> #21, <Tweak-IL-17> #23 the format described in WO2011/117330 ("bispecific one-armed scFab antibodies") has been used, and for <Tweak-IL-17> #5 the bispecific, tetravalent format, wherein the scFabs are fused at the N-terminus of the heavy chains described in WO 2010/112193 has been used. WO 2009/080253, WO 2011/117330 and WO 2010/112193 are incorporated herein by reference).

The plasmids were amplified in *E. coli*, purified, and subsequently HEK293 cells were transfected for transient expression of recombinant proteins. After 7 days of cultivation, the supernatants of HEK293 cells were harvested, filtered and the bispecific bivalent antibodies were purified.

TABLE 7

Construction of different <Tweak/IL-17> bispecific antibodies based on the corresponding TWEAK and IL17 VH and VL domains, and the respective IgG constant region (with mutations, if present; numbering according to the EU index of Kabat)

| | VH <TWEAK> | VL <TWEAK> | VH <IL17> | VL <IL17> | IgG subtype with mutation(s) |
|---|---|---|---|---|---|
| <Tweak-IL-17> #2 | SEQ ID NO: 28 | SEQ ID NO: 37 | SEQ ID NO: 56 | SEQ ID NO: 58 | IgG1 with Y349C, T366W mutations in one of the two CH3 domains and S354C, T366S, L368A, Y407V mutations in the other of the two CH3 domains |
| <Tweak-IL-17> #4 | SEQ ID NO: 28 | SEQ ID NO: 37 | SEQ ID NO: 56 | SEQ ID NO: 58 | IgG1 with Y349C, T366W mutations in one of the two CH3 domains and S354C, T366S, L368A, Y407V mutations in the other of the two CH3 domains |
| <Tweak-IL-17> #5 | SEQ ID NO: 28 | SEQ ID NO: 37 | SEQ ID NO: 56 | SEQ ID NO: 58 | IgG1 |
| <Tweak-IL-17> #20 | SEQ ID NO: 28 | SEQ ID NO: 37 | SEQ ID NO: 56 | SEQ ID NO: 58 | IgG4 with a) mutations S228P and L235E; and b) with Y349C, T366W mutations in one of the two CH3 domains and S354C, T366S, L368A, Y407V mutations in the other of the two CH3 domains |
| <Tweak-IL-17> #21 | SEQ ID NO: 28 | SEQ ID NO: 37 | SEQ ID NO: 55 | SEQ ID NO: 57 | IgG4 with a) mutations S228P and L235E; and b) with Y349C, T366W mutations in one of the two CH3 domains and S354C, T366S, L368A, Y407V mutations in the other of the two CH3 domains |
| <Tweak-IL-17> #23 | SEQ ID NO: 28 | SEQ ID NO: 37 | SEQ ID NO: 55 | SEQ ID NO: 57 | IgG1 with a) mutations L234A, L235A and P329G; and b) with Y349C, T366W mutations in one of the two CH3 domains and S354C, T366S, L368A, |

TABLE 7-continued

Construction of different <Tweak/IL-17> bispecific antibodies based on the corresponding TWEAK and IL17 VH and VL domains, and the respective IgG constant region (with mutations, if present; numbering according to the EU index of Kabat)

| | VH <TWEAK> | VL <TWEAK> | VH <IL17> | VL <IL17> | IgG subtype with mutation(s) |
|---|---|---|---|---|---|
| <Tweak-IL-17> #24 | SEQ ID NO: 28 | SEQ ID NO: 37 | SEQ ID NO: 55 | SEQ ID NO: 57 | Y407V mutations in the other of the two CH3 domains IgG1 with a) mutations L234A, L235A and P329G; and b) with Y349C, T366W mutations in one of the two CH3 domains and S354C, T366S, L368A, Y407V mutations in the other of the two CH3 domains |

Bispecific antibodies were purified from cell culture supernatants by affinity chromatography using MabSelect SuRe™ (GE Healthcare, Sweden). The subsequent chromatographic steps (size exclusion chromatography (Superdex200 HiLoad 120 ml 16/60 gel filtration column, GE Healthcare, Sweden) or ion exchange chromatography (MacroPrep CHT™ TypeII 10 ml, Bio-Rad plus size exclusion chromatography) was chosen in respect to the individual product related sideproducts of the bispecific antibodies after MabSelect SuRe™ chromatography.

Briefly, sterile filtered cell culture supernatants were captured on a MabSelect SuRe resin equilibrated with PBS buffer (10 mM $Na_2HPO_4$, 1 mM $KH_2PO_4$, 137 mM NaCl and 2.7 mM KCl, pH 7.4), washed with equilibration buffer and eluted with 25 mM sodium citrate at pH 3.0. The eluted protein fractions were pooled and neutralized with 2M Tris, pH 9.0. The antibody pools were prepared for hydrophobic interaction chromatography by rebuffering in 10 mM $NaH_2PO_4$, 20 mM MES, 50 mM NaCl, 0.1 mM $CaCl_2$, pH 7.5. After equilibration of the CHT column with equilibration buffer (10 mM $NaH_2PO_4$, 20 mM MES, 50 mM NaCl, 0.1 mM $CaCl_2$, pH 7.5), the antibodies were applied to the CHT column, washed with equilibration buffer and eluted in an linear gradient to 10 mM $NaH_2PO_4$, 20 mM MES, 500 mM NaCl, 0.1 mM $CaCl_2$, pH 7.5. The bispecific antibody containing fractions (from ion exchange chromatography or MabSelect SuRe affinity chromatography) were pooled and further purified by size exclusion chromatography using a Superdex 200 26/60 GL (GE Healthcare, Sweden) column equilibrated with 20 mM histidine, 140 mM NaCl, pH 6.0. The bispecific antibody containing fractions were pooled, concentrated to the required concentration using Vivaspin ultrafiltration devices (Sartorius Stedim Biotech S.A., France) and stored at −80° C.

Example 15

SDS-CE and Analytical SEC of Bispecific Molecules
SDS-CE

Purity, antibody integrity and molecular weight of bispecific and control antibodies were analyzed by CE-SDS using microfluidic Labchip technology (Caliper Life Science, USA). 5 µl of protein solution was prepared for CE-SDS analysis using the HT Protein Express Reagent Kit according manufacturer's instructions and analyzed on LabChip GXII system using a HT Protein Express Chip. Data were analyzed using LabChip GX Software.

Analytical Size Exclusion Chromatography

Size exclusion chromatography for the determination of the aggregation and oligomeric state of antibodies was performed by HPLC chromatography. Briefly, purified antibodies at various levels of the purification process were applied to a Tosoh TSKgel G3000SW column in 300 mM NaCl, 50 mM KH2PO4/K2HPO4, pH 7.5 on an Agilent HPLC 1100 system or to a Superdex 200 column (GE Healthcare) in 2×PBS on a Dionex HPLC-System. The eluted protein was quantified by UV absorbance and integration of peak areas. BioRad Gel Filtration Standard 151-1901 served as a standard.

TABLE 8

Yield, purity profile and aggregation tendencies (aggregate tendencies are reflected by % monomers after Protein A)

| | Titer (mg/l) | Light chain mispairing (CE-SDS) | % Monomer Protein A (SE-HPLC) | Estimated purity after 2$^{nd}$ column (ESI-MS) |
|---|---|---|---|---|
| <TweakIL-17>#4 | 44 | ~18% | ~70% | <80% |
| <Tweak-IL-17>#5 | 13 | ~10% | ~60% | >90% |
| <Tweak-IL-17>#20 | 65 | ~9% | ~80% | >95% |
| <Tweak-IL-17>#21 | 25 | ~4% | ~70% | >95% |
| <Tweak-IL-17>#23 | 73 | 12% | ~60% | <80% |
| <Tweak-IL-17> #2 | 8 | ~10% | >90% | >90% |
| <Tweak-IL-17 #24 | 8 | n.a. | ~80% | <80% |

Example 16

Inhibition of IL-17 Induced Cytokine Stimulation of Human Synovial Fibroblasts

The anti-IL-17 component of different <Tweak-IL-17> bispecific antibodies was tested for inhibition of an IL-17-induced production of pro-inflammatory cytokines (e.g. human IL-6, human IL-8) by human adult fibroblast-like synoviocytes obtained from RA patients (HFLS-RA). After establishment of a dose-response response of different RA-FLS donors, the potency of several lead candidates was assessed.

HFLS-RA (Cat. #408RA-05a) were purchased from Cell Applications Inc. (San Diego, Calif., USA; German distributor: tebu-bio, Offenbach, Germany). Cells were thawed, expanded in Synoviocyte Growth Medium (Cell Applications, Inc.; Cat. #415-500), detached with Accutase (PAA Laboratories GmbH, Pasching, Austria; Cat. #L11-007) before approx. $2 \times 10^4$ HFLS-RA cells/well were seeded in 200 µl/well medium in 96 wF cell culture plates (Costar/Corning Life Sciences, Amsterdam, The Netherlands; Cat. #3596).

Cells were pre-cultured for two days at 37° C., 5% $CO_2$ before cytokines (and optionally antibodies) were added. Prior to the cytokine addition, medium was removed and 150 µl/w of the corresponding cytokine (optional: antibody) dilution was added: 0-10 µg/ml rec. human IL-17A (PeproTech, Hamburg, Germany; Cat. #200-17); 0-25 µg/ml rec. human TWEAK (R&D Systems, Wiesbaden, Germany; Cat. #1090-TW/CF), or 0-10 µg/ml rec. human TNFα (R&D Systems; Cat. #210-TA/CF) was titrated in ten 1:10 dilution steps to obtain an ED50 value for the indicated cytokines. TWEAK was used as negative and TNF was used as positive control. The cells were incubated for 6 h, 24 h and 72 h at 37° C., 5% CO2, whereas 72 hrs was used for the following experiments as this incubation time gave the most robust cytokine response (on a protein level). Cells were pre-incubated with several antibodies at different concentrations ($c_{fin}$=0-150/500 nM) for 30 min at 37° C., 5% $CO_2$ before stimulation with 100 ng/ml-10 µg/ml TWEAK for additional 72 hrs was applied.

TABLE 9

Effective dose (ED50) values in ng/ml of cytokine induction by IL-17, Tweak and TNFalpha of synovial fibroblasts.

| Cytokine | Human IL-6 | Human IL-8 | G-CSF |
| --- | --- | --- | --- |
| +IL-17A | 1.0 | 5.0 | 2.1 |
| +TWEAK | >100 | >100 | >100 |
| +TNFalpha | 0.2 | 0.7 | 0.4 |

TABLE 10

Inhibitory concentration (IC50) in nM of <IL-17> parent antibodies and <Tweak-IL-17> bispecific antibodies after cytokine induction by IL-17 of synovial fibroblasts calculated as inhibitory concentration IC50/per valency (=per IL17 binding arm).

| Antibody | IL-6 IC50 [nM] | IL-8 IC50 [nM] |
| --- | --- | --- |
| <IL-17>9C6-2B6-134 | 3.56 | 2.20 |
| <IL-17>9C6-2B6-136 | 1.62 | 1.74 |
| <Tweak-IL-17>#4 | 1.72 | 1.10 |
| <Tweak-IL-17>#20 | 1.38 | 0.90 |
| <Tweak-IL-17>#5 | 1.32 | 1.12 |
| <Tweak-IL-17>#21 | 2.71 | 1.71 |

Interestingly the bispecific antibodies according to the invention show an improved IC50 per binding valency compared to parent IL17 antibodies.

Cytokine Determination Via CBA

After this, approximately 120 µl/w supernatant was transferred in 96 w RB plates and stored at −20° C. until cytokine analysis was performed. For this the Cytometric Bead Array (CBA) platform was used and in particular the production of IL-6 and IL-8 (or its inhibition) was analyzed. The assay was performed according to manufacturer's instructions of the Human Soluble Protein Master Buffer Kit (BD Biosciences, Heidelberg, Germany, Cat. #558265) using the human IL-6 (BD Biosciences, Cat. #558276) and IL-8 (BD; Cat. #558277) flex sets. Plates were measured with a FACS Array and analyzed using FCAP software (both from BD).

Example 17

Inhibition of Tweak Induced Proliferation of Human Synovial Fibroblasts

Human Adult Fibroblast-Like Synoviocytes obtained from RA patients (HFLS-RA; Cat. #408RA-05a) were purchased from Cell Applications Inc. (San Diego, Calif., USA; German distributor: tebu-bio, Offenbach, Germany). Cells were thawed, expanded and—after detachment with Accutase (PAA Laboratories GmbH, Pasching, Austria; Cat. #L11-007) $2 \times 10^4$ HFLS-RA cells/well were seeded in 100 µl/well medium in 96 wF white chimney plate (Greiner Bio-one, Frickenhausen, Germany; #655098) for subsequent CellTiter Glo Proliferation/Viability assay. In preliminary experiments the proliferation was assessed using the Click-iT EdU kit according the manufacturer's instructions (see below).

Recombinant human TWEAK (R&D Systems, Wiesbaden, Germany; Cat. #1090-TW/CF) was titrated from 0-6,000 ng/ml in 1:3 dilution steps with 100 µl/w in triplicates to obtain the EC50 value of a dose-response-curve. The total volume per well was 200 µl. Plates were then incubated for 72 hrs at 37° C., 5% $CO_2$ until proliferation was measured.

In final experiments, cells were pre-incubated with indicated antibodies at different concentrations ($c_{fin}$=0-150 nM) for 30 min at 37° C., 5% $CO_2$. After this, cells were stimulated by adding 10-20 ng/ml rec. human TWEAK to each well (50 µl/w) and culturing for additional 72 hrs. Stimulation with recombinant IL-17 or TNFalpha did not lead to a measurable induction of HFLS proliferation.

Proliferation Assay

The CellTiter Glo kit (Promega GmbH, Mannheim, Germany; Cat. #G7571) was used to assess the proliferation as measured by general cell viability/activity. Briefly, substrate and buffers were thawed and substrate was dissolved in 10 ml buffer. For equilibration the plate was incubated for 30 min at room temperature, centrifuged, and 100 W cell supernatant was added to 100 W of the CellTiter Glo reagent (per well). Plates were shaked 2 min and, after signal equilibration for 10 min, luminescence was measured using a Tecan Infinite 2000 reader (Tecan, Crailsheim, Germany) with the following settings: 96 w F Greiner chimney white/luminescence/0-1000 ms.

In preliminary experiments the proliferation was assessed using the Click-iT EdU A647 kit according the manufacturer's instructions (Invitrogen, Cat. #A10208).

TABLE 11

HFLS and HFSL-RA were stimulated and proliferation was analyzed after 72 hrs.

| | HFLS | HFLS-RA |
| --- | --- | --- |
| Effective dose (ED50) | 55 ng/ml | 44 ng/ml |
| Proliferation compared to unstimulated | ~3-fold | ~3-fold |

TABLE 12

Inhibition of Tweak induced HFLS proliferation by <Tweak-IL-17> bispecific antibodies calculated as inhibitory concentration IC50/per valency (=per Tweak binding arm).

| Antibody | IC50 (nM) |
|---|---|
| Humanized <Tweak>TW-305 (HC4, LC2) | 0.152 |
| <Tweak-IL-17>#2 | 0.065 |
| <Tweak-IL-17>#4 | 0.157 |
| <Tweak-IL-17>#20 | 0.080 |
| <Tweak-IL-17>#5 | 0.152 |

Example 18

Small-Scale Dynamic Light Scattering (DLS)-Based Viscosity Measurement of <TWEAK-IL-17> Antibody Molecules.

Viscosity measurement was essentially performed as described in [He, F., et al., Analytical Biochemistry 399(1) (2009), 141-3]. Briefly, samples are concentrated to various protein concentrations in 200 mM arginine succinate, pH 5.5, before polystyrene latex beads (300 nm diameter) and Polysorbate 20 (0.02% v/v) are added. Samples are transferred into an optical 384-well plate by centrifugation through a 0.4 μm filter plate and covered with paraffine oil. The apparent diameter of the latex beads is determined by dynamic light scattering at 25° C. The viscosity of the solution can be calculated as $\eta=\eta_0(r_h/r_{h,0})$ (η: viscosity; $\eta_0$: viscosity of water; $r_h$: apparent hydrodynamic radius of the latex beads; $r_{h,0}$: hydrodynamic radius of the latex beads in water.

To allow comparison of various samples at the same concentration, viscosity-concentration data were fitted with the Mooney equation (Equation 1) [(Mooney, Colloid Sci, 1951; Monkos, Biochem. Biophys. Acta 1997)] and data interpolated accordingly.

$$\eta = \eta_0 \exp\left(\frac{S\Phi}{1-K\Phi}\right)$$

(S: hydrodynamic interaction parameter of the protein; K: self-crowding factor; Φ: volume fraction of the dissolved protein)

For comparison the data of IL17 based bispecific antibody D2E7-B6-17.8 DVD-Ig (which binds TNF alpha as second specificity) described in WO 2010/102251 was also determined.

TABLE 13

Viscosity of bispecific antibodies was measured at various concentrations.

| | Viscosity at 70 mg/ml | Viscosity at 100 mg/ml | Viscosity at 150 mg/ml |
|---|---|---|---|
| <Tweak-IL-17>#4 | 2.2 mPa · s | 3.5 mPa · s | 8.2 mPa · s |
| <Tweak-IL-17>#20 | 2.1 mPa · s | n.d. | n.d. |
| <Tweak-IL-17>#21 | 2.3 mPa · s | n.d. | n.d. |
| <Tweak-IL-17>#23 | 2.7 mPa · s | 3.3 mPa · s | 7.4 mPa · s |
| D2E7-B6-17.8 DVD-Ig | 3.4 mPa · s | 6.5 mPa · s | n.d. |

Stability of Bispecific Antibodies

Samples are concentrated to a final concentration of 150 mg/mL in 200 mM arginine succinate, pH 5.5, sterile filtered and quiescently stored at 40° C. for 4 days. Before and after storage, the content of high molecular weight (HMW) species is determined by size-exclusion chromatography. The difference in HMW content between the stored sample and a sample measured immediately after preparation is reported as "HMW increase". For comparison the data of IL17 based bispecific antibody D2E7-B6-17.8 DVD-Ig (which binds TNF alpha as second specificity) described in WO 2010/102251 was also determined.

TABLE 14

Stability of bispecific antibodies was assessed by DLS and SE.-HPLC.

| | <Tweak-IL-17>#20 | <Tweak-IL-17>#21 | <Tweak-IL-17>#23 | D2E7-B6-17.8 DVD-Ig |
|---|---|---|---|---|
| DLS aggregation onset temperature (=aggregation temperature) | ≈57° C. | ≈61° C. | ≈64° C. | ≈54° C. |
| 4 d storage at 40° C. at 150 mg/ml (HMW increase) | <5 area-% | n.d. | n.d. | n.d. |

Example 19

Binding of the Bispecific <TWEAK/IL17> Antibodies According to the Invention

The <IL17> and <TWEAK> binding affinity of bispecific antibodies and parent antibodies was measured by Surface Plasmon Resonance (SPR) using a BIAcore® T100 instrument (GE Healthcare) at 25° C. The BIAcore® system is well established for the study of molecule interactions. SPR-technology is based on the measurement of the refractive index close to the surface of a gold coated biosensor chip. Changes in the refractive index indicate mass changes on the surface caused by the interaction of immobilized ligand with analyte injected in solution. The mass increases if molecules bind immobilized ligands on the surface, and vice versa, the mass decreases in case of dissociation of the analyte from the immobilized ligand (reflecting complex dissociation). SPR allows a continuous real-time monitoring of ligand/analyte binding and thus the determination of the association rate constant (ka), the dissociation rate constant (kd), and of the equilibrium constant (KD).

IL17 Binding Affinity

Around 12000 resonance units (RU) of the capturing system (10 μg/ml goat anti human F(ab')2; Order Code: 28958325; GE Healthcare Bio-Sciences AB, Schweden) were coupled on a CM5 chip at pH 5.0 by using an amine coupling kit supplied by the GE Healthcare. The sample and system buffer was PBS-T (10 mM phosphate buffered saline including 0.05% Tween20) pH 7.4. The bispecific antibody was captured by injecting a 50 nM solution for 1 min at a flow of 10 μl/min. Association was measured by injection human IL17 in various concentrations in solution for 3 min at a flow of 30 μl/min starting with 50 nM in 1:1 dilutions. The dissociation phase was monitored for up to 5 min and triggered by switching from the sample solution to running buffer. The surface was regenerated by two times 60 sec. washing with a glycin pH 2.1 solution at a flow rate of 30 μl/min. Bulk refractive index differences were corrected by subtracting the response obtained from a goat anti human F(ab')2 surface. Blank injections are also subtracted (=double referencing). For calculation of apparent $K_D$ and other kinetic parameters the Langmuir 1:1 model was used. Results are shown in Table 17 below.

TABLE 15

Binding affinity to human IL17

| Antibody | IL-17 A/A* (app KD) | IL-17 A/F (KD) | IL-17 F/F (KD) |
|---|---|---|---|
| <IL17>9C6-2B6-136 | 0.18 nM | 0.26 nM | no binding |
| <Tweak-IL-17>#2 | 0.15 nM | 0.25 nM | no binding |
| <Tweak-IL-17>#4 | 0.15 nM | 0.27 nM | no binding |
| <Tweak-IL-17>#20 | <0.2 nM | n.d. | no binding |

TWEAK Binding Affinity

Due to strong unspecific binding of the TWEAK analyte to the sensor surface, a reverse setup—using TWEAK as ligand—was chosen. Around 100 resonance units (RU) of TWEAK was immobilized on the C1 chip surface at pH 5.0 using an amine coupling kit supplied by the GE Healthcare. The sample and system buffer was PBS-T (10 mM phosphate buffered saline including 0.05% Tween20) pH 7.4. Association was measured by injection the bispecific antibody in various concentrations in solution for 3 min at a flow of 30 μl/min starting with 50 nM in 1:1 dilutions. The dissociation phase was monitored for up to 10 min and triggered by switching from the sample solution to running buffer. The surface was regenerated by three times 30 sec. washing with a 3M MgCl2 solution at a flow rate of 30 μl/min. Bulk refractive index differences were corrected by subtracting the response obtained from a blank-coupled surface. Blank injections are also subtracted (=double referencing). For calculation of apparent $K_D$ and other kinetic parameters the Langmuir 1:1 model was used. Results are shown in the table 18 below.

TABLE 16

Binding affinity to human TWEAK

| | Ligand | ka (1/Ms) | kd (1/s) | App. KD (M) | T½ (min) |
|---|---|---|---|---|---|
| <TWEAK>305 (antibody 27 = humanized variant with HC4 LC2) | Tweak-Fc | 2.27E+06 | 5.71E−05 | 2.52E−11 | 202.4 |
| <TWEAK>305 (antibody 27) -Fab | | 4.72E+06 | 7.09E−05 | 1.50E−11 | 163.0 |
| <Tweak-IL-17>#4 | | 4.26E+05 | 5.42E−05 | 1.27E−10 | 213.0 |
| <Tweak-IL-17>#20 | | 8.10E+05 | 5.31E−05 | 6.56E−11 | 217.6 |

Simultaneous Binding of <TWEAK/IL17> Antibodies to Both Targets, Human TWEAK and Human IL17

Around 12000 resonance units (RU) of the capturing system (10 μg/ml goat anti human F(ab')2; Order Code: 28958325; GE Healthcare Bio-Sciences AB, Sweden) were coupled to a CM5 chip (GE Healthcare BR-1005-30) at pH 5.0 by using an amine coupling kit supplied by the GE Healthcare. The sample and system buffer was PBS-T (10 mM phosphate buffered saline including 0.05% Tween20) pH 7.4. The temperature of the flow cell was set to 25° C. and of the sample block to 12° C. Before capturing, the flow cell was primed with running buffer twice. The bispecific antibody was captured by injecting a 50 nM solution for 60 sec at a flow of 10 μl/min. Independent binding of each ligand to the bispecific antibody was analyzed by determining the active binding capacity for each ligand, either added sequentially or simultaneously (flow of 30 μl/min):
1) Injection of human Tweak-Fc with a concentration of 50 nM for 120 sec (identifies the single binding of the antigen). 2) Injection of human IL17A/A with a concentration of 50 nM for 120 sec (identifies single binding of the antigen). 3) Injection of human Tweak-Fc with a concentration of 50 nM for 120 sec followed by an additional injection of human IL17A/A with a concentration of 50 nM (identifies binding of IL17A/A in the presence of Tweak). 4) Injection of human IL17A/A with a concentration of 50 nM for 120 sec followed by an additional injection of human Tweak-Fc with a concentration of 50 nM (identifies binding of Tweak in the presence of IL17A/A). 5) Co-Injection of human IL17A/A with a concentration of 50 nM and of human Tweak-Fc with a concentration of 50 nM for 120 sec (identifies the binding of Tweak and of IL17A/A at the same time).

The surface was regenerated by 2 times 60 sec washing with a Glycine pH 2.1 solution at a flow rate of 30 μl/min. Bulk refractive index differences were corrected by subtracting the response obtained from a goat anti human IgG surface. The bispecific antibody is able to bind both antigens mutual independently if the resulting final signal of the approaches 3, 4 & 5 equals the sum of the individual final signals of the approaches 1 and 2.

TABLE 17

Simultaneous of <TWEAK/IL17> antibodies to both targets <TWEAK> and <IL17>

| | TWEAK-Fc addition (RU) | IL-17 addition (RU) | Addition of Tweak-Fc/IL-17 mixture (RU) |
|---|---|---|---|
| <Tweak-IL-17>#4 | 88 | 42 | 135 |
| <Tweak-IL-17>#20 | 139 | 42 | 186 |

What is claimed is:

1. A bispecific antibody comprising a first antigen-binding site that specifically binds to human TWEAK and a second antigen-binding site that specifically binds to human IL17, wherein the bispecific antibody inhibits:
   a) TWEAK induced proliferation of human fibroblast-like synoviocytes-rheumatoid arthritis (HFLS-RA) with an IC50 value of 0.2 nM or lower; and
   b) IL17 induced IL6 cytokine stimulation of human fibroblast-like synoviocytes-rheumatoid arthritis (HFLS-RA) with an IC50 value of 3.0 nM or lower.

2. The bispecific antibody of claim 1, wherein the bispecific antibody further inhibits IL17 induced IL8 cytokine stimulation of human fibroblast-like synoviocytes-rheumatoid arthritis (HFLS-RA) with an IC50 value of 2.0 nM or lower.

3. The bispecific antibody according to claim 1, characterized in that
   i) said first antigen-binding site comprises CDR1H of SEQ ID NO:17, CDR2H of SEQ ID NO:18, CDR3H of SEQ ID NO:19, and CDR1L of SEQ ID NO:20, CDR2L of SEQ ID NO:21, CDR3L of SEQ ID NO:22 and
   ii) said second antigen-binding site comprises CDR1H of SEQ ID NO:47, CDR2H of SEQ ID NO:48, CDR3H of SEQ ID NO:49, and CDR1L of SEQ ID NO:50, CDR2L of SEQ ID NO:51, CDR3L of SEQ ID NO:52.

4. The bispecific antibody according to claim 3, which is chimeric or humanized.

5. The bispecific antibody according to claim 1, characterized in that the bispecific antibody is bivalent.

6. The bispecific antibody according to any of claims 1, 3, and 5, characterized in that
   i) said first antigen-binding site comprises
      the variable heavy chain domain (VH) of SEQ ID NO:28, and the variable light chain domain of SEQ ID NO:37; and
   ii) said second antigen-binding site comprises
      the variable heavy chain domain (VH) of SEQ ID NO:56, and the variable light chain domain of SEQ ID NO:58.

7. A bispecific antibody comprising a first antigen-binding site that specifically binds to human TWEAK and a second antigen-binding site that specifically binds to human IL17, characterized in that:
   i) said first antigen-binding site comprises
      CDR1H of SEQ ID NO:17, CDR2H of SEQ ID NO:18, CDR3H of SEQ ID NO:19, and CDR1L of SEQ ID NO:20, CDR2L of SEQ ID NO:21, CDR3L of SEQ ID NO:22; and
   ii) said second antigen-binding site comprises
      CDR1H of SEQ ID NO:47, CDR2H of SEQ ID NO:48, CDR3H of SEQ ID NO:49, and CDR1L of SEQ ID NO:50, CDR2L of SEQ ID NO:51, CDR3L of SEQ ID NO:52.

8. The bispecific antibody according to claim 7, characterized in that
   i) said first antigen-binding site comprises
      the variable heavy chain domain (VH) of SEQ ID NO:28, and the variable light chain domain of SEQ ID NO:37; and
   ii) said second antigen-binding site comprises
      the variable heavy chain domain (VH) of SEQ ID NO:56, and the variable light chain domain of SEQ ID NO:58.

9. The bispecific antibody according to any of claims 1, 3-5, 7, and 8 characterized in that it is of IgG1 or IgG4 subclass.

10. The bispecific antibody according to claim 9, characterized in being of human IgG1 subclass with the mutations L234A and L235A (numbering according to the EU index of Kabat).

11. The bispecific antibody according to claim 9, characterized in being of human IgG1 subclass with the mutations L234A, L235A and P329G (numbering according to the EU index of Kabat).

12. The bispecific antibody according to claim 9, characterized in being of human IgG4 subclass with the mutations S228P and L235E (numbering according to the EU index of Kabat).

13. The bispecific antibody according to claim 9, characterized in being of human IgG4 subclass with the mutations S228P, L235E and P329G (numbering according to the EU index of Kabat).

14. A pharmaceutical composition comprising an antibody according to any one of claims 1, 3-5, 7, and 8.

* * * * *